United States Patent
Ikeda et al.

(10) Patent No.: US 6,444,677 B2
(45) Date of Patent: *Sep. 3, 2002

(54) 5-MEMBERED HETEROARYL SUBSTITUTED 1,4-DIHYDROPYRIDINE COMPOUNDS AS BRADYKININ ANTAGONISTS

(75) Inventors: Takafumi Ikeda, Aichi; Mitsuhiro Kawamura, Aichi-ken; Noriaki Murase, Aichi-ken; Seiji Nukui, Aichi-ken; Yuji Shishido, Aichi-ken; Makato Kawai, Aichi-ken; Yoshiyuki Okumura, Aichi-ken, all of (JP)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/731,995

(22) Filed: Dec. 7, 2000

Related U.S. Application Data

(60) Provisional application No. 60/170,142, filed on Dec. 10, 1999.

(51) Int. Cl.[7] .................... C07D 401/00; C07D 403/00; C07D 211/68; A61K 31/495; A61K 31/445
(52) U.S. Cl. .............................. 514/253.09; 514/253.1; 514/318; 544/364; 546/194
(58) Field of Search .................. 514/253.09, 253.1, 514/318; 544/364; 546/194

(56) References Cited

U.S. PATENT DOCUMENTS 5,859,025 A * 1/1999 Wagner et al. .............. 514/311

* cited by examiner

*Primary Examiner*—Bruck Kifle
(74) *Attorney, Agent, or Firm*—Peter C. Richardson; Paul H. Ginsburg; Elsa Djuardi

(57) ABSTRACT

This invention provides a compound of the formula (I):

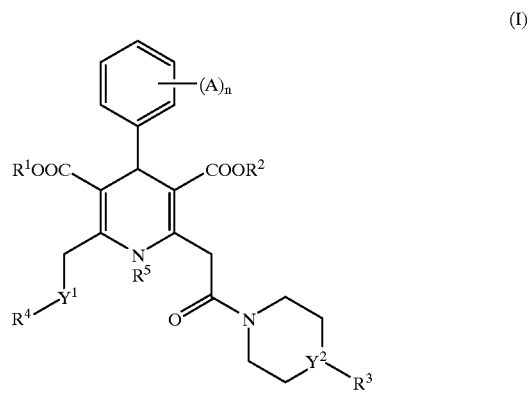

(I)

or the pharmaceutically acceptable salts thereof wherein
A is independently halo; $Y^1$ is $—(CH_2)_m—$, C(O) or S(O);
$Y^2$ is N or CH;
$R^1$ and $R^2$ are independently $C_{1-4}$ alkyl;
$R^3$ is selected from the following:
  (a) optionally substituted $—(CH_2)_p—C_{3-7}$ cycloalkyl;
  (b) optionally substituted $—C_{5-7}$ alkyl; and
  (c) substituted $—C_{1-4}$ alkyl; and
  (d) optionally substituted $C_{7-9}$ bicycloalkyl;
$R^4$ is optionally substituted thiazolyl, imidazolyl or oxazolyl; X is S, —NH, —N—$C_{1-4}$ alkyl or O;
$R^5$ is hydrogen or $C_{1-4}$ alkyl; $R^6$ is $C_{1-4}$ alkyl or halo;
m is 0, 1 or 2; n is 0, 1, 2, 3, 4 or 5; and p is 0, 1, 2, 3, 4, 5 or 6.

These compounds are useful for the treatment of medical conditions caused by bradykinin such as inflammation, cardiovascular disease, pain, etc. This invention also provides a pharmaceutical composition comprising the above compound.

9 Claims, No Drawings

5-MEMBERED HETEROARYL SUBSTITUTED 1,4-DIHYDROPYRIDINE COMPOUNDS AS BRADYKININ ANTAGONISTS

This application claims the benefit of U.S. Provisional Application No. 60/170,142, filed Dec. 10, 1999.

TECHNICAL FIELD

This invention relates to novel 1,4-dihydropyridine compounds. These compounds are useful as antagonists of bradykinin, and are thus useful in the treatment of inflammation, cardiovascular disease or the like in mammalian, especially humans. The present invention also relates to a pharmaceutical composition comprising the above compounds.

BACKGROUND ART

Bradykinin ("BK") is generated under normal conditions in mammalia by the action of various plasma enzymes such as kallikrein on high molecular weight kininogens. It is widely distributed in mammals, as are its two receptor subtypes, $B_1$ and $B_2$. The actions of BK at the $B_2$ receptor include mainly contraction of arterial and venous preparations, although it can cause relaxation of peripheral resistance vessels as well.

Many of the more important functions of BK, such as increases in vascular permeability, pain, and vasodilatation, however, are mediated by the $B_2$ receptor. These effects at the $B_2$ receptor are believed to be responsible for BK's role in numerous diseases, such as inflammation, cardiovascular disease, pain, and the common cold. Hence antagonists at the $B_2$ receptor should find considerable therapeutic applications. Most of the efforts in this area thus far have been directed at peptidic analogues of the BK structure, some of which have been studied as analgesics and antiinflammatory agents.

International Publication Number WO 96/06082 discloses a variety of 1,4-dihydropyridine compounds having a piperazinylcarbonylmethy group at the 2-position, as antagonists of bradykinin.

It would be desirable if there were provided a non-peptide antagonist of the $B_2$ receptor, having an improved $B_2$ antagonistic activity and a good metabolic stability against human liver microsomes.

BRIEF DISCLOSURE OF THE INVENTION

The present invention provides a compound of the following formula:

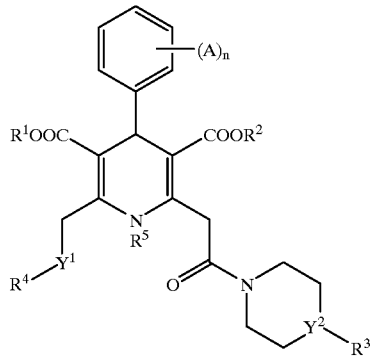

(I)

or the pharmaceutically acceptable salts thereof wherein
A is independently halo;
$Y^1$ is —$(CH_2)_m$—, C(O) or S(O);
$Y^2$ is N or CH;
$R^1$ and $R^2$ are independently $C_{1-4}$ alkyl;
$R^3$ is selected from the following:
(a) —$(CH_2)_p$—$C_{3-7}$ cycloalkyl, the cycloalkyl moiety being optionally substituted with one, two or three substituents selected from cyano, amino-$C_{1-4}$ alkyl-, $C_{1-4}$ alkylamino-$C_{1-4}$ alkyl-, $C_{1-3}$ alkylcarbonylamino-$C_{1-4}$ alkyl-, $C_{1-4}$ alkylsulfonylamino-$C_{1-4}$ alkyl, amino, 2-oxopyrrolidinyl, $C_{4-7}$ cycloalkylamino-$C_{1-4}$ alkyl, di-$C_{1-4}$ alkylamino-$C_{1-4}$ alkyl-, hydroxyl, carbamoyl, $C_{1-3}$ alkylcarbonyl($C_{1-4}$ alkyl)amino, $C_{1-4}$ alkylcarbonyl($C_{1-4}$ alkyl)amino-$C_{1-4}$ alkyl, di-$C_{1-4}$ alkylamino, pyrrolidinyl-$C_{1-4}$ alkyl, 2-oxopyrrolidinyl-$C_{1-4}$ alkyl and di-$C_{1-4}$ alkylamino-$C_{1-4}$ alkyl;
(b) —$C_{5-7}$ alkyl optionally substituted with one or two substituents selected from 2-oxopyrrolidinyl, $C_{1-3}$ alkylsulfonylamino, cyano, $C_{1-3}$ alkylcarbonylamino, 1,1-dioxoisothiazolinyl, 2-oxo-1,3-oxazolidinyl, amino, $C_{1-4}$ alkylamino, morpholinylcarbonyl, morpholino, $C_{1-3}$alkyl-2-oxopyrrolidinyl, piperidinyl and 2-oxo-piperidinyl;
(c) —$C_{1-4}$ alkyl substituted with one or two substituents selected from 2-oxopyrrolidinyl, $C_{1-3}$ alkylsulfonylamino, cyano, $C_{1-3}$ alkylcarbonylamino, 1,1-dioxoisothiazolinyl, 2-oxo-1,3-oxazolidinyl, morpholino, $C_{1-3}$alkyl-2-oxopyrrolidinyl, piperidinyl and 2-oxo-piperidinyl; and
(d) $C_{7-9}$ bicycloalkyl optionally substitued with di-$C_{1-4}$ alkylamino and oxopyrrolidinyl;
$R^4$ is thiazolyl, imidazolyl or oxazolyl, the thiazolyl, imidazolyl or oxazolyl being optionally substituted with one or two substituents independently selected from $C_{1-4}$ alkyl and halo;
X is S, —NH, —N—$C_{1-4}$ alkyl or O;
$R^5$ is hydrogen or $C_{1-4}$ alkyl;
$R^6$ is $C_{1-4}$ alkyl or halo;
m is 0, 1 or 2;
n is 0, 1, 2, 3, 4 or 5; and
p is 0, 1, 2, 3, 4, 5 or 6.
The 1,4-dihydropyridine compounds of this invention have excellent bradykinin antagonistic activity and are thus useful for the treatment of medical conditions caused by bradykinin such as inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, pancreatitis or the like in mammalian, especially humans.

The 1,4-dihydropyridine compounds of this invention have excellent bradykinin antagonistic activity and are thus useful for the treatment of medical conditions caused by bradykinin such as Amyotrophic lateral sclerosis, Huntington's disease, Parkinson's disease, Multiple sclerosis, Stroke, head trauma, Post-surgical brain edema, Brain edema (general), Cytotoxic brain edema (such as that associated with brain tumors, stroke, head trauma, etc.), Brain edema associated with metabolic diseases (renal failure, pediatric metabolic diseases, etc.), Rheumatoid arthritis, Osteoarthritis, Migraine, Neuropathic Pain, Pruritis, Brain Tumor, Pseudotumor cerebri, Glaucoma, Hydrocephalus, Spinal cord trauma, Spinal cord edema, newrogenerative diseases, respiratory diseases, diuresis, natriuresis calciuresis, COPD (chronic obstructive pulmonary disease), post-traumatic brain injury, itching, Sepsis or the like in mammalian, especially humans.

The present invention provides a pharmaceutical composition for the treatment of disease conditions caused by bradykinin, in a mammalian subject, which comprises administering to said subject a therapeutically effective amount of a compound of formula (I).

Further, the present invention also provides a pharmaceutical composition for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, bums, virus infection, head injury, multiple trauma, rhinitis, hepatorenal failure, diabetes, metastasis, pancreatitis or the like, which comprises a therapeutically effective amount of the 1,4-dihydropyridine compound of formula (I) or its pharmaceutically acceptable salt together with a pharmaceutically acceptable carrier.

Further, the present invention also provides a pharmaceutical composition for the treatment of Amyotrophic lateral sclerosis, Huntington's disease, Parkinson's disease, Multiple sclerosis, Stroke, head trauma, Post-surgical brain edema, Brain edema (general), Cytotoxic brain edema (such as that associated with brain tumors, stroke, head trauma, etc.), Brain edema associated with metabolic diseases (renal failure, pediatric metabolic diseases, etc.), Rheumatoid arthritis, Osteoarthritis, Migraine, Neuropathic Pain, Pruritis, Brain Tumor, Pseudotumor cerebri, Glaucoma, Hydrocephalus, Spinal cord trauma, Spinal cord edema, newrogenerative diseases, respiratory diseases, diuresis, natriuresis calciuresis, COPD (chronic obstructive pulmonary disease), post-traumatic brain injury, itching or Sepsis, which comprises a therapeutically effective amount of a compound of formula (I) or its pharmaceutically acceptable carrier.

Also, the present invention provides a pharmaceutical formulation comprising a compound of formula (I), a pharmaceutically acceptable carrier and, optionally, one or more other pharmacologically active ingredients.

Also, the present invention provides a method for the treatment of disease conditions caused by bradykinin, in a mammalian subject, which comprises administering to said subject a therapeutically effective amount of a compound of formula (I).

Further, the present invention provides a method for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, bums, virus infection, head injury, multiple trauma, rhinitis, hepatorenal failure, diabetes, metastasis, pancreatitis or the like, in a mammalian subject, which comprises administering to said subject a therapeutically effective amount of a compound of formula (I).

DETAILED DESCRIPTION OF THE INVENTION

As used herein, the term "halo" is fluoro, chloro, bromo or iodo.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, an example of "$C_{7-9}$ bicycloalkyl" means bicyclo[3.2.1]octyl, octahydropentalenyl, bicyclo[2.2.1] heptyl, and the like.

As used herein, an example of "$C_{3-7}$ cycloalkyl" means cyclopropyl, cyclobutyl, cyclopentyl, cyclohexyl, cycloheptyl, and the like.

Preferred compounds of this invention are those of the formula (I) wherein (A)$_n$ is 2,6-dichloro;

$Y^1$ is —CH$_2$—;

$Y^2$ is N or CH;

$R^1$ and $R^2$ are independently methyl, ethyl or propyl;

$R^3$ is selected from the following:

(a) —(CH$_2$)$_p$—C$_{3-7}$ cycloalkyl, the cycloalkyl moiety being optionally substituted with one, two or three substituents selected from cyano, amino-C$_{1-4}$ alkyl-, C$_{1-4}$ alkylamino-C$_{1-4}$ alkyl-, C$_{1-3}$ alkylcarbonylamino-C$_{1-4}$ alkyl-, C$_{1-4}$ alkylsulfonylamino-C$_{1-4}$ alkyl, amino, 2-oxopyrrolidinyl, C$_{4-7}$ cycloalkylamino-C$_{1-4}$ alkyl, di-C$_{1-4}$ alkylamino-C$_{1-4}$ alkyl-, hydroxyl, carbamoyl, C$_{1-3}$ alkylcarbonyl(C$_{1-4}$ alkyl)amino, C$_{1-4}$ alkylcarbonyl(C$_{1-4}$ alkyl)amino-C$_{1-4}$ alkyl, di-C$_{1-4}$ alkylamino, pyrrolidinyl-C$_{1-4}$ alkyl, 2-oxopyrrolidinyl-C$_{1-4}$ alkyl and di-C$_{1-4}$ alkylamino-C$_{1-4}$ alkyl;

(b) —C$_{5-7}$ alkyl optionally substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, amino, C$_{1-4}$ alkylamino, morpholinylcarbonyl, molipholino, C$_{1-3}$ alkyl-2-oxopyrrolidinyl, piperidinyl and 2-oxo-piperidinyl; and (c) —C$_{1-4}$ alkyl substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, morpholino, C$_{1-3}$ alkyl-2-oxopyrrolidinyl, piperidinyl and 2-oxo-piperidinyl; and (d) C$_{7-9}$ bicycloalkyl optionally substitued with di-C$_{1-4}$ alkylamino or oxopyrrolidinyl;

$R^4$ is 1,3-thiazol-2-yl, 1H-imidazol-2-yl, 1-methyl-1H-imidazol-2-yl, 1-ethyl-1H-imidazol-2-yl or 1,3-oxazol-2-yl;

X is S, -NH or -N-methyl;

$R^5$ is hydrogen;

n is 2; and p is 0, 1, 2, 3, 4, 5 or 6.

Much preferred compounds of this invention are those of the formula (I) wherein $R^1$ and $R^2$ are methyl;

$R^3$ is selected from the following:
- (a) —$(CH_2)_p$—$C_{4-6}$ cycloalkyl, the cycloalkyl moiety being optionally substituted with one or two substituents selected from cyano, amino-$C_{1-4}$ alkyl-, $C_{1-4}$ alkylamino-$C_{1-4}$ alkyl-, $C_{1-3}$ alkylcarbonylamino-$C_{1-4}$ alkyl-, $C_{1-4}$ alkylsulfonylamino-$C_{1-4}$ alkyl, amino, 2-oxopyrrolidinyl, $C_{4-7}$ cycloalkylamino-$C_{1-4}$ alkyl, di-$C_{1-4}$ alkylamino-$C_{1-4}$ alkyl-, hydroxyl, carbamoyl, $C_{1-3}$ alkylcarbonyl($C_{1-4}$ alkyl)amino, $C_{1-4}$ alkylcarbonyl($C_{1-4}$ alkyl)amino-$C_{1-4}$ alkyl, di-$C_{1-4}$ alkylamino, pyrrolidinyl-$C_{1-4}$ alkyl, 2-oxopyrrolidinyl-$C_{1-4}$ alkyl and di-$C_{1-4}$ alkylamino-$C_{1-4}$ alkyl;
- (b) —$C_{5-6}$ alkyl optionally substituted with one or two substituents selected from 2-oxopyrrolidinyl, $C_{1-3}$ alkylsuflonylamino, cyano, $C_{1-3}$ alkylcarbonylamino, 1,1-dioxoisothiazolidinyl, 2-oxo-1,3-oxazolidinyl, amino, $C_{1-4}$ alkylamino, morpholinylcarbonyl, morpholino, $C_{1-3}$alkyl-2-oxopyrrolidinyl, piperidinyl and 2-oxo-piperidinyl;
- (b) —$C_{2-4}$ alkyl substituted with one or two substituents selected from 2-oxopyrrolidinyl, $C_{1-3}$ alkylsuflonylamino, cyano, $C_{1-3}$ alkylcarbonylamino, 1,1-dioxoisothiazolidinyl, 2-oxo-1,3-oxazolidinyl, morpholino, $C_{1-3}$ alkyl-2-oxopyrrolidinyl, piperidinyl and 2-oxo-piperidinyl; and
- (d) bicyclo[3.2.1]octyl optionally substitued with $C_{1-3}$ alkyl-amino or oxopyrrolidinyl;

$R^4$ is 1,3-thiazol-2-yl, 1-methyl-1H-imidazol-2-yl or 1,3-oxazol-2-yl; and p is 0, 1, 2 or 3.

Also, preferred compounds of this invention are those of the formula (I) wherein $R^3$ is selected from the following:
- (a) $(CH_2)_p$—$C_{4-6}$ cycloalkyl, the cycloalkyl moiety being optionally substituted with a substituent selected from cyano, aminomethyl, aminoethyl, ethylaminomethyl, methylaminoethyl, acetylaminomethyl, acetylaminoethyl, ethylcarbonylaminomethyl, methylsulfonylaminomethyl, methylsulfonylaminoethyl, amino, dimethylaminomethyl, dimethylaminoethyl, diethylaminomethyl, diethylaminoethyl, pyrrolidinylmethyl, pyrrolidinylethyl, cyclopentylaminomethyl, cyclopentylaminoethyl, oxopyrrolidinyl, hydroxy, (ethyl)(acetyl)amino, (methyl)(acetyl)amino, (ethyl)(acetyl)aminomethyl, (methyl)(acetyl)aminomethyl, diethylamino, dimethylamino, aminocarbonyl and acetylaminomethyl;
- (b) —$C_{5-6}$ alkyl optionally substituted with a substituent selected from methylsulfonylamino, ethylsulfonylamino, cyano, acetylamino, ethylcarbonylamino, amino, etylamino, methylamino, oxopyrrolidinyl, 1,1-dioxoisothiazolidinyl, 2-oxo-1,3-oxazolidinyl, methyloxopyrrolidinyl, morpholinocarbonyl, morpholino, oxopiperidinyl and piperidinyl;
- (c) —$C_{2-4}$ alkyl substituted with a substituent selected from methylsulfonylamino, ethylsulfonylamino, cyano, acetylamino, ethylcarbonylamino, oxopyrrolidinyl, 1,1-dioxoisothiazolidinyl, 2-oxo-1,3-oxazolidinyl, methyloxopyrrolidinyl, morpholinocarbonyl, morpholino, oxopiperidinyl and piperidinyl; and
- (d) bicyclo[3.2.1]octyl optionally substitued with methylamino, ethylamino or oxopyrrolidinyl.

Preferred individual compounds of this invention are:

dimethyl 2-[2-[4-[(1-cyanocyclohexyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-[[1-(aminomethyl)cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(ethylamino)methyl]cyclohexyl]methyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[[1-[(acetylamino)methyl]cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[[(methylsulfonyl)amino]methyl]cyclohexyl]methyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[(1-aminocyclohexyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(ethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(dimethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(diethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-(1-pyrrolidinylmethyl)cyclopentyl]methyl]-1-piperazinyl]ethyl]-6-[2-(1,3-thiazol-2-yl)ethyl]-1,4-dihydro-3,5-pyridinedicarboxylate;

dimethyl 2-[2-[4-[[1-[(cyclopentylamino)methyl]cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-(8-(diethylamino)bicyclo [3.2.1]oct-3-yl)-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2,2-dimethyl-3-[(methylsulfonyl)amino]propyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[(1-cyanocyclopentyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-(2-cyano-2-methylpropyl)-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-[3-(acetylamino)-2,2-dimethylpropyl]-1-piperazinyl]-2-oxoethyl]-4-(2,6-dichlorophenyl)-6-[2-(1,3-thiazol-2-yl)ethyl]- 1,4-dihydro-3,5-pyridinedicarboxylate;

dimethyl 2-[2-[4-[[1-(aminomethyl)cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-(3-amino-2,2-dimethylpropyl)-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[3-(ethylamino)-2,2-dimethylpropyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-methyl-3-(2-oxo-1-pyrrolidinyl)butyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2,2-dimethyl-3-(2-oxo-1-pyrrolidinyl)propyl]-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[3-(2-oxo-1-pyrrolidinyl)propyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[4-(2-oxo-1-pyrrolidinyl)cyclohexyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-(1,1-dioxoisothiazolinyl)propyl]-1-piperadinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[3-(2-oxo-1,3-oxazolidin-3-yl)propyl]-1-piperadinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-[(2-oxo-1-pyrrolidinyl)methyl]cyclohexyl]methyl-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-[(2-oxo-1-pyrrolidinyl)methylcyclopentyl]methyl-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2-(1-hydroxycyclohexyl)ethyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-(2-methyl-5-oxo-1-pyrrolidinyl)propyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-(3-methyl-2-oxo-1-pyrrolidinyl)propyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[3-[acetyl(ethyl)amino]propyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[-4-[[1-[(acetyl(ethyl)amino)methyl]cyclopentyl]methyl]-1-piperazinyl]-2-oxoethyl]-4-(2,6-dichlorophenyl)-1,4-dihydro-3,5-pyridinedicarboxylate;

dimethyl 4-(2,6-dichlorophenyl)-2-[2-oxo-2-[4-[2-[1-(2-oxo-1-pyrrolidinylicyclopentyl]ethyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2-[1-(diethylamino)cyclopentyl]ethyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-[4-[4-(2-oxo-1-pyrrolidinyl)butyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[4-methyl-4-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[2-[1-[2-oxo-1-pyrrolidinyl)methyl]cyclopentyl]ethyl]-1-piperazinyl]ethyl]-6-[2-(1,3-thiazol-2-yl)ethyl]-1,4-dihydro-3,5-pyridinedicarboxylate;

dimethyl 4-(2,6-Dichlorophenyl)-2-[2-[4-[4-(4-morpholinyl)-4-oxobutyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[4-(4-morpholinyl)butyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-ethyl-3-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2-[1-[(diethylamino)methyl]cyclopentyl]ethyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[4-(2-oxo-1-piperidinyl)butyl]-1-piperazinyl]ethyl]-6-[2-(1,3-thiazol-2-yl)ethyl-1,4-dihydro-3,5-pyridinedicarboxylate;

dimethyl 4-(2,6-dichlorophenyl)-2-[2-oxo-2-[4-[4-(1-piperidinyl)butyl]-1-piperazinyl]ethyl]-6-[2-(1,3-thiazol-2-yl)ethyl]-1,4-dihydro-3,5-pyridinedicarboxylate;

dimethyl 2-[2-[4-[2-[1-(aminocarbonyl)cyclopentyl]ethyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-[1-[(acetylamino)methyl]cyclohexyl]-1-piperidinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[1-[(ethylamino)methyl]cyclohexyl]-1-piperidinyl]-2-oxoethyl]-6-[2-(1,3-thiazol-2-yl)ethyl]-1,4-dihydro-3,5-pyridinedicarboxylate;

dimethyl 2-[2-[4-[[1-(aminomethyl)cyclobutyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(ethylamino)methyl]cyclobutyl]methyl]-1-piperazinyl]-2-oxoethyl]-6-[2-(1,3-thiazol-2-yl)ethyl]-1,4-dihydro-3,5-pyridinedicarboxylate; and dimethyl 4-(2,6-dichlorophenyl)-2-[2-oxo-2-[4-[8-(2-oxo-1-pyrrolidinyl)bicyclo[3.2.1]oct-3-yl]-1-piperazinyl]carbonyl]-6-[2-(1,3-thiazol-2-yl)ethyl]-1,4-dihydro-3,5-pyridinedicarboxylate.

Most preferred individual compounds of this invention are:

dimethyl 2-[2-[4-[[1-(aminomethyl)cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(dimethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(diethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-(1-pyrrolidinylmethyl)cyclopentyl]methyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-methyl-3-(2-oxo-1-pyrrolidinyl)butyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-[(2-oxo-1-pyrrolidinyl)methyl]cyclopentyl]methyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[4-methyl-4-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[1-[(ethylamino)methyl]cyclohexyl]-1-piperidinyl]-2-oxoethyl]-6-[2-(1,3-thiazol-2-yl)ethyl]-1,4-dihydro-3,5-pyridinedicarboxylate; and dimethyl 4-(2,6-dichlorophenyl)-2-[2-oxo-2-[4-[8-(2-oxo-1-pyrrolidinyl)bicyclo[3.2.1]oct-3-yl]-1-piperazinyl]carbonyl]-6-[2-(1,3-thiazol-2-yl)ethyl]-1,4-dihydro-3,5-pyridinedicarboxylate.

General Synthesis

The 1,4-dihydropyridine compounds of formula (I) of this invention may be prepared by a variety of synthetic methods known to those skilled in the art. For example, the 1,4-dihydropyridine compounds of formula (I), may be prepared by reaction of compound (II) with compound (III), followed, if desired, by conversion of a compound (III) in which $R^3$ is H into a compound (III) in which $R^3$ is other than H, as indicated in the following Preparation Method A.

Preparation Method A:

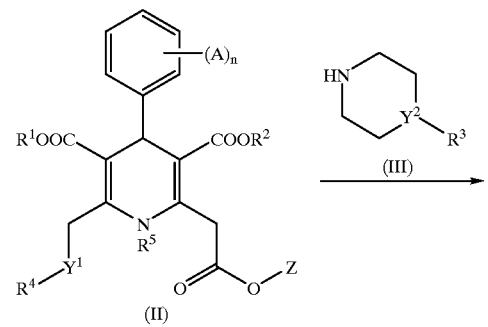

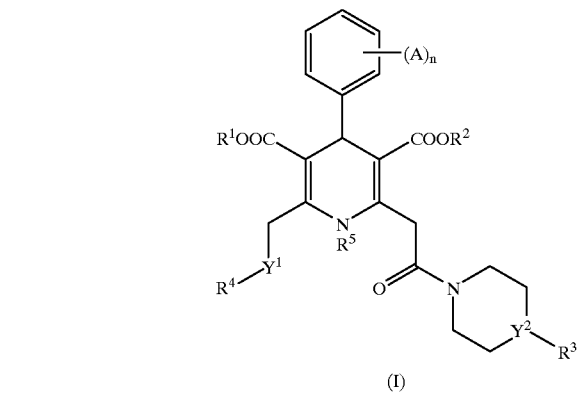

(wherein Z is hydrogen or lower alkyl (e.g., $C_{1-4}$ alkyl) such as methyl and ethyl; and the other symbols are as already defined)

In Preparation Method A, when Z is lower alkyl, the compound (II) may be first subjected to selective saponification of the ester residue at the 2-position of the dihydropyridine ring, followed by acidification to afford a free acid, which is coupled with the compound (III) to give the 1,4-dihydropyridine (I). When Z is H, the compound (II) may be directly coupled with the compound (III) to obtain the 1,4-dihydropyridine (I).

The selective saponification and the acidification may be carried out by conventional procedures. In a typical procedure, the selective saponification is carried out by treatment with sodium hydroxide in a suitable reaction-inert solvent at a temperature in the range from −20 to 40° C., usually from 10° C. to 30° C. for 3 minutes to 4 hours, usually 15 minutes to 1 hour. In a typical procedure, the acidification is carried out by treatment with diluted hydrochloric acid in a suitable reaction-inert solvent such as water at a temperature in the range from 0 to 30° C., usually from 5° C. to 25° C. for 1 minute to 1 hour, usually 5 minutes to 15 minutes.

The 1,4-dihydropyridine (I) can be obtained from the corresponding 1,4-dihydropyridine (II) wherein $R^3$ is H by a coupling reaction between the obtained acid and 4-N-substituted piperazine. The condensation may be carried out in a reaction-inert solvent, such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane) using a coupling agent such as dicyclohexylcarbodiimide (DCC), water soluble carbodiimide (WSC), 2-ethoxy-N-ethoxycarbonyl-1,2-dihydroquinoline, benzotriazol-1-yloxy-tris(dimethylamino)phosphonium hexafluorophosphate (BOP), diethyl azodicarboxylate-triphenylphosphine, diethylcyanophosphonate (DEPC), diphenylphosphorylazide (DPPA) and ethyl chloroformate. This reaction may be carried out at a temperature in the range from −30 to 40° C., usually from 0° C. to 25° C. for 10 minutes to 96 hours, usually 30 minutes to 24 hours.

In addition, when $R^3$ is substituted-alkyl, the 4-N-substituted piperazines (III) as used herein may be either known or may be prepared by known methods. For example, the 4-N-substituted piperazines may be prepared by means of (1) N-alkylation of 1-N-protected piperazine with appropriate alkyl halide, $R^3$-halo, (2) reductive amination of 1-N-protected piperazine with appropriate aldehyde or ketone in the presence of a reducing agent, followed by deprotection of the 1-N-protecting group, or (3) Michael addition of 1-N-protected piperazine with appropriate conjugated ketones, esters or amides, or (4) piperazine ring construction from N-substituted amine. Suitable 1-N-protecting groups include, for example, benzyl, benzyloxycarbonyl and t-butoxycarbonyl group.

The reductive alkylation may be carried out with appropriate aldehyde or ketone in a suitable reaction-inert solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane), in the presence of a suitable reducing agent such as sodium borohydride, sodium cyanoborohydride or sodium triacetoxy borohydride at a temperature in the range from −20 to 120° C., usually 0 to 80° C. for 10 minutes to 1 week, usually 30 minutes to 96 hours, optionally in the presence of molecular sieves. Alternatively, alkylation can be made by two step synthesis. A ketone may be treated with an amine in an inert solvent such as toluene or xylene, at a temperature in the range from, 80 to 130° C., usually 100 to 120° C. for 10 hours to 2 week, usually 1 days to 1 week, preferably 3 to 5 days. The product may be reduced by hydrogenation in the presence of appropriate catalyst such as palladium on carbon and platinum oxide (IV), usually platinum oxide(IV) in an inert solvent such as ethanol and ethyl acetate, usually ethyl acetate, at a temperature in the range from 10 to 60° C., usually 20 to 30° C. for 1 hour to 3 days, usually 3 hours to 10 hours.

Typical Micheal addition reaction may be carried out at a temperature in the range from 30° C. to 120° C., usually from 60° C. to 100° C. for 5 hours to a week, usually 10 hours to 4 days.

Preparation Method B-I:

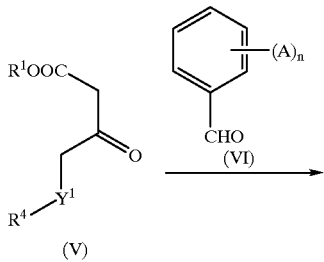

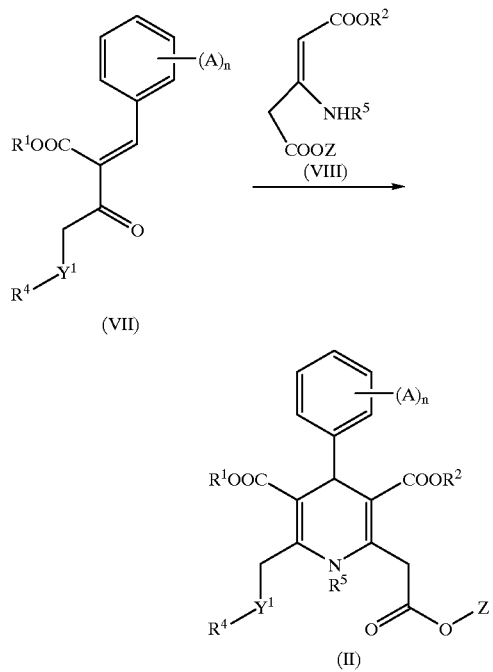

(wherein Z is lower alkyl such as methyl and ethyl; and the other symbols are as already defined)

This method utilizes the modified Hantzsch synthesis as described in A. Sausins and G. Duburs, *Heterocycles,* 1988, 27, 269. In this method, beta-keto ester (V) is first reacted with substituted benzaldehyde (VI) to obtain compound (VII). This reaction may be carried out in a suitable reaction-inert solvent. Suitable solvents include, for example, aromatic hydrocarbons such as benzene, toluene and xylene; alcohols such as methanol, ethanol, propanol and butanol; ethers such as diethyl ether, dioxane and tetrahydrofuran; halogenated hydrocarbons such as methylene dichloride, chloroform and dichloroethane; amides such as N,N-dimethylformamide; and nitrites such as acetonitrile. This reaction may be carried out at a temperature of 0° C. to 200° C., preferably from 80° C. to 120° C. for 30 minutes to 24 hours, preferably 30 minutes to 6 hours. If desired, this reaction may be catalyzed by a base such as piperidine, pyridine or alkoxide, or by an acid catalyst such as acetic acid, $TiCl_4$ or p-toluenesulfonic acid.

Thereafter, the benzylidene (VII) as obtained above is reacted with enamine (VIII) in the presence of, or absence of a suitable condensing agent such as Lewis acids, to obtain the 1,4-dihydropyridine (II). This reaction may be carried out in the presence of, or absence of the reaction-inert solvent as listed above. However, this reaction may preferably carried out in the absence of a solvent. This reaction may be carried out at a temperature of 0° C. to 200° C., preferably, from 60° C. to 150° C. for 30 minutes to 48 hours, preferably 10 hours to 20 hours.

In addition, the beta-keto esters (V) which can be used herein may be prepared by known methods as shown in, for example: (1) *J. Labelled Compds. Radiopharm.,* 1989, 27, 599; (2) *J. Org. Chem.,* 1989, 54, 3258; (3) *J. Am. Chem. Soc.,* 1974, 96, 1082; (4) *J. C. S. Perkin I,* 1979, 529; (5) *Synthesis,* 1986, 37; (6) *J. C. S. Chem. Commun.,* 1977, 932, (7) *Angew. Chem. Int. Ed. Engl.,* 1979, 18, 72 and (8) *Tetrahedron Lett.,* 1983, 24, 5425. The benzaldehydes (VI) which can be used herein may be either already known or may be prepared according to the reported methods.

Preparation Method B-II:

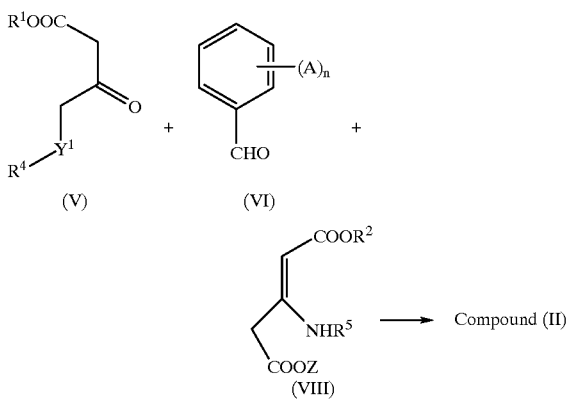

(wherein all the symbols are as already defined)

This method utilizes the three components Hantzsch reaction. In a typical procedure, the beta-keto ester (V), the substituted benzealdehyde (VI) and the enamine (VII) may be heated together in a suitable reaction-inert solvent as listed above (preferably lower alkanols such as methanol and ethanol). Preferably, a small amount of a lower alkanoic acid such as acetic acid is added as catalyst. The reaction mixture may be heated at 80° C. to 200° C., preferably from 100° C. to 140° C. for 30 minutes to 1 week, usually 24 hours to 96 hours.

Preparation Method B-III

Compounds of formula (VIII) may be prepared by a process of this invention according to Scheme B-III.

Scheme B-III

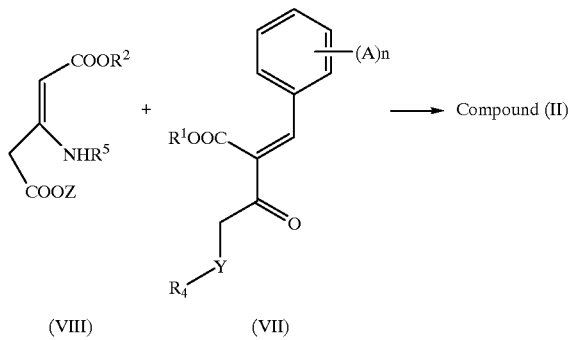

Scheme B-III exemplifies a process of this invention for preparing a compound of formula (II) comprising step (a): addition of an, enamine compound of formula (VIII) to an alkylene compound of formula (VII) followed by step (b) acid catalyzed cyclization reaction of the resulting compound in step (a).

The former addition step (a) may be carried out under conditions applied to nucleophilic addition reactions using a suitable base in a reaction inert solvent. More preferably, the reaction may be carried out under conditions commonly used in Michael-type addition. Preferred bases for this reaction are those used in Michael-type reactions. Examples of the preferred bases include alkylmagnesium halides known as Grignard reagents and halomagnesium alkoxides. More preferred bases include ($C_1$–$C_6$)alkylmagnesium bromide and tert-butoxy-magnesium bromide. Preferred solvents used in this reaction include ($C_1$–$C_4$)alkanol, tetrahydrofuran (THF), diethyl ether, dioxane, hexane, toluene, 1,2-dimethoxy ethane (DME) and the like. This reaction may be carried out at a temperature from about –150° C. to reflux, preferably from about –100° to 100° C. In view of convenience, this reaction may be carried out at about room temperature using, for example, halomagnesium($C_1$–$C_4$) alkoxides, ($C_1$–$C_6$)alkylmagnesiumhalides, metalhydrides, metal($C_1$–$C_3$)alkoxides, magnesium-di[($C_1$–$C_3$)alkoxides], metal-n-butoxide, metal-sec-butoxide, metal-tert-butoxide or a metalcarbonate such as $K_2CO_3$. In case of the base is $K_2CO_3$, the reaction is effectively run in THF. In case of the base is CsF or KF, the reaction is effectively run in THF or methanol (MeOH) at an elevated temperature such as at about 60° C. In case of using butyllithium (BuLi), the reaction is effectively run in THF at from about –78° to about –30° C. In case of using halomagnesium($C_1$–$C_4$) alkoxides or ($C_1$–$C_6$)alkylmagnesiumhalides, a preferred solvent is THF. Suitable reaction time ranges from about 3 minutes to about 2 days, preferably from about 30 minutes to about 40 hours.

The subsequent cyclization process step (b) may be carried out in the presence of a protonic acid. Suitable protonic acids include ($C_1$–$C_6$)alkanoic acid such as acetic acid, hydrochloric acid (HCl) and sulfonic acids such as p-toluenesulfonic acid. It is preferred to add a non-protonic Lewis acid to the reaction mixture in combination with the protonic acid, when the base used in Step (a) is other than magnesium (VIII) bases. This reaction may be carried out at a temperature from about –150° C. to reflux, preferably from about –100° to 100° C. The reaction time ranges from about 1 second to 5 days, preferably 5 minutes to 20 houres.

Generally, those reactions illustrated in Scheme B-Ill may be carried out at about –78° C. using dry-ice/acetone or dry-ice/methanol, about 0° C. using an ice-bath, room temperature or 100° C., preferably at about 0° C. or about room temperature.

The reaction steps (a) and (b) are performed in the same reaction vessel under mild conditions with high-yield.

An enamine compound of formula (VIII) may be prepared according to procedures known to those skilled in the art, such as those illustrated in Scheme B-III-a.

Scheme B-III-a

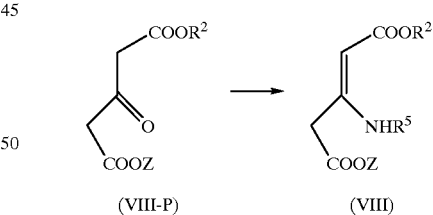

Typically, a beta-keto ester compound of formula (VIII-P) may be transformed to a compound of formula (VIII) wherein $R^2$, $R^5$ and Z are defined as above. This reduction may be carried out in a reaction inert solvent resolving ammonia gas at a temperature in the range of from about 0° to 60° C. Suitable reaction inert solvents include lower alkanols such as methanol and ethanol. Alternatively, an ammonia gas containing solution given above may be added to a solution containing a beta-keto ester (VIII-P). The mixture is reacted at a temperature in the range of from about 0° to 60° C. to yield the enamine compound (VIII).

An alkylene compound of formula (VII) may be prepared according to procedures known to those skilled in the art.

Scheme B-III-b illustrates one embodiment of the preparation process.

Scheme B-III-b

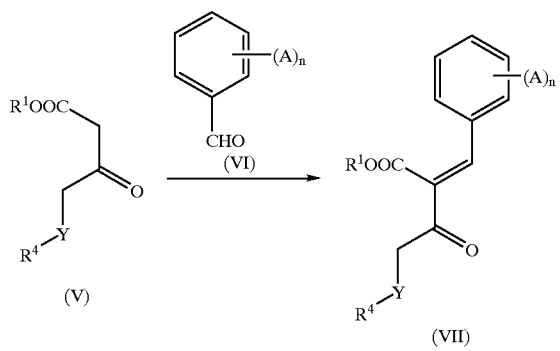

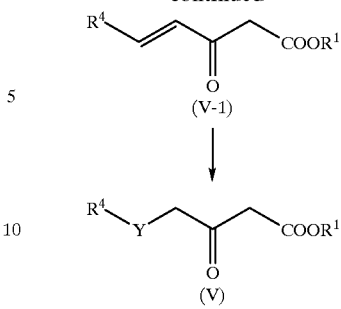

(V-1)

↓

(V)

An aldehyde compound (V-3), wherein $R^4$ is defined as above, is reacted with malonic acid under a basic condition. For example, this reaction may be carried out in the presence of a weak base such as piperidine in a reaction inert solvent such as pyridine to give a carboxylic acid compound of formula (V-2). The compound (V-2) thus obtained may be subjected to an aliphatic nucleophilic substitution reaction in the presence of a coupling agent to give a pentenoate compound of formula (V-1). This reaction may conveniently be carried out first by treating the compound of formula (V-1) with a coupling agent such as N,N'-carbonyldiimidazole in a reaction inert solvent such as dimethylformamide, then reacting with a neuclephilic reagent such as $CH_3O_2CCH_2K$ in the presence of a Lewis acid such as magnesium chloride. The former treatment may be carried out at a temperature in the range of from about 0° to 60° C., preferably at about room temperature for from about 1 minutes to 12 hours. The latter reaction may be carried out at the temperature in the range of from about 0° to 100° C., preferably from about room temperature to 60° C. for from about 1 minutes to 12 hours. The compound of formula (V-1) may be reduced over a metal catalyst under hydrogen atmosphere to give the compound of formula (V) according to a known procedure. Suitable catalysts are such as Raney nickel catalyst and a noble metal catalysts including palladium on carbon and palladium hydroxide. This reaction may be carried out in a reaction inert solvent such as methanol, at about room temperature under hydrogen at an appropriate pressure for example using a balloon, for about 1 minutes to 12 hours.

A carbonyl compound of formula (V) may be subjected to a coupling reaction with an aldehyde compound of formula (VI) to give the alkylene compound of formula (VII) according to a known procedure. For example, a compound of formula (V) may be reacted with a compound of formula (VI) according to a procedure reported by L. Tietze et al. Liebigs Ann. Chem., pp. 321–329, 1988. This reaction may be carried out in a suitable reaction inert-solvent for example an aromatic hydrocarbon such as benzene, toluene and xylene, an alcohol such as methanol, ethanol, propanol and butanol, an ether such as diethyl ether, dioxane and tetrahydrofuran (THF), a halogenated hydrocarbon such as methylene dichloride, chloroform and dichloroethane, an amide such as N,N-dimethylformamide, and a nitrile such as acetonitrile. This reaction may be carried out at a temperature in the range of from about 0° C. to the reflux temperature of the reaction mixture, preferably from about 80° to the 120° C. for from about 30 minutes to 24 hours, preferably from 30 minutes to 6 hours. This reaction may conveniently be carried in the presence of a base or acid catalyst. Suitable base catalysts are such as piperidine, pyridine and alkoxide, and suitable acid catalysts are such as acetic acid, $TiCl_4$ and p-toluenesulfonic acid.

An intermediate compound of formula (V) may be prepared starting from a known compound according to a procedure known to those skilled in the art. For example, a compound of formula (V) may be prepared according to the procedure described in Scheme B-III-c.

A ketone compound of formula (V) and a substituted benzaldehyde compound of formula (VI) may also be prepared according to known procedures (e.g., (1) D. Scherling, *J. Labelled Compds. Radiopharm.,* Vol. 27, pp. 599-, 1989, (2) C. R. Holmquist et al., *J. Org. Chem.,* Vol. 54, pp. 3528-, 1989, (3) S. N. Huckin et al., *J. Am. Chem. Soc.,* Vol. 96, pp. 1082-, 1974, (4) *J. C. S. Perkin I,* pp. 529-, 1979, (5) *Synthesis* pp. 37, 1986, and (6) *J. C. S. Chem. Commun.,* pp. 932-, 1977).

Scheme B-III-c

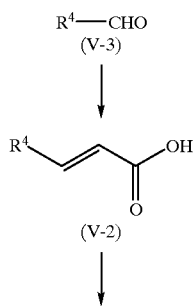

Preparation Method B-IV:

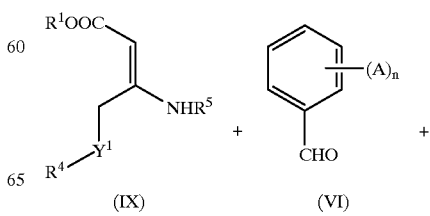

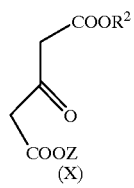

Compound (II)

(wherein all the symbols are as already defined)

This method also utilizes the three components Hantzsch reaction as mentioned above. The reaction conditions similar to the above can be also used in this method.

The enamine (IX) may either be known compounds or may be prepared by known methods. For example, the enamine (IX) may be prepared by reacting the beta-keto ester (V) with ammonia. More specifically, the beta-keto ester (V) may be dissolved in a suitable solvent as listed above. Excess amount of ammonia gas is introduced into the solution at a temperature of 0 to 60° C. Alternatively, a solution containing ammonia dissolved in the above solvent is added to the solution-containing the beta-keto ester (V), and the resultant mixture is reacted at a temperature of 0 to 60° C., to obtain the enamine (IX).

The compounds of formula (I), and the intermediates above-mentioned preparation methods can be isolated and purified by conventional procedures, such as recrystallization or chromatographic purification.

General Synthesis of the optical active 1,4-dihydropyridine

The optically active compounds of this invention can be prepared by several methods. For example, the optically active compounds of this invention may be obtained by chromatographic separation or fractional crystallization from the final compounds or the intermediates in racemic form thereof. Alternatively, the optically active compounds may be prepared by optically selective reaction, enzymatic hydrolysis or reactions using optically active intermediates.

For example, the optically active 1,4-dihydropyridine (I-o) may be prepared by reaction of the compound (II-o) with the compound (III), followed, if desired, by conversion of the compound (III) in which $R^3$ is H into the compound (III) in which $R^3$ is other than H, as indicated in the following Preparation Method A-o.

Preparation Method A-o:

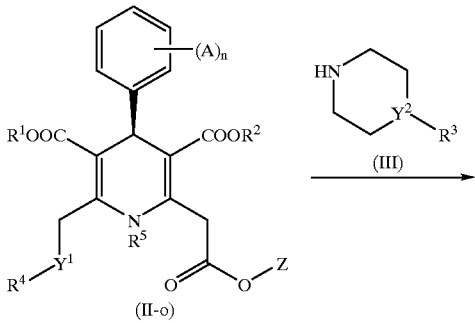

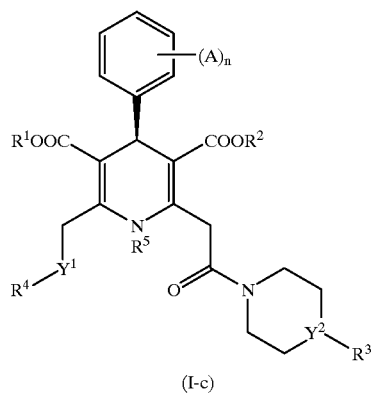

(wherein Z is hydrogen or lower alkyl (e.g., $C_{1-4}$ alkyl) such as methyl and ethyl; and the other symbols are as already defined)

In Preparation Method A-I, when Z is lower alkyl, the compound (II-o) may be first subjected to selective saponification of the ester residue at the 2-position of the dihydropyridine ring, followed by acidification to afford a free acid, which is coupled with the compound (III) to give the 1,4-dihydropyridine (I-o). When Z is H, the compound (II-o) may be directly coupled with the compound (III) to obtain the 1,4-dihydropyridine (I-o).

The selective saponification and the acidification may be carried out by conventional procedures. In a typical procedure, the selective saponification is carried out by treatment with sodium hydroxide in a suitable reaction-inert solvent at a temperature in the range from −20 to 40° C., usually from 10° C. to 30° C. for 3 minutes to 4 hours, usually 15 minutes to 1 hour. In a typical procedure, the acidification is carried out by treatment with diluted hydrochloric acid in a suitable reaction-inert solvent such as water at a temperature in the range from 0 to 30° C., usually from 5° C. to 25° C. for 1 minute to 1 hour, usually 5 minutes to 15 minutes.

A compound (I-o) can be obtained from the corresponding compound (II-o) wherein $R^3$ is H by a coupling reaction between the obtained acid and 4-N-substituted piperazine. The condensation may be carried out in a reaction-inert solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane) using a coupling agent such as dicyclohexylcarbodiimide (DCC), water soluble carbodiimide (WSC), 2-ethoxy-N-ethoxycarbonyl-1,2-dihydroquinoline, benzotriazol-1-yloxy-tris(dimethylamino) phosphonium hexafluorophosphate (BOP), diethyl azodicarboxylate-triphenylphosphine, diethylcyanophosphonate (DEPC), diphenylphosphorylazide (DPPA) and ethyl chloroformate. This reaction may be carried out at a temperature in the range from −30 to 40° C., usually from 0° C. to 25° C. for 10 minutes to 96 hours, usually 30 minutes to 24 hours.

In addition, when $R^3$ is substituted-alkyl, the 4-N-substituted piperazines (III) as used herein may be either known or may be prepared by known methods. For example, the 4-N-substituted piperazines may be prepared by means of (1) N alkylation of 4-N-protected piperazine with appropriate alkyl halide, $R^3$-halo, (2) reductive amination of 4-N-protected piperazine with appropriate aldehyde or ketone in the presence of a reducing agent, followed by deprotection of the amino-protecting group, or (3) Michael addition of 4-N-protected piperazine with appropriate conjugated ketone, ester or amide, or (4) piperazine ring construction from N-substituted amine. Suitable amino-protecting groups include, for example, benzyl, benzyloxycarbonyl and t-butoxycarbonyl group.

The reductive alkylation may be carried out with appropriate aldehyde or ketone in a suitable reaction-inert solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane), in the presence of a suitable reducing agent such as sodium borohydride, sodium cyanoborohydride or sodium triacetoxyborohydride at a temperature in the range from −20 to 120° C., usually 0 to 80° C. for 10 minutes to 1 week, usually 30 minutes to 96 hours, optionally in the presence of molecular sieves. Alternatively, alkylation can be made by two step synthesis. A ketone may be treated with an amine in an inert solvent such as toluene or xylene, at a temperature in the range from 80 to 130° C., usually 100 to 120° C. for 10 hours to 2 week, usually 1 days to 1 week, preferably 3 to 5 days. The product may be reduced by hydrogenation in the presence of appropriate catalyst such as Palladium on carbon and platinum oxide (IV), usually platinum oxide in an inert solvent such as ethanol and ethyl acetate, usually ethyl acetate, at a temperature in the range from 10 to 60 ° C., usually 20 to 30° C. for 1 hour to 3 days, usually 3 hours to 10 hours.

Typical Micheal addition reaction may be carried out at a temperature in the range from 30° C. to 120° C., usually from 60° C. to 100° C. for 5 hours to a week, usually 10 hours to 4 days.

The optically active intermediates of formula (II) can be prepared by the following methods.

Preparation Method B-I-o (Fractional Crystallization):

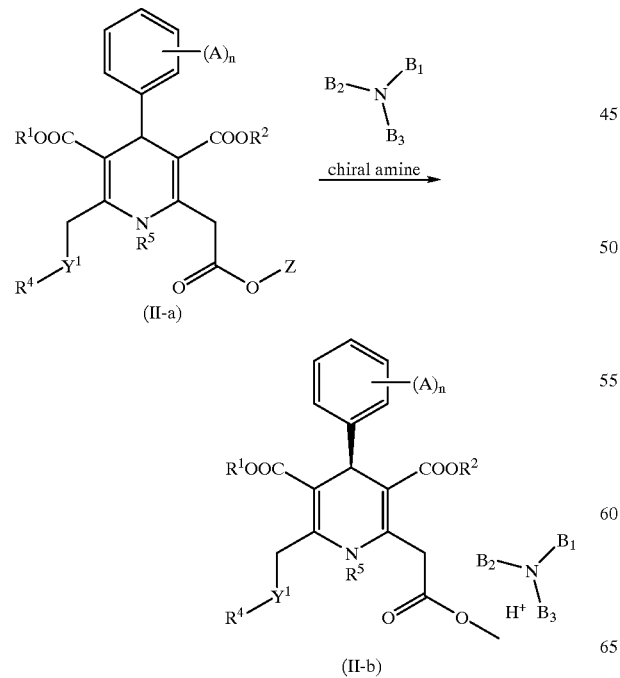

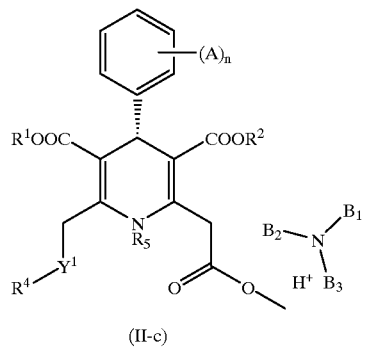

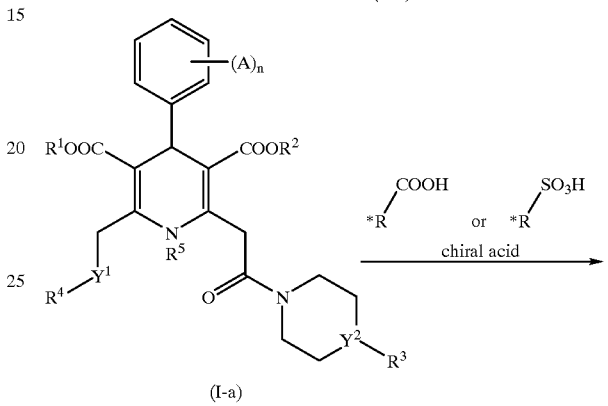

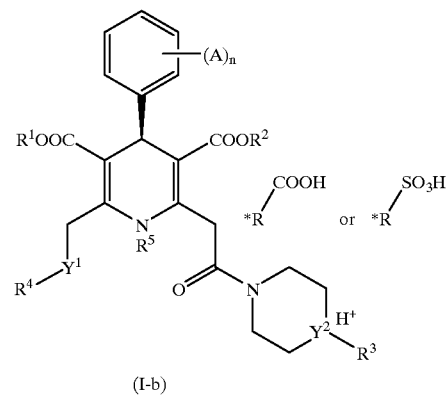

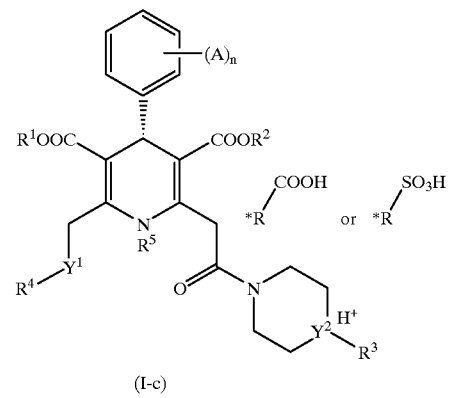

(wherein [$B^1$ $B^2$ $B^3$]$NH^+$ is a chiral amine residue; Z is hydrogen; R*COOH and R*$SO_3$H are chiral acids and the other symbols are already defined.)

In this method, an acid compound (II-a) may be subjected to a fractional crystallization with a chiral amine such as cinchonidine, cinchonine, quinine, burcine and phenethylamine or their derivatives, amino acids to obtain an amine salt (II-b). This reaction may be conducted in an organic solvent, preferably a pure or mixed alcoholic solvent selected from methanol, ethanol, 2-propanol and mixture thereof. The resulted salt may be further purified by several times recrystallization. The pure salt thus obtained may be converted to the corresponding carboxylic acid (an enantiomer of compound (II) wherein Z is H) by a partition between organic solvent such as ethyl acetate or dichloromethane and acid solution such as diluted hydrochloric acid followed by concentration. On the other hand, the salt of the antipode contained in the resulted mother liquid may be converted to the corresponding carboxylic acid (an enantiomer of compound (II) wherein Z is H) by the same procedure descried above after concentration of the mother liquid. This acid may be further purified by crystallization in organic or inorganic solvents to give the antipode. This crystallization of the acid may be performed several times, if necessary, to improve its optical purity.

Furthermore, a final compound (I-a) may be resolved into each salt of both enantiomers by the same procedure described above using chiral acids such as tartaric acid and camphorsulfonic acids or their derivatives. The resolved salts thus obtained may be converted to the corresponding amines (each enantiomer of I-a) by a partition between organic solvent such as dichloromethane and basic solution such as aqueous sodium hydrogencarbonate or sodium hydroxide.

Preparation Method B-II-o (Enzymatic Hydrolysis):

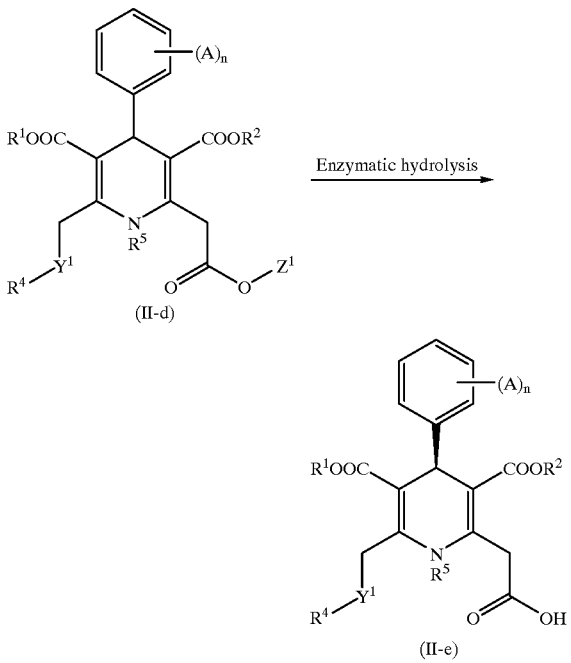

(wherein $Z^1$ is, for example, an acyloxymethyl group; and the other symbols are already defined.)

In this method, an ester compound (II-d) is subjected to enzymatic hydrolysis to obtain an optically active carboxylic acid (II-e) (Compound (II) wherein Z is H). Application of Lipase in 1,4-dihydropyridine for enantioselective hydrolysis is known in literature such as H. Ebiike, et. al., Tetrahedron Letters, 32, 5805 (1991). Suitable $Z^1$ groups may include acyloxymethyl groups such as pivaloyloxymethyl and propionyloxymethyl. The enzymatic hydrolysis may be carried out in an aqueous organic solvent, preferably a water saturated ethereal solution such as isopropyl ether, t-butyl methyl ether or diethyl ether. This reaction may be carried out at a temperature from 0° C. to 60° C., preferably from 30° C. to 45° C. for 10 minutes to 4 weeks, preferably 1 days to 2 weeks.

Preparation Method B-IV-o (enantioselective Hantzsch cyclization)

The compound (II) may be obtained using enantioselective Hantzsch cyclization. This cyclization may be made by a condensation with either enone or enamine attached chiral auxiliaries or by condensation of the enone (VII) and the enamine (VIII) in the presence of chiral catalyst. The main literature (Tetrahedron .Lett,(1988),6437) precedent for this process involves the Enders SAMP/RAMP-methodology (chiral hydrazone tautomer of enamine). Other variants exists in the patent (Bayer's DE 87/3714438 and DE 84/3423105) involving a chiral enamine formed from t-butylvaline.

The 1,4-dihydropyridine compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The present invention includes salt forms of the compounds (I) as obtained above.

Insofar as the 1,4-dihydropyridine compounds of this invention are basic compounds, they are capable of forming a wide variety of different salts with various inorganic and organic acids.

The acids which are used to prepare the pharmaceutically acceptable acid addition salts of the aforementioned 1,4dihydropyridine base compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate). The acid addition salts can be prepared by conventional procedures.

The 1,4-dihydropyridine compounds of the present invention of formula (I) exhibit significant bradykinin receptor-binding activity and therefore, are of value in the treatment of a wide variety of clinical conditions in mammals, especially human. Such conditions include inflammation, cardiovascular disease, pain, common cold, allergies, asthma, pancreatitis, bums, virus infection, head injury, multiple trauma and the like.

Therefore, these compounds are readily adapted to therapeutic use as bradykinin antagonists for the control and/or treatment of any of the aforesaid clinical conditions in mammals, including humans.

Also, the compounds of formula (I) are co-administered with $H_1$-antagonist.

Further, the present invention also encompasses a pharmaceutical composition for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, cystitis, pancreatitis, Amyotrophic lateral sclerosis, Huntington's disease, Parkinson's disease, Multiple sclerosis, Stroke, head trauma, Post-surgical brain edema, Brain edema (general), Cytotoxic brain edema (such as that associated with brain tumors, stroke, head trauma, etc.), Brain edema associated with metabolic diseases (renal failure, pediatric metabolic diseases, etc.), Rheumatoid arthritis, Osteoarthritis, Migraine, Neuropathic Pain, Pruritis, Brain Tumor, Pseudotumor cerebri, Glaucoma, Hydrocephalus, Spinal cord trauma, Spinal cord edema, newrogenerative diseases, respiratory diseases, diuresis, natriuresis calciuresis, COPD (chronic obstructive pulmonary disease), post-traumatic brain injury, itching, Sepsis or the like, which comprises a therapeutically effective amount of the 1,4-dihydropyridine compound of formula (I) or its pharmaceutically acceptable salt together with a pharmaceutically acceptable carrier and H1-antagonist.

The compounds of the invention may advantageously be employed in combination with one or more other therapeutic ingredients selected from an antibiotic, anti-fungal, or anti-viral agent, an anti-histamine, a non-steroidal anti-inflammatory drug or disease modifying anti-rheumatic drug.

The combination with an anti-histamine ($H_1$ antagonist) is particularly favoured for use in the prophylaxis and treatment of asthma. Examples of anti-histamine are chlorpheniramine, brompheniramine, clemastine, ketotifen, azatadine, loratadine, terfenadine, cetirizine, astemizole, tazifylline, levocabastine, diphenhydramine, temelastine, etolotifen, acrivastine, azelastine, ebastine, mequitazine, KA-398, FK-613, mizolastine, MDL-103896, levocetirizine, mometasone furoate, DF-1111301, KC-11404, carebastine, ramatroban, desloratadine, noberastine, selenotifen, alinastine, E-4716, efletirizine, tritoqualine, norastemizole, ZCR-2060, WY-49051, KAA-276, VUF-K-9015, tagorizine, KC-11425, epinastine, MDL-28163 terfenadine, HSR-609, acrivastine and BMY-25368.

Method For Assessing Biological Activities

The activity of the 1,4-dihydropyridine compounds of the present invention, as bradykinin antagonists, is determined by their ability to inhibit the binding of bradykinin at its receptor sites in recombinant human bradykinin $B_2$ receptor expressing CHO-K1 cells (from Receptor Biology, Inc.) employing radioactive ligands.

The bradykinin antagonist activity of the 1,4-dihydropyridine compounds is evaluated by using the standard assay procedure described in, for example, Baenziger N. L., Jong Y-J. I., Yocum S. A., Dalemar L. R., Wilhelm B., Vaurek R., Stewart J. M., *Eur. J. Cell Biol.*, 1992, 58, 71–80. This method essentially involves determining the concentration of the individual compound required to reduce the amount of radiolabelled bradykinin ligands by 50% at their receptor sites in CHO-K1 cells, thereby affording characteristic $IC_{50}$ values for each compound tested.

More specifically, the assay is carried out as follows. First, rat, guinea pig or monkey ileum tissues are minced and suspended in 25 mM piperazine-N,N'-bis (2-ethanesulfonic acid (PIPES) buffer (pH 6.8) containing 0.1 mg/ml of soybean trypsin inhibitor. Then, the tissues are homogenized using a Polytron homogenizer at setting 7 for 30 seconds three times, and then rehomogenized with a Teflon-coated homogenizer. The homogenized suspension was centrifuged at 1,200×g for 15 minutes. The pellet was rehomogenized and then centrifuged at 1,200×g for 15 minutes. These supernatant were centrifuged at 10,000×g for 60 minutes. The tissue pellets, CHO-K1 cell membrane are suspended in 25 mM PIPES buffer (pH 6.8) containing 1.25 mM dithiothreitol, 1.75 µg/ml bacitracin, 1 mM o-phenanthroline, 18.75 µM captopril, 1.25 mg/ml bovine serum albumin (BSA), to prepare tissue/cell suspensions. Then, 10 µl of test compound solution dissolved in phosphate buffered saline (PBS, pH 7.5) containing 2% DMSO (final) and 0.1% BSA (w/v) or 10 ml of 12.5 mM bradykinin in PBS (pH 7.5) containing 0.1% BSA (w/v) are placed in a reaction 96-well plate. 15 µl of 8.3 nM [3H]bradykinin is added to the compound solution or bradykinin solution in the 96-well plate. Finally 100 µl of the tissue or cell suspension are added to the mixture in the plate, and incubated at room temperature for 1 hour under the dark. After incubation, the resultant product in the reaction plates is filtered through 0.1% polyethylenimine presoaked LKB filermat. The filtrate is washed using a Skatron auto cell harvester. The tissue bound radioactivity is determined using a LKB betaplate counter. The $IC_{50}$ value is determined using the equation:

$$\text{Bound} = B_{max}/(1+[I]/IC_{50})$$

wherein [I] means the concentration of the test compound.

All compounds prepared in the working examples as described below were tested by this method, and showed an $IC_{50}$ value of 1 nM to 50 nM in CHO-K1 cells with respect to inhibition of binding at its receptor.

The bradykinin antagonist activity of the 1,4-dihydropyridine compounds in vivo is evaluated by a plasma leakage test. This test essentially involve determining the concentration of the individual compound required to reduce by 50% the amount of bradykinin-induced plasma leakage in rat urinary bladder, thereby affording characteristic $ED_{50}$ values for each compounds tested.

More specifically, the assay is carried out as follows. 3.5-week old male Sprague-Dawlew rats are purchased from Charles River Japan Inc. The rats are fed on stock diet (CRF from Charles River Japan, Inc.) and maintained under the standard conditions (temperature, 23±1° C. and humidity 55±5%) for at least 3 days. The rats are fasted overnight prior to the experiments. Each test group consists of 5 rats.

Bradykinin, purchased from Peptide Ins., is dissolved in the physiological saline (0.9% sodium chloride) at a concentration of 10 nmol/ml. The test 1,4-dihydropyridine compounds are dissolved or suspended at different concentrations in the physiological saline solution containing 10 mg/ml Evans blue (Wako Pure Chemical, Japan).

Captopril (5 mg/kg of body weight) is intraperitoneally (i.p.) injected to the rats, and 20 minutes later the rats are anesthetized by an administration of Nembutal (Abbott) (2.5 mg/kg of body weight). 5 minutes later, the test compound solution containing Evans blue is intravenously (i.v.) injected to the rats at a dose of 3 ml/kg of body weight. Another 5 minutes later, bradykinin is i.v. injected at a dose of 10 nmol/kg body weight. Thereafter, the rats are killed by dislocation of the neck and the urinary bladders are obtained. The urinary bladders are individually treated with 1 ml of formamide at 60° C. for at least 16 hours to extract Evans blue from the tissue. The absorbency of the extract is measured spectrophotometrically at 605 nm to determine the dye concentration. The effect of the individual test compound is calculated as a percentage of the amount of Evans blue leaked into the urinary bladder as compared to the control (saline for the test compounds). Some compounds prepared in the working examples as described below exhibited a remarkable activity at a concentration of 0.2 mg/kg in the inhibition of urinary bladder leakage in this test system.

Human liver microsome assay $T_{1/2}$ value against human liver microsome was calculated by conventional procedure. More specifically, human liver microsomes (0.2 mg/ml) were mixed with 1 μM of kinin B2 antagonist and incubated with in the presence of 1.3 mM NADP+, 0.9 mM NADH, 3.3 mM glucose-6-phosphate, 3.3 mM MgCl$_2$, and glucose-6-phosphate dehydrogenase (8 units/ml) in a total volume of 1.2 ml of 100 mM potassium phosphate buffer, pH 7.4, at 37° C. At specified incubation times (0, 5, 10, 30 minutes), an aliquot of 100 μl was withdrawn from the reaction mixture and mixed with 1 ml of acetonitrile containing internal standard. Protein was precipitated by centrifugation at 1,800×g for 10 minutes, and the resulting supernatant was taken.

Kinin B2 antagonist in samples were analyzed by LS/MS/MS, in a Sciex API-300 mass spectrometer linked with a Hawlett-Pakkered HP1100 HPLC system. A sample of 20 μl was injected to the HPLC system equipped with a Wakosil II 5C18 HG column (2.0×150 mm). The mobile phase consisted of 80% acetonitorile including 10 mM ammonium acetate, and the elution was isocratic with a flow rate of 0.3 ml/min. Part of the eluent from the HPLC column was introduced into the atmospheric ionization source via an ion spray interface. $T_{1/2}$ value is determined using the equation:

$$T_{1/2}=0.693/k$$

wherein k is elimination rate constant of the test compound.

The compounds of the formula (I) exhibit excellent biological activity in vitro and in vivo as bradykinin antagonists. Additionally, the compound of the formula (I) was more stable against metabolism compared to structurally related 1,4-dihydropiridine disclosed in WO 96/06082 in human liver microsomes assay experiments. The most preferred compounds as memtined above of Working Examples showed $T_{1/2}$ values of more than 20 minutes.

The 1,4-dihydropyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc. are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex® DU3050 (Amino Type, 30~50 μm). Low-resolution mass spectral data (EI) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.).

Chemical symbols have their usual meanings; b.p. (boiling point), m.p. (melting point), l (liter(s)), ml (milliliter(s)), g (gram(s)), mg(milligram(s)), mol (moles), mmol (millimoles), eq. (equivalent(s)).

Example 1

Dimethyl 2-[2-[4-[(1-cyanocyclohexyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate A. methyl 3-oxo-5-(1,3-thiazole-2-yl)-4-pentenoate Methyl 3-oxo-5-(1,3-thiazole-2-yl)-4-pentenoate was prepared from 3-(1,3-thazol-2-yl)-2-propenoic acid (*Bull. Chem. Soc. Jap.* 1974, 47, 151.) according to the literature procedure (*Heterocycles* 1994, 38, 751.). To a stirred solution of 3-(1,3-thiazol-2-yl)-2-propenoic acid (100.0 g, 644.4 mmol) in DMF (1000 ml) was added 1,1'-carbonyldiimidazole (115.0 g, 708.9 mmol) in small portions. After stirring at room temperature for 5 hours, to the reaction mixture were added anhydrous magnesium chloride (73.6 g, 773.0 mmol) and monomethyl malonate potassium salt (120.8 g, 773.0 mmol). The resulting suspension was heated at 55° C. with stirring for 14 h. After cooling to room temperature, the reaction mixture was poured into 1500 ml of 2 N HCl, and extracted with a mixture of EtOAc (1500 ml) and toluene (500 ml). The organic phase was separated and the aqueous phase was extracted with a 3:1 mixture of EtOAc and toluene (2000 ml). The combined organic phase was washed with $H_2O$ (1000 ml) and brine (1000 ml), dried ($Na_2SO_4$) and evaporated to afford 132.0 g of methyl 3-oxo-5-(1,3-thiazole-2-yl)-4-pentenoate (1/2 of keto/enol form)

$^1$H NMR (CDCl$_3$) δ: 11.77 (s, 2/3H), 7.97 (d, J=3.1 Hz, 1/3H), 7.90 (d, J=3.1 Hz, 2/3H), 7.72 (d, J=16.0 Hz, 1/3H), 7.55 (d, J=15.6 Hz, 2/3H), 7.51 (d, J=3.1 Hz, 1/3H), 7.39 (d, J=3.1 Hz, 2/3H), 7.06 (d, J=16.0 Hz, 1/3H), 6.80 (d, J=15.6 Hz, 2/3H), 5.28 (s, 2/3H), 3.79 (s, 3×2/3 H), 3.77 (s, 3×1/3H), 3.45 (s, 2×1/3H).

B. Methyl 3-oxo-5-(1,3-thiazole-2-yl)pentanoate

A mixture of methyl 3-oxo-5-(1,3-thiazole-2-yl)-4-pentenoate (132.0 g) and palladium hydroxide, 20 wt % on carbon (13 g) in MeOH (2600 ml) was stirred under hydrogen atmosphere by balloon for 4 hours. Catalyst was removed by filtration and the filtrate evaporated to give 130.0 g of methyl 3-oxo-5-(1,3-thiazole-2-yl)pentanoate as a brown liquid.

$^1$H NMR (CDCl$_3$) δ: 7.65 (d, J=3.3 Hz, 1H), 7.20 (d, J=3.3 Hz, 1H), 3.73 (s, 3H), 3.53 (s, 2H), 3.33 (t, J=6.9Hz, 2H), 3.13 (t, J=6.9 Hz, 2H).

C. Methyl 3-(2,6-dichlorophenyl)-2-[(1,3-thiazol-2-yl)propanoyl]-2-propenoate

To a solution of methyl 3-oxo-5-(1,3-thiazole-2-yl)pentanoate (130 g) in toluene (600 ml) were added 2,6-dichlorobenzaldehyde (113.0 g, 644 mmol), acetic acid (5 ml) and piperidine (5 ml). This mixture was distilled for removal of the initial distillate (about 100 ml) then replaced the distillation apparatus to Dean-Stark trap and heated under reflux temperature with azeotropic removal of $H_2O$ for 4 hours. The mixture was washed with $H_2O$ (200 ml) and brine (200 ml), dried ($Na_2SO_4$) and evaporated to give a crude mixture. This was purified by column chromatography on silica gel (1800 g, hexane/EtOAc=3/1 as eluent) to afford 165.3 g (69%, 3 steps) of methyl 3-(2,6-dichlorophenyl)-2-[1,3-thiazol-2yl)propanoyl]-2-propenoate as a brown oil This is a 1:1 mixture of the double bond isomers.

$^1$H NMR (CDCl$_3$) δ: 7.70–7.15 (m, 6H), 3.91 and 3.66 (apparently two synglets, 3H), 3.44 and 3.28 (apparently two synglets, 4H).

D. Dimethyl 4-(2,6-dichlorophenyl)-2-(2-methoxy-2-oxoethyl)-6-2-(1,3-thiazol-2-yl)ethyl]-1,4-dihydropyridine-3,5-dicarboxylate To a stirred solution of 2-methyl-2-propanol (92.8 g, 1252 mmol; 2.1 eq.) in anhydrous THF (1100 ml) was added a 1.0 M solution of EtMgBr in THF (1192 ml, 1192 mmol; 2.0 eq.) dropwise slowly at 0° C. under nitrogen atmosphere for 2 hours period. The resulting solution was stirred at room temperature for 1 hour. Then to the mixture was added a solution of dimethyl 3-amino-2-pentenedioate (113.5 g, 655 mmol; 1.1 eq.) in anhydrous THF (550 ml) dropwise slowly at 0° C. for 20 minutes. The resulting pale yellow solution was stirred at the same temperature for 1 h, then a solution of methyl 3-(2,6-dichlorophenyl)-2-[(1,3-thiazol-2-yl)propanoyl]-2-propenoate (219.9 g, 594 mmol; 1.0 eq.) in anhydrous THF (550 ml) was added at 0° C. for 30 minutes. The reaction mixture was stirred at room temperature for 16 hours under nitrogen atmosphere, then acetic acid (170 ml; 5.0 eq.) was added at 0° C. The resulting mixture was stirred at room temperature for 6 hours. The mixture was poured into 2 NNaOHaq. (1000 ml), the organic phase was separated and the aqueous phase was extracted with EtOAc (2000 ml). The combined organic phase was washed with $H_2O$ (1000 ml) and brine (1000 ml), dried ($Na_2SO_4$) and concentrated to give a crude mixture. Purification on silica gel column chromatography (3 times 1700 g) eluted with hexane/EtOAc (2/1 to 1/2) to afford 246.0 g (85%) of dimethyl 4-(2,6-dichlorophenyl)-2-(2-methoxy-2-oxoethyl)-6-[2-(1,3-thiazol-2-yl)ethyl]-1,4-dihydropyridine-3,5-dicarboxylate as a brown oil $^1$H NMR (CDCl$_3$) δ: 8.33 (s, 1H), 7.67 (d, J=3.3 Hz, 1H), 7.24 (t, J=8.0 Hz, 2H), 7.24 (d, J=3.3 Hz, 1H), 6.98 (dd, J=8.0, 8.0 Hz, 1H), 5.99 (s, 1H), 3.86–3.65 (m, 5H), 3.51 (s, 3H), 3.54 (s, 3H), 3.45–3.25 (m, 3H), 3.14–2.96 (m, 1H).

E. 2-[4-(2,6-Dichlorophenyl)-3,5-bis(methoxycarbonyl)-6-[2-(1,3-thiazol-2-yl)ethyl]-1,4-dihydro-2-pyridinyl]acetic acid To a stirred solution of dimethyl 4-(2,6-dichlorophenyl)-2-(2-methoxy-2-oxoethyl)-6-[2-(1,3-thiazol-2-yl)ethyl]-1,4-dihydropyridine-3,5-dicarboxylate (264.0 g, 502.5 mmol) in MeOH (1800 ml) was added 2 N NaOHaq. (630 ml,1260 mmol) dropwise with ice cooling. The reaction mixture was stirred at room temperature for 2 hours. The mixture was acidified with 2 N HCl (700 ml) with ice cooling. The whole mixture was extracted with $CH_2Cl_2$ (600 ml×4), the organic layers were washed with brine (1000 ml), dried (NaSO$_4$) and then evaporated to give 267 g of yellow solids. The solids were recrystallized from 2-propanol to afford 206.5 g (80%) of 2-[4-(2,6-dichlorophenyl)-3,5-bis(methoxycarbonyl)-6-[2-(1,3-thiazol-2-yl)ethyl]-1,4-dihydro-2-pyridinyl]acetic acid as yellow solids.

$^1$H NMR (CDCl$_3$) δ: 8.54 (br.s, 1H), 7.72 (d, J=3.3 Hz, 1H), 7.31–7.15 (m, 3H), 7.01 (dd, J=8.0, 8.0 Hz, 1H), 6.00 (s, 1H), 3.76–3.20 (m, 5H), 3.59 (s, 3H), 3.56 (s, 3H), 3.04–2.90 (m, 1H).

F. 3-(4-Benzyl-1-piperazinyl)propanenitrile

A mixture of acrylonitrile (5.6 ml/85.1 mmol) and benzylpiperazine (5.0 g/28.3 mmol) in benzene (28 ml) was refluxed for 10 hours. After cooling down, the mixture was concentrated in vacuo and the residue was purified by column chromatography (NH$_2$ gel/200–350 mesh/100 g/dichloromethane) to give a pale brown oil (5.5 g/85%).

$^1$H NMR (CDCl$_3$) δ 7.35–7.20 (m, 5H), 3.51 (s, 2H), 2.58–2.42 (m, 12H) ppm.

G. 1-[(4-Benzyl-1-piperazinyl)methyl]cyclohexanecarbonitrile

To a solution of 1-[(4-benzyl-1-piperazinyl)methyl] ethanecarbonitrile (9.0 g/39.3 mmol) in tetrahydrofuran (300 ml) was added dropwise 2.0 M solution of lithium diisopropylamide (98 ml/197 mmol) at −78° C., and then the resulting mixture was stirred for 30 minutes. 1,5-Dibromopentane (8 ml/59 mmol) was added to the mixture in one portion and the resulting mixture was allowed to warm to ambient temperature. The mixture was stirred for 3 hours. Then, H$_2$O (150 ml) was added for quenching. The mixture was extracted with ethyl acetate (200 ml×2). The combined extracts were washed with brine (50 ml), dried over magnesium sulfate, filtered and concentrated in vacuo. The residue was purified by column chromatography (Si, 230–400 mesh/150 g/dichloromethane:methanol= 100:0–100:4) to give a brown solid (11 g/94%).
$^1$H NMR (CDCl3) δ 7.34–7.20 (m, 5H), 3.50 (s, 2H), 2.70–2.60 (m, 4H), 2.50–2.40 (m, 6H), 2.40–1.00 (m, 10H) ppm.

H. 1-(1-Piperazinylmethyl)cyclohexanecarbonitrile

A suspension of 1-[(4-benzyl-1-piperazinyl)methyl] cyclohexanecarbonitrile (2.23 g/7.51 mmol) and Pd(OH)$_2$-C (1.1 g) in methanol (40 ml) was stirred under H$_2$ (4 Kg/cm$^-$$_2$) for 6 hours. After filtration through a pad of Celite, the filtrate was concentrated and the resulting residue was purified by column chromatography to give a white solid (1.1 g/71%).
$^1$H NMR (CDCl$_3$) δ 2.92–2.82 (m, 4H), 2.65–2.55 (m, 4H), 2.43 (s, 2H), 2.06–1.94 (m, 2H), 1.82–1.50 (m, 6H), 1.30–1.06 (m, 3H) ppm.

I. Dimethyl 2-[2-[4-[(1-cyanocyclohexyl)methyl]-1-piperazinyl]-2-oxoethyl]4-(2,6-dichlorophenyl)-6-[2-(1,3-thiazol-2-yl)ethyl]-1,4-dihydro-3,5-pyridinedicarboxylate To a suspension of 2-[4-(2,6-dichlorophenyl)-3,5-bis (methoxycarbonyl)-6-[2-(1,3-thiazol-2-yl)ethyl]-1,4-dihydro-2-pyridinyl]acetic acid (511 mg/1.0 mmol) in dichloromethane (5 ml) was added water soluble carbodiimide (288 mg/1.5 mmol) followed by 1-(1-piperazinylmethyl)cyclohexanecarbonitrile (311 mg/1.5 mmol) at ambient temperature, and then the resulting solution was stirred overnight. The solution was diluted with dichloromethane (100 ml) and the resulting solution was washed with water (10 ml) and brine (10 ml) succesively. The solution was dried over magnesium sulfate, filtered and concentrated. The residue was purified by colum chromatography (NH$_2$ gel/20 g/dichloromethane as eluent) to give a brown amorphous (731 mg/quant.).

Free base
$^1$H-NMR (CDCl3) δ 8.29 (br s, 1H), 7.72 (d, J=3.3 Hz, 1H), 7.24 (d, J=7.9 Hz, 2H), 7.21 (d, J=3.5 Hz, 1H), 7.00 (t, J=8.2 Hz, 1H), 5.99 (s ,1H), 4.09 (d, J=15.0 Hz, 1H), 3.80 (d, J=15.1 Hz, 1H), 3.55 (s, 3H), 3.53 (s, 3H), 3.70–3.50 (m, 5H), 3.40–3.26 (m, 2H), 3.07–2.95 (m, 1H), 2.72–2.56 (m, 4H), 2.47 (s, 2H), 2.20–1.00 (m, 10H) ppm. HCl salt mp 211–213° C. (dec.) IR (KBr)ν$_{max}$: 3568, 3547, 3198, 3094, 3003, 2940, 1684, 1624, 1508, 1435, 1296, 1190, 1103 cm$^{-1}$.
$^1$H-NMR (DMSO-d$_6$) δ 9.22 (br s, 1H), 7.61 (d, J=3.5 Hz, 1H), 7.50 (d, J=3.3 Hz, 1H), 7.24 (d, J=8.2 Hz, 2H), 7.05 (t, J=7.4 Hz, 1H), 5.75 (s, 1H), 4.02 (d, J=15.1 Hz, 1H), 3.50–3.22 (m, 21H), 2.00–1.00 (m, 10H) ppm. MS (m/z) 700 (M+H)$^+$, 698(M–H)$^-$ Example 2

Dimethyl 2-[2-[4-[[1-(aminomethyl)cyclohexyl] methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate A. [1-[(4-Benzyl-1-piperazinyl)methyl]cyclohexyl] methanamine A suspension of 1-[(4-benzyl-1-piperazinyl)methyl] cyclohexanecarbonitrile (3.2 g/10.8 mmol) and LAH (1.6 g/43.2 mmol) in tetrahydrofuran (100 ml) was refluxed for 3 h. After cooling down, the excess reagent was quenched with water saturated diethylether and the resulting gray suspension was stirred until the suspension turned to white suspension. The resulting suspension was filtered through a pad of Celite. The filtrate was dried over magnesium sulfate, filtered and concentrated in vacuo to give a crude (3.2 g/quant.). MS(m/z) 301(M$^+$)

A. tert-Butyl[1-[(4-benzyl-1-piperazinyl)methyl] cyclohexyl]methylcarbamate

A mixture of the resulting crude, di-tert-butyl dicarbonate (3.2 ml/15.9 mmol) and triethylamine (4.4 ml/31.8 mmol) in dichloromethane (50 ml) was stirred overnight. The mixture was diluted with dichloromethane (200 ml), and then the mixture was washed with water (50 ml) and brine (50 ml) successively. The separated organic layer was dried over magnesium sulfate, filtered and concentrated in vacuo. The residue was purified by column chromatography (Si/ 230–400 mesh/dichloromethane:methanol= 100:0–100:1–100:2) to give a pale brown oil (3.0 g/70%).
$^1$H NMR (CDCl$_3$) δ 7.34–7.20 (m, 5H), 6.96–6.85 (m, 1H), 3.48 (s, 2H), 3.12 (d, J=4.8 Hz, 2H), 3.62–2.38 (m, 8H), 2.26 (s, 2H), 1.45 (s, 9H), 1.72–1.14 (m, 10H) ppm.

C. tert-Butyl[1-(1-piperazinylmethyl)cyclohexyl] methylcarbamate

This compound was prepared by a procedure similar to that described in example 1-C as a yellow oil.
$^1$H NMR (CDCl$_3$) δ 6.83–6.72 (m, 1H), 3.48 (s, 1H), 3.13 (d, J=5.1 Hz, 2H), 2.92–2.82 (m, 4H), 2.56–2.42 (m, 4H), 2.24 (s, 2H), 1.82–1.70 (m, 2H), 1.44 (s, 9H), 1.50–1.12 (m, 8H) ppm.

D. Dimethyl 2-[2-[4-[1-[[(tert-butoxycarbonyl)amino] methyl]cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a yellow solid.
$^1$H NMR (CDCl$_3$) δ 8.33 (br s, 1H), 7.72 (d, J=3.3 Hz, 1H), 7.24 (d, J=7.9 Hz, 2H), 7.21 (d, J=3.5 Hz, 1H), 7.00 (t, J=8.4 Hz, 1H), 6.14 (br s, 1H), 5.99 (s, 1H), 4.08 (br s, J=14.8 Hz, 1H), 3.81 (d, J=15.1 Hz, 1H), 3.70–3.55 (m, 6H), 3.55 (s, 3H), 3.53 (s, 3H), 3.40–3.25 (m, 2H), 3.20–2.95 (m, 2H), 2.60–2.42 (m, 4H), 2.26 (s, 2H), 1.50–1.00 (m, 10H), 1.43 (s, 9H) ppm.

E. Dimethyl 2-[2-[4-[[1-(aminomethyl)cyclohexyl]methyl]-1-piperazinyl]-2-oxoethyl]-4-(2,6-dichlorophenyl)-6-[2-(1, 3-thiazol-2-yl)ethyl]-1,4-dihydro3,5-pyridinedicarboxylate A solution of dimethyl 2-[2-[4-[1-[[(tert-butoxycarbonyl) amino]methyl]cyclohexyl]methyl]-1-piperazinyl]-2-oxoethyl]-4-(2,6-dichlorophenyl)-6-[2-(1,3-thiazol-2-yl) ethyl]-1,4-dihydro-3,5-pyridinedicarboxylate (1.8 g/2.2 mmol) in 2 N HCl-acetone (6 ml, 12 ml) was heated at 70° C. for 6 hours. After cooling down, the solution was basified with sat. NaHCO$_3$ and extracted with dichloromethane (100 ml×2). The combined extracts were washed with brine (20 ml), dried over magnesium sulfate, filtered and concentrated in vacuo. The residue was purified by column chromatography (NH$_2$ gel/200–350 mesh/50 g/dichloromethane:methanol=100:0–100:1-100:2–100:5) to give a yellow gum (1.3 g/84%).

Free base
$^1$H-NMR (CDCl$_3$) δ 8.34 (br s, 1H), 7.72 (d, J=3.3 Hz, 1H), 7.24 (d, J=8.6 Hz, 2H), 7.20 (d, J=3.3 Hz, 1H), 7.00 (t, J=7.6 Hz, 1H), 5.99 (s, 1H), 4.05 (d, J=15.5 Hz, 1H), 3.83 (d, J=15.0 Hz, 1H), 3.64–3.48 (m, 5H), 3.55 (s, 3H), 3.53 (s, 3H), 3.40–3.26 (m, 3H), 2.65 (br s, 2H), 2.56–2.45 (m, 4H), 2.25 (s, 2H), 1.68–1.18 (m, 12H) ppm. HCl salt mp 206–210° C. (dec.) IR (KBr)ν$_{max}$: 3404, 2945, 1685, 1624, 1508, 1434, 1296, 1188 cm$^{-1}$.
$^1$H-NMR (DMSO-d$_6$) δ 8.05 (br s, 1H), 7.62 (br d, J=3.3 Hz, 1H), 7.51 (br d, J=3.3 Hz, 1H), 7.24 (d, J=8.2 Hz, 2H), 7.05 (t, J=8.6 Hz, 1H), 5.75 (s, 1H), 4.20–2.60 (m, 18H), 1.60–1.20 (m, 10H) ppm.
MS (m/z): 704 (M+H)$^+$, 702 (M–H)$^-$

Example 3

Dimethyl 4-(2,6-dichlorophenyl)-2-[2-[4-[[1-[(ethylamino)methyl]cyclohexyl]methyl]-1-piperazinyl]-2-oxoethyl]-6-[2-(1,3-thiazol-2-yl)ethyl]-1,4-dihydro-3,5-pyridinedicarboxylate A. tert-Butyl[1-[(4-benzyl-1-piperazinyl)methyl]cyclohexyl]methyl(ethyl)carbamate To a solution of tert-butyl[1-[(4-benzyl-1-piperazinyl)methyl]cyclohexyl]methylcarbamate (770 mg/1.92 mmol) in dimethylformamide (10 ml) was added potassium hydride (157 mg/3.84 mmol) at 0° C. and the resulting solution was stirred for 30 minutes at the same temperature. Ethyliodide (0.46 ml/5.76 mmol) was added to the solution and the resulting mixture was stirred for 6 hours at ambient temperature Water (20 ml) was added for quenching and the mixture was extracted with ethyl acetate (100 ml). The extract was washed with brine (20 ml), dried over magnesium sulfate, filtered and concentrated in vacuo. The residue was purified by column chromatography (Si/230–400 mesh/20 g/dichloromethane:methanol= 100:0–100:2–100:4–100:6) to give a colorless oil (730 mg/89%).
$^1$H NMR (CDCl$_3$) δ 7.35–7.23 (m, 5H), 3.49 (s, 2H), 3.23 (m, 2H), 3.15 (s, 2H), 2.57–2.37 (m, 8H), 2.24 (s, 2H), 1.66–1.57 (m, 4H), 1.45 (s, 9H), 1.50–1.13 (m, 6H), 1.08 (t, J=6.9 Hz, 3H) ppm.

B. tert-Butyl ethyl[[1-(1-piperazinylmethyl)cyclohexyl]methyl]carbamate

This compound was prepared by a procedure similar to that described in example 1-C as a colorless oil.
$^1$H NMR (CDCl$_3$) δ 3.30–3.16 (m, 2H), 3.16 (s, 2H), 2.92–2.82 (m, 4H), 2.52–2.43 (m, 4H), 2.22 (s, 2H), 1.94–1.83 (m, 2H), 1.46 (s, 9H), 1.50–1.00 (m, 8H), 1.09 (t, J=6.9 Hz, 3H) ppm.

C. Dimethyl 2-[2-[4-[1-[[(tert-butoxycarbonyl)(ethyl)amino]methyl]cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a yellow oil.
$^1$H NMR (CDCl$_3$) δ 8.35 (br s, 1H), 7.72 (d, J=3.6 Hz, 1H), 7.27–7.23 (m, 2H), 7.20 (d, J=3.5 Hz, 1H), 6.99 (t, J=7.9 Hz, 1H), 5.99 (s, 1H), 4.14 (d, J=16.0 Hz, 1H), 3.83 (d, J=14.8 Hz, 1H), 3.55 (s, 3H), 3.53 (s, 3H), 3.70–3.50 (m, 4H), 3.58–3.15 (m, 6H), 2.33 (s, 2H), 2.53–2.44 (m, 4H), 2.26 (s, 2H), 1.68–1.40 (m, 10H), 1.46 (s, 9H), 1.86 (t, J=6.8 Hz, 3H) ppm.

D. Dimethyl 4-(2,6-dichlorophenyl)-2-[2-[4-[[1-[(ethylamino)methyl]cyclohexyl]methyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 2-E as a yellow oil.
free base
$^1$H NMR (CDCl$_3$) δ 8.40 (br s, 1H), 7.71 (d, 3.3 Hz, 1H), 7.24 (d, J=8.2 Hz, 2H), 7.20 (d, J=3.5 Hz, 1H), 7.00 (t, J=8.6 Hz, 1H), 5.99 (s, 1H), 4.02 (d, J=15.1 Hz, 1H), 3.85 (d, J=15.1 Hz, 1H), 3.65–3.50 (m, 3H), 3.55 (s, 3H), 3.53 (s, 3H), 3.40–3.26 (m, 3H), 3.10–2.96 (m, 1H), 2.60 (q, J=7.1 Hz, 2H), 2.55–2.45 (m, 6H), 2.28 (s, 2H), 1.55–1.20 (m, 11H), 1.09 (t, J=7.3 Hz, 3H) ppm. HCl salt
mp 206–210° C. (dec.)
IR (KBr)ν$_{max}$: 3371, 2943, 1693, 1647, 1624, 1508, 1435, 1291, 1188, 1153 cm$^{-1}$
$^1$H NMR (DMSO-d$_6$) δ 7.70–7.60 (m, 1H), 7.60–7.50 (m), 7.24 (br d, J=7.7 Hz, 2H), 7.04 (br t, J=8.0 Hz, 1H), 5.75 (s, 1H), 4.20–2.70 (m, 20H), 1.80–1.00 (m, 13H) ppm.
MS (m/z): 732 (M+H)$^+$, 630(M–H)$^-$

Example 4

Dimethyl 2-[2-[4-[[1-[(acetylamino)methyl]cyclohexyl]methyl]-1-piperazinyl]-2-oxoethyl]-4-(2,6dichlorophenyl)-6-[2-(1,3-thiazol-2-yl)ethyl]-1,4-dihydro-3,5-pyridinedicarboxylate A mixture of dimethyl 2-[2-[4-[[1-(aminomethyl)cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate dihydrochloride (230 mg/0.28 mmol), acetic anhydride (0.2 ml/2.1 mmol) and triethylamine (0.5 ml/3.5 mmol) in dichloromethane (5.0 ml) was stirred for 5 hours at ambient temperature. The mixture was diluted with dichloromethane (50 ml), and then washed with water (10 ml) and brine (10 ml) successively. The organic layer was dried over magnesium sulfate, filtered and concentrated in vacuo. The residue was purified by column chromatography (NH$_2$ gel/200–350 mesh/20 g/dichloromethane) to give a yellow film (110 mg/53%).
$^1$H NMR (CDCl$_3$) δ 8.25 (br s, 1H), 7.75–7.65 (m, 1H), 7.72 (d, J=3.3 Hz, 1H), 7.24 (d, J=8.4 Hz, 2H), 7.21 (d, J=3.5 Hz, 1H), 7.01 (t, J=8.2 Hz, 1H), 6.00 (s, 1H), 4.17 (d, J=14.8 Hz, 1H), 3.74 (d, J=14.7 Hz, 1H), 3.74–3.55 (m, 4H), 3.55 (s, 3H), 3.54 (s, 3H), 3.40–3.20 (m, 5H), 3.12–2.94 (m, 1H), 2.64–2.44 (m, 4H), 2.33 (s, 2H), 1.98 (s, 3H), 1.56–1.16 (m, 10H) ppm.
MS (m/z): 746 (M+H)$^+$, 644 (M–H)$^-$

Example 5

Dimethyl 4-(2,6-dichlorophenyl)-2-[2-[4-[[1-[[(methylsulfonyl)amino]methyl]cyclohexyl]methyl]-1-piperazinyl]-2-oxoethyl]-6-[2-(1,3-thiazol-2-yl)ethyl]-1,4-dihydro-3,5-pyridinedicarboxylate A mixture of dimethyl 2-[2-[4-[[1-(aminomethyl)cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate dihydrochloride (230 mg/0.28 mmol) methansulfonylchloride (0.2 ml/2.5 mmol) and triethylamine (0.5 ml/3.5 mmol) in dichloromethane (5.0 ml) was stirred for 5 hours at ambient temperature. The mixture was diluted with dichloromethane (50 ml), and then washed with water (10 ml) and brine (10 ml) successively. The organic layer was dried over magnesium sulfate, filtered and concentrated in vacuo. The residue was purified by column chromatography (NH$_2$ gel/200–350 mesh/20 g/dichloromethane) to give a yellow film (122 mg/55%).
free base
$^1$H NMR (CDCl$_3$) δ 8.28 (br s, 1H), 7.71 (d, J=3.3 Hz, 1H), 7.50–7.30 (m, 1H), 7.25 (d, J=9.7 Hz, 2H), 7.21 (d, J=3.5 Hz, 1H), 7.00 (t, J=7.7 Hz, 1H), 5.99 (s, 1H), 3.99 (d, J=15.0 Hz, 1H), 3.85 (d, J=15.0 Hz, 1H), 3.70–3.50 (m, 4H), 3.55 (s, 3H), 3.51 (s, 3H), 3.40–3.25 (m, 3H), 3.12 (s, 2H), 3.06–2.94 (m, 1H), 2.92 (s, 3H), 2.62–2.48 (m, 4H), 2.26 (s, 2H), 1.88–1.18 (m, 10H) ppm.

HCl salt
mp 200–210° C. (dec.)
IR (KBr)$v_{max}$: 3371, 2943, 1693, 1647, 1624, 1508, 1435, 1296, 1188, 1153, 1103 cm$^{-1}$.
$^1$H-NMR (DMSO-d$_6$) δ 8.05 (br s, 1H), 7.62 (br d, J=3.3 Hz, 1H), 7.51 (br d, J=3.3 Hz, 1H), 7.24 (d, J=8.2 Hz, 2H), 7.05 (t, J=8.6 Hz, 1H), 5.75 (s, 1H), 4.20–2.60 (m, 21H), 1.60–1.20 (m, 10H) ppm.
MS (m/z): 700 (M+H)$^+$, 698 (M–H)$^-$ Example 6

Dimethyl 2-[2-[4-[(1-aminocyclohexyl)methyl]-1-piperazinyl]-2-oxoethyl]4-(2,6-dichlorophenyl)-6-[2-(1,3-thiazol-2-yl)ethyl]-1,4-dihydro-3,5-pyridinedicarboxylate A. tert-Butyl 1-[(4-benzyl-1-piperazinyl)carbonyl]cyclohexylcarbamate This compound was prepared by a procedure similar to that described in example 1-D and 2-A, B, C and D as a yellow oil.
$^1$H-NMR (CDCl$_3$) δ 7.37–7.20 (m, 5H), 4.77 (br s, 1H), 3.80–3.60 (m, 4H), 3.54–3.42 (m, 2H), 2.48–2.30 (m, 4H), 2.00–1.20 (m, 10H), 1.43 (s, 9H) ppm.

B. tert-Butyl 1-(1-piperazinylmethyl)cyclohexylcarbamate

This compound was prepared by a procedure similar to that described in example 1-C as a yellow oil.
$^1$H-NMR (CDCl$_3$) δ 4.46 (br s, 1H), 2.90–2.78 (m, 4H), 2.56–1.20 (m, 20H), 1.42 (s, 9H) ppm.

C. Dimethyl 2-[2-[4-[(1-aminocyclohexyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a yellow solid.
Free base
$^1$H-NMR (CDCl$_3$) δ 8.35 (br s, 1H), 7.72 (d, J=3.3 Hz, 1H), 7.25 (d, J=8.2 Hz, 2H), 7.20 (d, J=3.3 Hz, 1H), 7.00 (t, J=7.4 Hz, 1H), 5.99 (s ,1H), 4.05 (d, J=15.1 Hz, 1H), 3.83 (d, J=15.0 Hz, 1H), 3.70–3.50 (m, 4H), 3.55 (s, 3H), 3.53 (s, 3H), 3.40–3.24 (m, 3H), 3.10–2.94 (m, 1H), 2.64–2.48 (m, 4H), 2.57 (s, 2H), 1.84–1.70 (m, 4H), 1.60–1.20 (m, 8H) ppm.
HCl salt
mp 210–220° C. (dec.)
IR (KBr)$v_{max}$: 3389, 3213, 2947, 1693, 1622, 1508, 1435, 1296, 1190 cm$^{-1}$
$^1$H-NMR (DMSO-d$_6$) δ 7.63 (d, J=3.5 Hz, 1H), 7.53 (d, J=3.3 Hz, 1H), 7.24 (d, J=8.2 Hz, 2H), 7.05 (t, J=7.5 Hz, 1H), 4.00–2.50 (m, 16H), 1.84–1.20 (m, 10H) ppm.
MS (m/z): 690 (M+H)$^+$.

Example 7

Dimethyl 4-(2,6-dichlorophenyl)-2-[2-[4-[[1-[(ethylamino)methyl]cyclopentyl]methyl]-1-piperazinyl]-2-oxoethyl]-6-2-(1,3-thiazol-2-yl)ethyl]-1,4-dihydro-3,5-pyridinedicarboxylate A. tert-Butyl ethyl[[1-(1-piperazinylmethyl)cyclopentyl]methyl]carbamate This compound was prepared by a procedure similar to that described in example 3-A as a colorless oil.
$^1$H NMR (CDCl$_3$) δ 3.40–3.25 (m, 2H), 3.20 (s, 2H), 2.90–2.75 (m, 4H), 2.50–2.30 (m, 4H), 2.35 (s, 1H), 2.21 (s, 2H), 1.75–1.15 (m, 8H), 1.46 (s, 9H), 1.08 (t, J=6.9 Hz, 3H) ppm.

B. tert-Butyl ethyl[[1-(1-piperazinylmethyl)cyclopentyl]methyl]carbamate

This compound was prepared by a procedure similar to that described in example 1-C as a colorless oil.
$^1$H NMR (CDCl$_3$) δ 3.40–3.25 (m, 2H), 3.20 (s, 2H), 2.90–2.75 (m, 4H), 2.50–2.30 (m, 4H), 2.35 (s, 1H), 2.21 (s, 2H), 1.75–1.15 (m, 8H), 1.46 (s, 9H), 1.08 (t, J=6.9 Hz, 3H) ppm.

C. Dimethyl 2-[2-[4-[1-[[(tert-butoxycarbonyl)(ethyl)amino]methyl]cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a colorless oil.
$^1$H NMR (CDCl$_3$) δ 8.34 (br s, 1H), 7.72 (d, J=3.5 Hz, 1H), 7.28–7.12 (m, 3H), 7.00 (t, J=8.4 Hz, 1H), 5.99 (s, 1H), 4.06 (d, J=15.0 Hz, 1H), 3.83 (d, J=14.8 Hz, 1H), 3.55 (s, 3H), 3.54 (s, 3H), 3.64–3.50 (m, 4H), 3.48–3.18 (m, 8H), 3.10–2.90 (m, 1H), 2.52–2.40 (m, 4H), 2.32–2.22 (m, 2H), 1.46 (s, 9H), 1.80–1.20 (m, 8H), 1.08 (t, J=6.9 Hz, 3H) ppm.

D. Dimethyl 4-(2,6-dichlorophenyl)-2-[2-[4-[[1-[(ethylamino)methyl]cyclopentyl]methyl]-1-piperazinyl]-2-oxoethyl[-6-[2-(1,3-thiazol-2-yl)ethyl]-1,4-dihydro-3,5-pyridinedicarboxylate This compound was prepared by a procedure similar to that described in example 2-E as a yellow solid.
free base
$^1$H NMR (CDCl$_3$) δ 8.38 (br s, 1H), 7.72 (d, 3.5 Hz, 1H), 7.24 (d, J=8.1 Hz, 2H), 7.20 (d, J=3.3 Hz, 1H), 7.00 (t, J=7.6 Hz, 1H), 5.99 (s, 1H), 4.04 (d, J=15.1 Hz, 1H), 3.84 (d, J=15.2 Hz, 1H), 3.64–3.50 (m, 4H), 3.55 (s, 3H), 3.53 (s, 3H), 3.40–3.22 (m, 3H), 3.10–2.94 (m, 1H), 2.63 (q, J=7.1 Hz, 2H), 2.55–2.40 (m, 6H), 2.34 (br s, 2H), 1.66–1.20 (m, 8H), 1.05 (t, J=7.1 Hz, 3H) ppm.
HCl salt
mp 180–181° C. (dec.)
IR(KBr)$v_{max}$: 3398, 2951, 1692, 1949, 1508, 1433 cm$^{-1}$.
$^1$H NMR (DMSO-d$_6$) δ 7.60 (d, J=3.3 Hz, 1H), 7.50 (d, J=3.3 Hz, 1H), 7.24 (d, J=8.1 Hz, 2H), 7.05 (t, J=7.4 Hz, 1H), 5.75 (s, 1H), 4.25–2.50 (m, 20H), 3.31 (s, 3H), 3.28 (s, 3H), 1.80–1.35 (m, 8H), 1.18 (br t, J=6.9 Hz, 3H) ppm.
MS (m/z): 718 (M+H)$^+$.

Example 8

Dimethyl 4(2,6-dichlorophenyl)-2-[2-[4-[[1-[(dimethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate A. N,N-Dimethyl-N-[1-(1-piperazinylmethyl)cyclopentyl]methanamine This compound was prepared by a procedure similar to that described in example 1-C as a yellow oil. $^1$H NMR (CDCl$_3$) δ 2.90–2.78 (m, 4H), 2.52–2.42 (m, 4H), 2.26 (s, 8H), 2.23 (s, 2H), 2.07 (br s, 1H), 1.65–1.50 (m, 4H), 1.50–1.30 (m, 4H) ppm.

B. Dimethyl 4-(2,6-dichlorophenyl)-2-[2-[4-[[1-[(dimethylamino)methyl cyclopentyl]methyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow solid.
Free base
IR(KBr)$v_{max}$: 3676, 2949, 1697, 1629, 1508, 1433 cm$^{-1}$.
$^1$H NMR (CDCl$_3$) δ 8.37 (br s, 1H), 7.72 (d, 3.3 Hz, 1H), 7.24 (d, J=8.1 Hz, 2H), 7.21 (d, J=3.3 Hz, 1H), 7.00 (t, J=7.4 Hz, 1H), 5.99 (s, 1H), 4.03 (d, J=15.1 Hz, 1H), 3.85 (d, J=15.2 Hz, 1H), 3.64–3.50 (m, 4H), 3.55 (s, 3H), 3.53 (s, 3H), 3.42–3.24 (m, 3H), 3.10–2.94 (m, 1H), 2.63–2.30 (m, 14H), 1.68–1.40 (m, 8H) ppm.
MS (m/z): 718 (M+H)$^+$.

Example 9

Dimethyl 4-(2,6-dichlorophenyl)-2-[2-[4-[[1-[(diethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate A. N,N-Diethyl-N-[1-(1-piperazinylmethyl)cyclopentyl]methanamine This compound was prepared by a procedure similar to that described in example 1-C as a yellow oil.
$^1$H NMR (CDCl$_3$) δ 2.88–2.78 (m, 4H), 3.55 (q, J=7.1 Hz, 4H), 2.48–2.40 (m, 4H), 2.31 (s, 2H), 2.21 (s, 2H), 1.65–1.25 (m, 8H), 0.96 (t, J=7.1 Hz, 6H) ppm.

B. Dimethyl 4-(2,6Dichlorophenyl)-2-[2-[4-[[1-[(diethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow solid.
Free base
IR(KBr)ν$_{max}$: 3292, 2949, 1697, 1630, 1508, 1433 cm$^{-1}$.
$^1$H NMR (CDCl$_3$) δ 8.38 (br s, 1H), 7.72 (d, 3.3 Hz, 1H), 7.24 (d, J=8.2 Hz, 2H), 7.21 (d, J=3.3 Hz, 1H), 7.00 (t, J=7.4 Hz, 1H), 5.99 (s, 1H), 4.03 (d, J=15.0 Hz, 1H), 3.86 (d, J=15.2 Hz, 1H), 3.65–3.52 (m, 4H), 3.55 (s, 3H), 3.53 (s, 3H), 3.42–3.24 (m, 3H), 3.10–2.94 (m, 1H), 2.80–2.30 (m, 12H), 1.68–1.30 (m, 8H), 1.18–0.98 (m, 6H) ppm.
MS (m/z): 746 (M+H)$^+$.

Example 10

Dimethyl 4-(2,6-dichlorophenyl)-2-[2-oxo-2-[4-[[1-(1-pyrrolidinylmethyl)cyclopentyl]methyl]-1-piperazinyl]ethyl]-6-[2-(1,3-thiazol-2-yl)ethyl]-1,4-dihydro-3,5-pyridinedicarboxylate A. 1-[[1-(Pyrrolidinyl)cyclopentyl]methyl]piperazine This compound was prepared by a procedure similar to that described in example 1-C as a yellow oil.
$^1$H NMR (CDCl$_3$) δ 3.40–3.15 (m, 6H), 3.10–2.92 (m, 6H), 2.32–2.10 (m, 4H), 1.80–1.50 (m, 12H) ppm.

B. Dimethyl 4-(2,6-dichlorophenyl)-2-[2-oxo-2-[4-[[1-(1-pyrrolidinylmethyl) cyclopentyl]methyl]-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow solid.
free base
$^1$H NMR (CDCl$_3$) δ 8.42 (br s, 1H), 7.71 (d, 3.3 Hz, 1H), 7.24 (d, J=7.9 Hz, 2H), 7.21 (d, J=3.3 Hz, 1H), 7.00 (t, J=7.4 Hz, 1H), 5.99 (s, 1H), 4.00 (d, J=15.3 Hz, 1H), 3.88 (d, J=15.3 Hz, 1H), 3.65–3.45 (m, 4H), 3.55 (s, 3H), 3.53 (s, 3H), 3.40–3.25 (m, 3H), 3.06–2.93 (m, 1H), 2.74–2.42 (m, 10H), 2.38 (s, 2H), 1,84–1.36 (m, 6H) ppm.
HCl salt
mp: 205–210° C. (dec.)
IR(KBr)ν$_{max}$: 3416, 2949, 1693, 1626, 1508, 1433 cm$^{-1}$.
$^1$H NMR (DMSO-d$_6$) δ 9.23 (br s, 1H), 7.60 (d, J=3.3 Hz, 1H), 7.49 (d, J=3.3 Hz, 1H), 7.23 (d, J=8.2 Hz, 2H), 7.04 (t, J=7.4 Hz, 1H), 5.73 (s, 1H), 4.09–2.60 (m, 22H), 3.30 (s, 3H), 3.27 (s, 3H), 1.95–1.75 (m, 4H), 1.64–1.54 (m, 8H) ppm.
MS (m/z): 744 (M+H)$^+$.

Example 11

Dimethyl 2-[2-[4-[[1-[(cyclopentylamino)methyl] cyclopentyl]methyl]-1-piperazinyl]-2-oxoethyl]-4-(2,6dichlorophenyl)-6-[2-(1,3-thiazol-2-yl)ethyl]-1,4-dihydro-3,5-pyridinedicarboxylate To a suspension of dimethyl 2-[2-[4-[[1-(aminomethyl) cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate (205 mg/0.298 mmol) and cyclopentanone (0.032 ml/0.36 mmol) in dichloromethane (2 ml) was added AcOH (1 drop) and the resulting mixture was stirred for 5 minutes. NaBH(OAc)$_3$ (80 mg/0.36 mmol) was added to the mixture and the resulting mixture was stirred for 5 hours. The mixture was diluted with dichloromethane (50 ml) and the resulting solution was washed with water (10 ml) and brine (10 ml) successively. The solution was dried over magnesium sulfate, filtered and concentrated. The residue was purified by column chromatography (NH2 gel/dichloromethane:methanol=100:0-100:2) to give a yellow film (220 mg/98%).
free base
$^1$H NMR (CDCl$_3$) δ 8.39 (br s, 1H), 7.71 (d, 3.3 Hz, 1H), 7.24 (d, J=8.1 Hz, 2H), 7.20 (d, J=3.3 Hz, 1H), 7.00 (t, J=7.4 Hz, 1H), 5.99 (s, 1H), 4.04 (d, J=15.1 Hz, 1H), 3.85 (d, J=15.0 Hz, 1H), 3.64–3.50 (m, 4H), 3.55 (s, 3H), 3.53 (s, 3H), 3.40–3.22 (m, 3H), 3.10–2.90 (m, 1H), 2.46 (s, 2H), 2.60–2.40 (m, 4H), 2.31 (s, 2H), 2.25–1.20 (m, 16H) ppm.
HCl salt
mp: 174–177° C. (dec.)
IR(KBr)ν$_{max}$: 3379, 2949, 1695, 1630, 1508, 1433 cm$^{-1}$.
$^1$H NMR (DMSO-d$_6$) δ 9.40–9.10 (m, 1H), 8.80–8.40 (m, 2H), 7.60 (d, J=3.5 Hz, 1H), 7.50 (d, J=3.3 Hz, 1H), 7.24 (d, J=8.2 Hz, 2H), 7.05 (t, J=7.4 Hz, 1H), 5.76 (s, 1H), 4.40–2.50 (m, 25H), 2.10–1.30 (m, 16H) ppm.
MS (m/z) 758 (M+H)$^+$, 756 (M–H)$^-$.

Example 12

Dimethyl 4-(2,6-dichlorophenyl)-2-[2-[4-(8-(diethylamino)bicyclo[3.2.1]oct-3-yl)-1-piperazinyl]-2-oxoethyl]-6-[2-(1,3-thiazol-2-yl) ethyl]-1,4-dihydro-3,5-pyridinedicarboxylate A. 1-Benzyl4-(8-(diethylamino)bicyclo[3.2.1]oct-3-yl) piperazine This compound was prepared by a procedure similar to that described in example 11 as a white solid.
$^1$H NMR (CDCl$_3$) δ 7.34–7.20 (m, 5H), 3.50 (s, 2H), 2.63 (q, J=7.1 Hz, 4H), 2.70–1.00 (m, 18H), 0.95 (t, J=7.1 Hz, 6H) ppm.

B. (8-(diethylamino)bicyclo[3.2.1]oct-3-yl)piperazine

This compound was prepared by a procedure similar to that described in example 1-C as a white solid.
$^1$H NMR (CDCl$_3$) δ 2.96–2.82 (m, 4H), 2.63 (q, J=7.1 Hz, 4H), 2.60–1.30 (m, 15 H), 0.96 (t, J=7.1 Hz, 6H) ppm.

C. Dimethyl 4-(2,6-dichlorophenyl)-2-[2-[4-(8-(diethylamino)bicyclo[3.2.1]oct-3-yl)-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow solid.
free base
$^1$H NMR (CDCl$_3$) δ 8.41 (br s, 1H), 7.71 (d, 3.3 Hz, 1H), 7.23 (d, J=7.9 Hz, 2H), 7.20 (d, J=3.5 Hz, 1H), 6.99 (t, J=7.4 Hz, 1H), 5.99 (s, 1H), 4.12 (d, J=15.1 Hz, 1H), 3.78 (d, J=15.1 Hz, 1H), 3.65–3.55 (m, 4H), 3.55 (s, 3H), 3.53 (s, 3H), 3.40–3.25 (m, 3H), 3.12–2.94 (m,1H), 2.62 (q, J=7.1 Hz, 4H), 2.70–2.36 (m, 6H), 2.25–1.30 (m, 10H), 0.94 (t, J=6.9 Hz, 6H) ppm.
HCl salt
mp: 200–205° C. (dec.)
IR(KBr)ν$_{max}$: 2949, 1693, 1510, 1433, 1294, 1188 cm$^{-1}$.
$^1$H NMR (DMSO-d$_6$) δ 7.74 (d, J=3.3 Hz, 1H), 7.63 (d, J=3.3 Hz, 1H), 7.35 (d, J=7.7 Hz, 2H), 7.16 (t, J=7.4 Hz, 1H), 5.87 (s, 1H), 3.43 (s, 3H), 3.39 (s, 3H), 1.29 (t, J=7.2 Hz, 6H) ppm.
MS (m/z): 758 (M+H)$^+$.

Example 13

Dimethyl 4-(2,6-dichlorophenyl)-2-[2-[4-[2,2-dimethyl-3-[(methylsulfonyl)amino]propyl]-1-piperazinyl]-2-oxoethyl]-6-[2-(1,3-thiazol-2-yl) ethyl]-1,4-dihydro-3,5-pyridinedicarboxylate This compound was prepared by a procedure similar to that described in example 1-F, 1-G, 2-A, 5, 1-H, and 1-I as a yellow solid.

¹H NMR (CDCl₃) δ 8.30 (s, 1H), 7.70 (d, J=3Hz, 1H), 7.28–7.19 (m, 3H), 7.00 (t, J=7 Hz), 6.77 (bs, 1H), 5.99 (s, 1H), 3.98 (d, J=14 Hz, 1H), 3.85 (d, J=14 Hz, 1H), 3.62 (bs, 4H), 3.55 (s, 3H), 3.53 (s, 3H), 3.42–3.25 (m, 4H), 3.00 (bs, 2H), 2.92 (s, 3H), 2.55 (bs, 4H), 2.31 (s, 2H), 0.97 (s, 6H) ppm.
IR (KBr)ν$_{max}$: 3421, 2601, 1693, 1624, 1560, 1508, 1434, 1296, 1190, 1149, 1105, 1066, 960, 767, 522 cm⁻¹
MS (m/z) 742.2 (M+H)⁺
mp. 132–136° C.

Example 14

Dimethyl 2-[2-[4-[(1-cyanocyclopentyl)methyl]-1-piperazinyl]-2-oxoethyl]4-(2,6-dichlorophenyl)-6-2-(1,3-thiazol-2-yl)ethyl]-1,4-dihydro-3,5-pyridinedicarboxylate This compound was prepared by a procedure similar to that described in example 1 as a yellow solid.
Free base
¹H NMR (CDCl₃) δ 8.29 (bs, 1H), 7.72 (d, J=3 Hz, 1H), 7.27–7.19 (m, 3H), 7.00 (t, J=7 Hz, 1H), 5.99 (bs, 1H), 4.09 (d, J=14 Hz, 1H), 3.80 (d, J=14 Hz, 1H), 3.68–3.60 (m, 4H), 3.55 (s, 3H), 3.53 (s, 3H), 3.38–3.25 (m, 3H), 3.08–2.97 (m, 1H), 2.63 (m, 4H), 2.51 (s, 2H), 2.13–1.68 (m, 8H) ppm.
HCl salt
IR (KBr)ν$_{max}$: 3421, 2949, 2600, 1693, 1624, 1560, 1508, 1434, 1296, 1190, 1105, 767 cm⁻¹
MS (m/z) 686.1 (M+1) mp. 118–122° C.

Example 15

Dimethyl 2-[2-[4-(2-cyano-2-methylpropyl)-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1 as a yellow solid.
Free base
¹H NMR (CDCl₃) δ 8.28 (bs, 1H), 7.72 (d, J=3 Hz, 1H), 7.26–7.20 (m, 3H), 7.00 (t, J=7 Hz, 1H), 5.99 (s, 1H), 4.10 (d, J=14 Hz, 1H), 3.78 (d, J=14 Hz, 1H), 3.67–3.62 (m, 4H), 3.55 (s, 1H), 3.53 (s, 1H), 3.38–3.25 (m, 3H), 3.09–2.97 (m, 1H), 2.65 (m, 4H), 2.44 (s, 2H), 1.33 (s, 6H) ppm.
HCl salt
IR (KBr)ν$_{max}$: 3421, 3217, 2949, 2596, 1693, 1624, 1560, 1510, 1434, 1296, 1190, 1105, 1055, 966, 767
MS (m/z) 660.2 (M+H)⁺
mp. 120–122° C.

Example 16

Dimethyl 2-[2-[4-[3-(acetylamino)-2,2-dimethylpropyl]-1-piperazinyl]-2-oxoethyl]-4-(2,6-dichlorophenyl)-6-[2-(1,3-thiazol-2-yl)ethyl]-1,4-dihydro-3,5 pyridinedicarboxylate This compound was prepared by a procedure similar to that described in example 2-A, 4, 1-H, and 1-I as a yellow solid.
Free base
¹H NMR (CDCl₃) δ 8.27 (bs, 1H), 7.72 (d, J=3Hz, 1H), 7.23 (d, J=7 Hz, 2H), 7.21 (d, J=3 Hz, 1H), 7.12 (bs, 1H), 7.00 (t, J=7 Hz, 1H), 6.00 (s, 1H), 4.13 (d, J=14 Hz, 1H), 3.75 (d, J=14 Hz, 1H), 3.64–3.56 (m, 4H), 3.55 (s, 3H), 3.53 (s, 3H), 3.38–3.25 (m, 2H), 3.15–3.00 (m, 2H), 2.53 (bs, 4H), 2.26 (s, 2H), 1.98 (s, 3H), 0.91 (s, 6H) ppm.

HCl salt
IR (KBr)ν$_{max}$: 3421, 3282, 3095, 2950, 2601, 1693, 1627, 1560, 1510, 1434, 1296, 1190, 1105, 1055, 952, 767 cm⁻¹
MS (m/z) 706.1 (M+H)⁺
mp. 104–107° C.

Example 17

Dimethyl 2-[2-[4-[[1-(aminomethyl)cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 2 as a yellow solid.
Free base
¹H NMR (CDCl₃) δ 8.35 (bs, 1H), 7.72 (d, J=3Hz, 1H), 7.25 (d, J=7 Hz, 2H), 7.20 (d, J=3 Hz, 1H), 7.00 (t, J=7 Hz, 1H), 5.99 (bs, 1H), 4.06 (d, J=14 Hz, 1H), 3.82 (d, J=14 Hz, 1H), 3.62–3.58 (m, 4H), 3.55 (s, 3H), 3.53 (s, 3H), 3.38–3.25 (m, 3H), 3.08–2.96 (m, 1H), 2.58 (s, 2H), 2.48 (bs, 4H), 2.32 (s, 2H), 1.60–1.29 (m, 8H) ppm
HCl salt
IR (KBr)ν$_{max}$: 3402, 3091, 2950, 2684, 1693, 1624, 1508, 1434, 1296, 1232, 1190, 1105, 1053, 945, 767 cm⁻¹
MS (m/z) 690.2 (M+H)⁺
mp. 161–164° C.

Example 18

Dimethyl 2-[2-[4-(3-amino-2,2-dimethylpropyl)-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 2 as a yellow solid.
Free base
¹H NMR (CDCl₃) δ 8.36 (bs, 1H), 7.71 (d, J=3 Hz, 1H), 7.24 (d, J=7 Hz, 2H), 7.20 (d, J=3 Hz, 1H), 6.99 (t, J=7 Hz, 1H), 5.99 (s, 1H), 4.04 (d, J=14 Hz, 1H), 3.83 (d, J=14 Hz, 1H), 3.60–3.51 (m, 10H), 3.38–3.25 (m, 3H), 3.08–2.96 (m, 1H), 2.51 (bs, 4H), 2.17 (s, 2H), 0.84 (s, 6H) ppm
HCl salt
IR (KBr)ν$_{max}$: 3421, 3095, 2949, 1693, 1624, 1508, 1434, 1298, 1232, 1190, 1105, 767 cm⁻¹
MS (m/z) 664.1 (M+H)⁺
mp. 158–162° C.

Example 19

Dimethyl 4-(2,6-dichlorophenyl)-2-[2-[4-[3-(ethylamino)-2,2-dimethylpropyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 3 as a yellow solid.
Free base
¹H NMR (CDCl₃) δ 8.40 (bs, 1H), 7.71 (d, J=3 Hz, 1H), 7.24 (d, J=7 Hz, 2H), 7.20 (d, J=3 Hz, 1H), 6.99 (t, J=7 Hz, 1H), 5.99 (s, 1H), 4.02 (d, J=14 Hz, 1H), 3.85 (d, J=14 Hz, 1H), 3.6–3.51 (m, 10H), 3.38–3.25 (m, 3H), 3.07–2.95 (m, 1H), 2.60 (q, J=6.5 Hz, 2H), 2.50 (m, 4H), 2.41 (s, 2H), 2.20 (s, 2H), 1.08 (t, J=6.5 Hz, 3H), 0.87 (s, 6H) ppm.
HCl salt
IR (KBr)ν$_{max}$: 3396, 3095, 2949, 1693, 1624, 1510, 1434, 1298, 1234, 1191, 1105, 1053, 767 cm⁻¹
m/z 692.2 (M+H)⁺ ᵐᵖ·⁼154–157° C.

Example 20

Dimethyl 4-(2,6-dichlorophenyl)-2-[2-[4-[3-methyl-3-(2-oxo-1-pyrrolidinyl)butyl]-1-piperazinyl]-2-oxoethyl]-6-[2-(1,3-thiazol-2-yl)ethyl]-1,4-dihydro-3,5-pyridinedicarboxylate

A. 3-(4-Benzyl-1-piperazinyl)-1,1-dimethylpropylamine

To a suspension of CeCl$_3$ (8.5 g/34.5 mmol) in tetrahydrofuran (150 ml) was added methyl lithium (30.2 ml/34.5 mmol) at −78° C. and the resulting yellow mixture was stirred for 30 min at the same temperature. A solution of 3-(4-benzyl-1-piperazinyl)propanenitrile (2.47 g/10.8 mmol) in tetrahydrofuran (50 ml) was added dropwise to the mixture and the resulting mixture was allowed to warm to ambient temperature. The mixture was further stirred for 2 hours at the same temperature, and then 2 N NaOH was added. The resulting suspension was filtered through a pad of Celite and the filtrate was concentrated. The residue was diluted with dichloromethane (200 ml) and then the solution was washed with water and brine successively. The solution was dried over magnesium sulfate, filtered and concentrated. The residue was purified by column chromatography (NH$_2$ gel/50 g/dichloromethane:methanol=200:5) to give a pale brown oil.
$^1$H NMR (CDCl$_3$) 7.36–7.20 (m, 5H), 3.51 (s, 2H), 2.58–2.35 (m, 8H), 1.62–1.46 (m, 2H), 1.11 (s, 6H) ppm B. N-[3-(4-benzyl-1-piperazinyl)-1,1-dimethylpropyl]-4-chlorobuthanamide To a stirred solution of N-[3-(4-benzyl-1-piperazinyl)-1,1-dimethylpropyl]amine (1.83 g/7.01 mmol) in tetrahydrofuran (15 ml) were added 2 N NaOH (5.3 ml/10.6 mmol) and 4-chloropropionylchloride (1.2 ml/10.5 mmol), and the mixture was stirred for 1 day. The reaction mixture was quenched with water (80 ml) and the whole was extracted with dichloromethane (100 ml×2). The combined extracts were washed with brine (80 ml), dried over magnesium sulfate, filtered and concentrated in vacuo. The residue was crystallized from diethylether to give a white solid. (0.81 g/32%).
$^1$H NMR (CDCl$_3$) δ 7.37–7.27 (m, 5H), 6.50 (br s, 1H), 3.65 (s, 2H), 3.63–3.56 (m, 2H), 3.04–2.89 (m, 10H), 2.39–2.35 (m, 2H), 2.27–2.15 (m, 2H), 2.14–2.00 (m, 2H), 1.37 (s, 6H) ppm.

C. 1-[3-(4-Benzyl-1-piperazinyl)-1,1-dimethylpropyl]-2-pyrrolidinone

To a solution of N-[3-(4-benzyl-1-piperazinyl)-1,1-dimethylpropyl]-4-chlorobuthanamide (0.81 g/2.22 mmol) in tetrahydrofuran (20 ml) was added potassium tert-butoxyde (0.41 g/3.33 mmol) and the mixture was stirred for 24 hours and then stirred for 1 h at reflux temperature. The reaction mixture was quenched with water (30 ml) and the whole was extracted with ethyl acetate (30 ml×2). The combined extracts were washed with brine (30 ml), dried over magnesium sulfate, filtered and concentrated in vacuo. The residue was purified by column chromatography (NH$_2$ gel/dichloromethane) to give a colorless oil (0.51 g/70%).
$^1$H NMR (CDCl$_3$) δ 7.32–7.28 (m, 5H), 3.50 (s, 2H), 3.43 (t, J=6.9 Hz, 2H), 2.47 (br s, 8H), 2.46–2.28 (m, 4H), 2.10–1.84 (m, 4H), 1.37 (s, 6H) ppm.

D. 1-[3-(1-piperazinyl)-1,1-dimethylpropyl]-2-pyrrolidinone

This compound was prepared by a procedure similar to that described in example 1-C as a yellow solid.
$^1$H-NMR (DMSO-d$_6$) δ 3.33–3.20 (m, 10H), 2.98–2.88 (m, 2H), 2.20–2.05 (m, 2H), 1.81–1.65 (m, 4H), 1.16 (s, 6H) ppm.

E. Dimethyl 4-(2,6-dichlorophenyl)-2-[2-[4-[3-methyl-3-(2-oxo-1-pyrrolidinyl)butyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow solid.
Free base
$^1$H NMR (CDCl$_3$) δ: 8.33 (s, 1H), 7.71 (d, J=3.3 Hz, 1H), 7.26 (d, J=7.9 Hz, 2H), 7.21 (d, J=3.3 Hz, 1H), 6.99 (t, J=7.9 Hz, 1H), 5.99 (s, 1H), 4.06 (d, J=5.0 Hz, 1H), 3.83 (d, J=5.0 Hz, 1H), 3.72–3.50 (m, 4H), 3.55 (s, 3H), 3.53 (s, 3H), 3.47 (t, J=6.9 Hz, 2H), 3.38–3.22 (m, 3H), 3.08–2.94 (m, 1H), 2.51–2.28 (m, 6H), 2.24–2.02 (m, 2H), 2.02–1.86 (m, 4H), 1.36 (s, 6H) ppm.
HCl salt
mp: 179° C. (dec.)
IR (KBr)ν$_{max}$: 1693, 1653, 1508, 1435, 1296, 1188, 1105, 768 cm$^{-1}$.
MS (m/z): 732 (M+H)$^+$

Example 21

Dimethyl 4-(2,6-dichlorophenyl)-2-[2-[4-[2,2-dimethyl-3-(2-oxo-1-pyrrolidinyl)-propyl]-piperazinyl]-2-oxoethyl]-6-[2-(1,3-thiazol-2-yl)ethyl]-1,4-dihydro-3,5-pyridinedicarboxylate

A. N-[3-(4-Benzyl-1-piperazinyl)-2,2-dimethylpropyl]-4-chlorobutanamide

This compound was prepared by a procedure similar to that described in example 20-B as a colorless oil.
$^1$H NMR (CDCl$_3$) δ: 8.27 (br s, 1H), 7.33–7.27 (m, 5H), 3.62 (t, J=6.1 Hz, 2H), 3.52 (s, 2H), 3.14 (d, J=4.8 Hz, 2H), 2.64–2.42 (m, 8H), 2.35 (t, J=7.5 Hz, 2H), 2.30 (s, 2H), 2.19–2.07 (m, 2H), 0.91 (s, 6H) ppm B. 1-[3-(4-Benzyl-1-piperazinyl)-2,2-dimethylpropyl]-2-pyrrolidinone This compound was prepared by a procedure similar to that described in example 20-C as a colorless oil.
$^1$H NMR (CDCl$_3$) δ: 7.32–7.28 (m, 5H), 3.49 (s, 2H), 3.47 (t, J=6.1 Hz, 2H), 3.11 (s, 2H), 2.59–2.39 (m, 8H), 2.36 (t, J=7.9 Hz, 2H), 2.04–1.93 (m, 2H), 0.90 (s, 6H) ppm C. 1-[3-(1-Piperazinyl)-2,2-dimethylpropyl]-2-pyrrolidinone This compound was prepared by a procedure similar to that described in example 1-C as a yellow solid.
$^1$H NMR (CDCl$_3$) δ:3.48 (t, J=6.9 Hz, 2H), 3.12 (s, 2H), 2.88–2.81 (m, 4H), 2.52–2.46 (m, 4H), 2.37 (t, J=8.0 Hz, 2H), 2.14 (s, 2H), 2.07–1.94 (m, 2H), 0.91 (s, 6H) ppm.

Dimethyl 4-(2,6-dichlorophenyl)-2-[2-[4-[2,2-dimethyl-3-(2-oxo-1-pyrrolidinyl)-propyl]-piperazinyl]-2-oxoethyl]-6-[2-(1,3-thiazol-2-yl-ethyl]-1,4-dihydro-3,5-pyridinedicarboxylate

This compound was prepared by a procedure similar to that described in example 1-D as a yellow solid.
Free base
$^1$H NMR (CDCl$_3$) δ: 8.37 (s, 1H), 7.71 (d, J=3.3 Hz, 1H), 7.26 (d, J=6.9 Hz, 2H), 7.21 (d, J=3.3 Hz, 1H), 6.99 (t, J=6.9 Hz, 1H), 5.99 (s, 1H), 4.03 (d, J=5.1 Hz, 1H), 3.84 (d, J=5.1 Hz, 1H), 3.59 (br s, 4H), 3.55 (s, 3H), 3.53 (s, 3H), 3.47 (t, J=7.0 Hz, 2H), 3.37–3.27 (m, 3H), 3.11 (s, 2H), 3.04–2.94 (m, 1H), 2.51 (br s, 4H), 2.37 (t, J=7.9 Hz, 2H), 2.18 (s, 2H), 2.09–1.93 (m, 2H), 0.92 (s, 6H) ppm.
HCl salt
mp: 194° C. (dec.)
IR (KBr)ν$_{max}$: 3400, 1700, 1643, 1506, 1433, 1298, 1186, 1105, 768 cm$^{-1}$.
MS (m/z): 732 (M+H)$^+$

Example 22

Dimethyl 4-(2,6-dichlorophenyl)-2-[2-oxo-2-[4-[3-(2-oxo-1-pyrrolidinyl)propyl]-1-piperazinyl]ethyl]-6-[2-(1,3-thiazol-2-yl)ethyl]-1,4-dihydro-3,5-pyridinedicarboxylate

A. 1-[3-(4-Benzyl-1-piperazinyl)propyl]-2,5-pyrrolidinedione

To a mixture of 3-(4-benzylpiperazin-1-yl)propan-1-ol (48.5 g/0.21 mol), triphenylphosphine (81.6 g/0.31 mol), succimide (30.7 g/0.31 mol) in tetrahydrofuran (1000 ml) was added dropwise diethylazodicarboxylate (49.0 ml/0.31 mol) and the mixture was stand overnight. The solvent was removed in vacuo and the residue was purified by column chromatography (Si/230–400 mesh/dichloromethane:methanol=15:1) to give a colorless oil (55.1 g/83%).
$^1$H NMR (CDCl$_3$) δ 7.32–7.28 (m, 5H), 3.55 (t, J=7.1 Hz, 2H), 3.50 (s, 2H), 2.67 (s, 4H), 2.50–2.30 (m, 10H), 1.81–1.65 (m, 2H) ppm.

B. 1-[3-(4-Benzyl-1-piperazinyl)propyl]-2-pyrrolidinone

Sodium borohydride (32.4 g/0.171 mol) was added portionwise to a solution of 1-[3-(4-benzyl-1-piperazinyl)propyl]-2,5-pyrrolidinedione (54.0 g/0.171 mol) in tetrahydrofuran-methanol (1:5, 600 ml) and the mixture was stirred for 2 hours. The reaction mixture was quenched with acetone (50 ml). The volatile was removed in vacuo. The residue and triethylsilane (25.0 g/0.215 mol) were dissolved with chloroform (300 ml). To the solution was added dropwise trifluoroacetic acid (165 ml/2.15 mol), and the mixture was stirred for 1 hour. The reaction was quenched with 2 N—NaOH(200 ml) and the whole was extracted with dichloromethane (500 ml×3). The combined extracts were washed with brine (500 ml), dried over magnesium sulfate, filtered and concentrated in vacuo. The residue was purified by column chromatography (Si, 230–400 mesh/150 g/dichloromethane:methanol=12:1–10:1) to give a colorless oil (19.5 g/38%).
$^1$H NMR (CDCl$_3$) δ 7.32–7.27 (m, 5H), 3.54 (s, 2H), 3.38 (t, J=7.0 Hz, 2H), 3.31 (t, J=7.1 Hz, 2H), 2.68–2.34 (m, 12H), 2.07–1.95 (m, 2H), 1.83–1.69 (m, 2H) ppm.

C. 1-[3-(1-Piperazinyl)propyl]-2-pyrrolidinone

This compound was prepared by a procedure similar to that described in example 1-C as a yellow oil
$^1$H NMR (CDCl$_3$) δ 3.39 (t, J=7.0 Hz, 2H), 3.31 (t, J=7.3 Hz, 2H), 2.89 (t, J=4.9 Hz, 4H), 2.46–2.28 (m, 8H), 2.07–1.95 (m, 2H), 1.78–1.66 (m, 2H) ppm.

D. Dimethyl 4-(2,6-dichlorophenyl)2-[2-oxo-2-[4-[3-(2-oxo-1-pyrrolidinyl)propyl]-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow amorphous.
Free base
$^1$H NMR (CDCl$_3$) δ: 8.33 (s, 1H), 7.71 (d, J-3.3 Hz, 1H), 7.24 (d, J=7.9 Hz, 2H), 7.20 (d, J=3.3 Hz, 1H), 7.00 (t, J=7.9 Hz, 1H), 5.99 (s, 1H), 4.09 (d, J=5.0 Hz, 1H), 3.80 (d, J=5.0 Hz, 1H), 3.68–3.58 (m, 4H), 3.55 (s, 3H), 3.53 (s, 3H), 3.49–3.26 (m, 9H), 3.08–2.94 (m, 1H), 2.46–2.31 (m, 6H), 2.09–1.95 (m, 2H), 1.77–1.63 (m, 2H) ppm.
HCl salt
mp 185–190° C.(dec.)
IR(KBr)ν$_{max}$: 1693, 1670, 1641, 1622, 1510, 1464, 1431, 1296, 1190, 1103 cm$^{-1}$.
MS (m/z): 704 (M+H)$^+$ Example 23

Dimethyl 4-(2,6-dichlorophenyl)-2-[2-oxo-2-[4-[4-(2-oxo-1-pyrrolidinyl)cyclohexyl]-1-piperazinyl]ethyl]-6-[2-(1,3-thiazol-2-yl)ethyl]-1,4-dihydro-3,5-pyridinedicarboxylate A. 2-[4-(4-Benzyl-1-piperazinyl)cyclohexyl]-1H-isoindole-1,3(2H)-dione To a solution of 2-(4-oxocyclohexyl)-1H-isoindole-1,3(2H)dione (3.78 g, 15.5 mmol), which was prepared according to the literature (J. Med. Chem., 1993, 1918), 1-benzylpiperazine (2.99 g/17.1 mmol) and AcOH (1.00 ml/17.1 mmol) in dichloroethane (50 ml) was added sodium triacetoxyborohydride (6.57 g/31.0 mmol) and the mixture was stirred for 2 days. The reaction mixture was poured into water (50 ml) and the mixture was extracted with dichloromethane (100 ml). The extract was washed with brine (50 ml), dried over magnesium sulfate, filtered and concentrated in vacuo. The residue was purified by column chromatography (NH2 gel/dichloromethane) to give a colorless oil (5.00 g/89%).
$^1$H NMR (CDCl13) δ 7.86–7.65 (m, 4H), 7.35–7.28 (m, 5H), 4.25–4.10 (m, 1H), 3.52 (s, 2H), 2.73–2.40 (m, 8H), 2.20–2.08 (m, 1H), 1.80–1.35 (m, 8H) ppm.

B. 4-(4-Benzyl-1-piperazinyl)cyclohexylamine

To a solution of 2-[4-(4-benzyl-1-piperazinyl)cyclohexyl]-1H-isoindole-1,3(2H)-dione (5.00 g, 12.4 mmol) in ethanol-dichloromethane (10:3/65 ml) was added NH$_2$NH$_2$-water (2.4 ml /50.0 mmol) and the mixture was stirred for 1 day. After filtration, the filtrate was concentrated in vacuo. The residue was purified by column chromatography (NH2 gel/dichloromethane) to give a colorless oil (2.82 g/89%).
$^1$H NMR (CDCl$_3$) δ 7.35–7.28 (m, 5H), 3.51 (s, 2H), 3.05–2.96 (m, 1H), 2.68–2.35 (m, 8H), 2.25–2.10 (m, 1H), 1.72–1.48 (m, 8H) ppm.

C. N-[4-(4-Benzyl-1-piperazinyl)cyclohexyl]-4-chlorobutanamide

This compound was prepared by a procedure similar to that described in example 20-B as a yellow oil.
$^1$H NMR (CDCl$_3$) δ 7.35–7.28 (m, 5H), 5.68–5.40 (m, 1H), 3.66–3.44 (m, 4H), 2.60–200 (m, 13H), 1.82–1.38 (m, 8H) ppm.

D. 1-[4-(4-Benzyl-1-piperazinyl)cyclohexyl]-2-pyrrolidinone

This compound was prepared by a procedure similar to that described in example 20-C as a yellow oil.
$^1$H NMR (CDCl$_3$) δ 7.33–7.27 (m, 5H), 4.10–3.96 (m, 1H), 3.50 (s, 2H), 3.39 (t, J=7.0 Hz, 2H), 2.55–2.30 (m, 10H), 2.19–2.11 (m, 11H), 2.07–1.92 (m, 2H), 1.88–1.70 (m, 2H), 1.51–1.30 (m, 6H) ppm.

E. 1-[4-(1-Piperazinyl)cyclohexyl]-2-pyrrolidinone

This compound was prepared by a procedure similar to that described in example 1-C as a yellow oil.
$^1$H NMR (CDCl$_3$) δ 4.10–3.96 (m, 1H), 3.44–3.35 (m, 2H), 2.93–2.85 (m, 6H), 2.18–1.93 (m, 5H), 1.83–1.73 (m, 4H), 1.53–1.44 (m, 6H) ppm.

F. Dimethyl 4-(2,6-dichlorophenyl)-2-[2-oxo-2-4-[4-(2-oxo-pyrrolidinyl)cyclohexyl]-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow amorphous.
Free base
$^1$H NMR (CDCl$_3$) δ: 8.36 (s, 1H), 7.71 (d, J=3.3 Hz, 1H), 7.26 (d, J=7.9 Hz, 2H), 7.20 (d, J=3.3 Hz, 1H), 7.00 (t, J=7.9 Hz, 1H), 6.00 (s, 1H), 4.10–3.95 (m, 2H), 3.84 (d, J=5.0 Hz, 1H), 3.64 (br.s, 4H), 3.55 (s, 3H), 3.54 (s, 3H), 3.45–3.26 (m, 5H), 2.95–2.90 (m, 1H), 2.49–2.32 (m, 6H), 2.21–2.10 (m, 1H), 2.08–1.93 (m, 2H), 1.85–1.35 (m, 8H) ppm.
HCl salt
mp: 182–184° C. (dec.)
IR(KBr)ν$_{max}$: 3423, 1692, 1649, 1510, 1435, 1294, 1190, 1101, 768 cm$^{-1}$.
MS (m/z): 744 (M+H)$^+$ Example 24

Dimethyl 4-(2,6dichlorophenyl)-2-[2-[4-[3-(1,1-dioxoisothiazolinyl)propyl]-1-piperadinyl]-2-oxoethyl]-6-[2-(1,3-thiazol-2-yl)ethyl]-1,4-dihydro-3,5-pyridinedicarboxylate A. N-[3-(4-Benzyl-1-piperazinyl)propyl]-3-chloro-1-propanesulfonamide To a stirred solution of 3-(4-benzyl-1-piperazinyl) propylamine (2.01 g/8.61 mmol) in tetrahydrofuran (15 ml) were added 2 N NaOH (5.6 ml/ 11.2 mmol) and 3-chloropropanesulfonylchloride (2.00 g/11.3 mmol), and the mixture was stirred for 1 day. The reaction mixture was quenched with water (50 ml) and the whole was extracted with ethyl acetate (50 ml). The extract was washed with brine (50 ml), dried over magnesium sulfate, filtered and concentrated in vacuo. The residue was purified by column chromatography ($NH_2$ gel/dichloromethane) to give a colorless oil.

$^1$H NMR ($CDCl_3$) δ 7.32–7.28 (m, 5H), 3.80–3.00 (m, 8H), 2.70–2.45 (m, 10H), 2.35–2.20 (m, 2H), 1.88–1.70 (m, 2H) ppm.

B. 2-[3-(4-Benzyl-1-piperazinyl)propyl]isothiazolidine-1,1-dione

Sodium (0.23 g/10.0 mmol) was added to ethanol (20 ml). To the resulting solution was added N-[3-(4-benzyl-1-piperazinyl)propyl]-3-chloro-1-propanesulfonamide in ethanol (20 ml) and the mixture was stirred for 1 day at reflux temperature. The solvent was removed in vacuo and the residue was diluted with dichloromethane (50 ml) and water (50 ml). The aqueous layer was extracted with dichloromethane (50 ml). The combined extracts were washed with brine (50 ml), dried over magnesium sulfate, filtered and concentrated in vacuo. The residue was purified by column chromatography ($NH_2$ gel/dichloromethane) to give a colorless oil (0.60 g/21%).

$^1$H NMR ($CDCl_3$) δ 7.32–7.28 (m, 5H), 3.51 (s, 2H), 3.24 (t, J=6.8 Hz, 2H), 3.14 (t, J=7.7 Hz, 2H), 3.06 (t, J=7.2 Hz, 2H), 2.60–2.26 (m, 12H), 1.90–1.73 (m, 2H) ppm.

C. 2-[3-(1-Piperazinyl)propyl]isothiazoidine-1,1-dione

This compound was prepared by a procedure similar to that described in example 1-C as a yellow oil.

$^1$H NMR ($CDCl_3$) δ 3.25 (t, J=6.8 Hz, 2H), 3.15 (t, J=7.7 Hz, 2H), 3.07 (t, J=7.2 Hz, 2H), 2.93–2.84 (m, 4H), 2.46–2.37 (m, 6H), 1.87–1.71 (m, 4H) ppm.

D. Dimethyl 4-(2,6-dichlorophenyl)-2-[2-[4-[3-(1,1-dioxoisothiazolinyl)propyl]-1-piperadinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow amorphous.
Free base $^1$H NMR ($CDCl_3$) δ: 8.34 (br s, 1H), 7.71 (d, J=3.3 Hz, 1H), 7.24 (d, J=7.9 Hz, 2H), 7.21 (d, J=3.3 Hz, 1H), 7.00 (t, J=7.9 Hz, 1H), 5.99 (s, 1H), 4.09 (d, J=15.0 Hz, 1H), 3.81 (d, J=15.0 Hz, 1H), 3.68–3.58 (m, 4H), 3.55 (s, 3H), 3.53 (s, 3H), 3.39–2.97 (m, 10H), 2.49–2.24 (m, 8H), 1.87–1.71(m, 2H) ppm.
HCl salt
IR(KBr)$v_{max}$: 3402, 1693, 1510, 1433, 1296, 1190, 1103, 768 $cm^-$.
mp: 148–150° C. (dec.)
MS (m/z): 740 (M+H)$^+$ Example 25

Dimethyl 4-(2,6-dichlorophenyl)-2-[2-oxo-2-[4-[3-(2-oxo-1,3-oxazolidin-3-yl)propyl]-1-piperadinyl]ethyl]-6-[2-(1,3-thiazol-2-yl)ethyl]-1,4-dihydro-3,5-pyridinedicarboxylate A. 2-Chloroethyl 3-(4-benzyl-1-piperazinyl)propylcarbamate To a stirred solution of 3-(4-benzyl-1-piperazinyl) propylamine (2.01 g/8.61 mmol) in tetrahydrofuran (15 ml) were added 2 N NaOH (6.5 ml/13.0 mmol) and 2-chloroethylchloroformate (1.38 ml/12.9 mmol), and the mixture was stirred for 1 d. Water (50 ml) was added to the mixture and the whole was extracted with ethyl acetate (50 ml). The extract was washed with brine (50 ml), dried over magnesium sulfate, filtered and concentrated in vacuo. The residue was purified by column chromatography ($NH_2$ gel/dichloromethane) to give a colorless oil.

$^1$H NMR ($CDCl_3$) δ 7.32–7.28 (m, 5H), 4.37–4.24 (m, 2H), 3.90–3.83 (m, 2H), 3.51 (s, 2H), 3.32–3.22 (m, 2H), 2.62–2.30 (m, 10H), 1.76–1.61 (m, 2H) ppm.

B. 3-[3-(4-Benzyl-1-piperazinyl)propyl]-1,3-oxazolidin-2-one

Sodium hydride(60% in oil, 0.5 g/12.5 mmol) was added to a solution of 2-chloroethyl 3-(4-benzyl-1-piperazinyl)propylcarbamate in dimethylformamide(20 ml) and stirred for 1 day at 80° C. The solvent was removed in vacuo and the residue was diluted with dichloromethane (50 ml) and water (50 ml). The aqueous layer was extracted with dichloromethane (50 ml). The combined extracts were washed with brine (50 ml), dried over magnesium sulfate, filtered and concentrated in vacuo. The residue was purified by column chromatography ($NH_2$ gel/dichloromethane) to give a colorless oil (1.40 g/54%).

$^1$H NMR ($CDCl_3$) δ 7.32–7.28 (m, 5H), 4.34–4.27 (m, 2H), 3.59–3.52 (m, 2H), 3.51 (s, 2H), 3.30 (t, J=7.2 Hz, 2H), 2.66–2.31 (m, 10H), 1.80–1.75 (m, 2H) ppm.

C. 3-[3-(1-Piperazinyl)propyl]-1,3-oxazolidin-2-one

This compound was prepared by a procedure similar to that described in example 1-C as a yellow amorphous.

$^1$H NMR ($CDCl_3$) δ 4.32 (t, J=8.0 Hz, 2H), 3.57 (t, J=8.0 Hz, 2H), 3.31 (t, J=7.2 Hz, 2H), 2.93–2.87 (m, 4H), 2.47–2.34 (m, 6H), 1.82–1.70 (m, 2H) ppm.

D. Dimethyl 4-(2,6-dichlorophenyl)-2-[2-oxo-2-[4-[3-(2-oxo-1,3-oxazolidin-3-yl)propyl]-1-piperadinyl]ethyl]-6-[2-(1,3-thiazol-2-yl)ethyl]-4-dihydro-3,5-pyridinedicarboxylate This compound was prepared by a procedure similar to that described in example 1-D as a yellow amorphous.
Free base $^1$H NMR ($CDCl_3$) δ: 8.32 (s, 1H), 7.71 (d, J=3.3 Hz, 1H), 7.26 (d, J=7.9 Hz, 2H), 7.21 (d, J=3.3 Hz, 1H), 7.00 (t, J=7.9 Hz, 1H), 5.99 (s, 1H), 4.374.28 (m, 2H), 4.10 (d, J=15.0 Hz, 1H), 3.79 (d, J=15.0 Hz, 1H), 3.68–3.52 (m, 6H), 3.55 (s, 3H), 3.54 (s, 3H), 3.39–3.26 (m, 5H), 3.08–2.96 (m, 1H), 2.49–2.34 (m, 6H), 1.80–1.64 (m, 2H) ppm.
HCl salt
mp: 155–157° C. (dec.)
IR (KBr)$v_{max}$: 3414, 1736, 1693, 1510, 1433, 1188, 1103, 766 $cm^{-1}$.
MS (m/z): 706 (M+H)$^+$ Example 26

Dimethyl 4-(2,6-dichlorophenyl)-2-[2-oxo-2-[4-[[1-[(2-oxo-1-pyrrolidinyl)methyl]cyclohexyl]methyl-1-piperazinylethyl]-6-[2-(1,3-thiazol-2-yl)ethyl]-1,4-dihydro-3,5pyridinedicarboxylate A. N-[[1-[(4-Benzyl-1-piperazinyl)methyl]cyclohexyl]methyl]-4-chlorobuthanamide This compound was prepared by a procedure similar to that described in example 20-B as a yellow amorphous.

$^1$H NMR ($CDCl_3$) δ 8.51 (br s, 1H), 7.32–7.28 (m, 5H), 3.61 (t, J=6.1 Hz, 2H), 3.52 (s, 2H), 3.26 (d, J 4.6 Hz, 2H), 2.70–2.32 (m, 10H), 2.32–2.05 (m, 4H), 1.60–1.15 (m, 10H) ppm.

B. 1-[[1-[(4-Benzyl-1-piperazinyl)methyl]cyclohexyl]methyl]-2-pyrrolidinone

This compound was prepared by a procedure similar to that described in example 20-C as a yellow amorphous.

¹H NMR (CDCl₃) δ 7.32–7.28 (m, 5H), 3.49 (s, 2H), 3.49–3.43 (m, 2H), 3.22 (s, 2H), 2.60–2.30 (m, 10H), 2.25 (s, 2H), 2.07–1.92 (m, 2H), 1.60–1.15 (m, 10H) ppm.

C. 1-[[1-[(1-Piperazinyl)methyl]cyclohexyl]methyl]-2-pyrrolidinone

This compound was prepared by a procedure similar to that described in example 1-C as a yellow oil.

¹H NMR (CDCl₃) δ 3.50–3.44 (m, 2H), 3.23 (s, 2H), 2.88–2.80 (m, 4H), 2.47–2.30 (m, 6H), 2.23 (s, 2H), 2.03–1.93 (m, 2H), 1.60–1.15 (m, 10H) ppm.

D. Dimethyl 4-(2,6-dichlorophenyl)-2-[2-oxo-2-[4-[[1-[(2-oxo-1-pyrrolidinylmethylcyclohexyl]methyl-1-piperazinyl]ethyl]-6-[2-(1,3-thiazol-2-yl)ethyl[-1,4-dihydro-3,5pyridinedicarboxylate This compound was prepared by a procedure similar to that described in example 1-D as a yellow amorphous.

Free base

¹H NMR (CDCl₃) δ: 8.39 (br s, 1H), 7.71 (d, J=3.3 Hz, 1H), 7.26 (d, J=7.9 Hz, 2H), 7.21 (d, J=3.3 Hz, 1H), 7.00 (t, J=7.9 Hz, 1H), 5.99 (s, 11), 4.02 (d, J=15.2 Hz, 1H), 3.85 (d, J=15.2 Hz, 1H), 3.68–3.50 (m, 4H), 3.55 (s, 3H), 3.53 (s, 3H), 3.48–3.29 (m, 7H), 3.08–2.96 (m, 1H), 2.60–2.42 (m, 4H), 2.40–2.36 (m, 2H), 2.07 (s, 2H), 2.12–1.95 (m, 4H), 1.62–1.37

HCl salt mp: 110–112° C. (dec.)

IR (KBr)ν$_{max}$: 2936, 1647, 1510, 1433, 1294, 1186, 1103, 768 cm⁻¹.

MS (m/z): 772 (M+H)⁺

Example 27

Dimethyl 4-(2,6-dichlorophenyl)-2-[2-oxo-2-[4-[[1-[(2-oxo-1-pyrrolidinyl)methyl]cyclopentyl]methyl-1-piperazinyl]ethyl]-6-[2-(1,3-thiazol-2-yl)ethyl]-1,4-dihydro-3,5-pyridinedicarboxylate A. N-[[1-[(4-Benzyl-1-piperazinyl)methyl]cyclopentyl]methyl]-4-chlorobutanamide This compound was prepared by a procedure similar to that described in example 20-B as a yellow amorphous.

¹H NMR (CDCl₃) δ 8.26 (br s, 1H), 7.33–7.28 (m, 5H), 3.62 (t, J=6.1 Hz, 2H), 3.52 (s, 2H), 3.20 (d, J=5.1 Hz, 2H), 2.65–2.08 (m, 14H), 1.75–1.25 (m, 8H) ppm.

B. 1-[[1-[(4-Benzyl-1-piperazinyl)methyl]cyclopentyl]methyl]-2-pyrrolidinone

This compound was prepared by a procedure similar to that described in example 20-C as a yellow amorphous.

¹H NMR (CDCl3) δ 7.32–7.28 (m, 5H), 3.49 (s, 2H), 3.46 (t, J=6.8 Hz, 2H), 3.25 (s, 2H), 2.65–2.30 (m, 10H), 2.25 (s, 2H), 2.04–1.91 (m, 2H), 1.56–1.30 (m, 8H) ppm.

C. 1-[[1-[(1-Piperazinyl)methyl]cyclopentyl]methyl]-2-pyrrolidinone

This compound was prepared by a procedure similar to that described in example 1-C as a yellow oil.

¹H NMR (CDCl₃) δ 3.48 (t, J=6.9 Hz, 2H), 3.26 (s, 2H), 2.98–2.81 (m, 4H), 2.48–2.38 (m, 4H), 2.36 (t, J=8.1 Hz, 2H), 2.23 (s, 2H), 2.05–1.92 (m, 2H), 1.77–1.34 (m, 8H) ppm.

D. Dimethyl 4(2,6 dichlorophenyl)-2-[2-oxo-2-[4-[[1-[(2-oxo-1-pyrrolidinyl)methylcyclopentyl]methyl-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow amorphous.

Free base

¹H NMR (CDCl₃) δ: 8.35 (s, 1H), 7.71 (d, J=3.3 Hz, 1H), 7.27–7.19 (m, 3H), 7.00 (t, J=7.9 Hz, 11H), 5.99 (s, 1H), 4.04 (d, J=15.0 Hz 11H), 3.83 (d, J=15.0 Hz, 1H), 3.75–3.50 (m, 4H), 3.55 (s, 3H), 3.53 (s, 3H), 3.48–3.29 (m, 5H), 3.26 (s, 2H), 3.08–2.96 (m, 1H), 2.47 (br.s, 4H), 2.36 (t, J=8.1 Hz, 2H), 2.27 (s, 2H), 2.12–1.80 (m, 4H), 1.80–1.54 (m, 4H), 1.37–1.20 (m, 2H) ppm.

HCl salt mp: 120–124° C. (dec.)

IR (KBr)ν$_{max}$: 1638, 1508, 1433, 1294, 1186, 1103, 768 cm⁻¹.

MS (m/z): 758 (M+H)⁺

Example 28

Dimethyl 4-(2,6-dichlorophenyl)-2-[2-[4-[2-(1-hydroxycyclohexyl)ethyl]-1-piperazinyl]-2-oxoethyl]-6-[2-(1,3-thiazol-2-yl)ethyl]-1,4-dihydro-3,5-pyridinedicarboxylate A. 1-Benzyl-4-(2-cyclohexylidenepropyl)piperazine Osmium tetroxide (200 mg) was added to a mixture of (1.56 g/9.22 mmol), NaIO4 (5.92 g/ 27.7 mmol), water-dioxane (10 ml, 30 ml), and the mixture was stirred for 2 hours. The mixture was poured into water (50 ml) and extracted with diethylether(50 ml×2). The combined extracts were washed with water (10 ml) and brine (10 ml) successively. The organic layer was dried over magnesium sulfate, filtered and concentrated in vacuo. The residue was dissolves with 1,2-dichloroethane. To the solution were added 1-benzylpiperazine and sodium triacetoxyborohydride under nitrogen and the mixture was stirred for 3 h. The mixture was poured into water (20 ml) and extracted with dichloromethane (20 ml×2). The combined extracts were washed with brine, dried over magnesium sulfate, filtered and concentrated in vacuo. The residue was purified by column chromatography (Si, 230–400 mesh/dichloromethane:methanol=50:1) to give a colorless oil (0.70 g/27%).

¹H NMR (CDCl₃) δ 7.33–7.28 (m, 5H), 5.42 (s, 1H), 3.80–3.70 (m, 2H), 3.51 (s, 2H), 2.60–2.36 (m, 8H), 2.15–1.46 (m, 10H) ppm.

B. 1-[2-(4-Benzyl-1-piperazinyl)ethyl]cyclohexanol

Mercury acetate (0.78 g/2.44 mol) was added to a mixture of 1-benzyl-4-(2-cyclohexylidenepropyl)piperadine (0.70 g/2.46 mmol) in tetrahydrofuran-water (5 ml, 5 ml), and the mixture was stirred for 2 hours. Sodium borohydride (0.19 g/4.92 mmol) was added to the mixture and the resulting mixture was stirred for 1 h. After removal of Hg, the whole was extracted with ethyl acetate (20 ml×2). The combined extracts were washed with brine (20 ml), dried over magnesium sulfate, filtered and concentrated in vacuo. The residue was purified by column chromatography (Si, 230–400 mesh/dichloromethane:methanol=50:1) to give a colorless oil (0.21 g/28%).

¹H NMR (CDCl₃) δ 7.33–7.28 (m, 5H), 3.50 (s, 2H), 2.70–2.30 (m, 10H), 1.78–1.20 (m, 12H) ppm.

C. 1-[2-(1-Piperazinyl)ethyl]cyclohexanol

This compound was prepared by a procedure similar to that described in example 1-C as a yellow amorphous.

¹H NMR (CDCl₃) δ 2.91–2.87 (m, 4H), 2.63–2.50 (m, 6H),1.70–1.25 (m, 12H) ppm.

D. Dimethyl 4-(2,6-dichlorophenyl)-2-[2-[4-[2-(1-hydroxycyclohexyl)ethyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow amorphous.

Free base

¹H NMR (CDCl₃) δ: 8.27 (br s, 1H), 7.71 (d, J=3.3 Hz, 1H), 7.24 (d, J=7.9 Hz, 2H), 7.20 (d, J=3.3 Hz, 1H), 7.00 (t, J=7.9 Hz, 1H), 5.99 (s, 1H), 4.15 (d, J=15.0 Hz, 1H), 3.74 (d,

J=15.0 Hz, 1H), 3.75–3.50 (m, 4H), 3.55 (s, 3H), 3.53 (s, 3H), 3.40–3.23 (m, 3H), 3.08–2.96 (m, 1H), 2.70–2.38 (m, 6H), 1.80–1.20 (m, 12H) ppm.
HCl salt
mp: 188–190° C. (dec.)
IR(KBr)$v_{max}$: 2936, 1693, 1512, 1433, 1294, 1188, 1103, 768 cm$^{-1}$.
MS (m/z): 705 (M+H)$^+$ Example 29

Dimethyl 4-(2,6-dichlorophenyl)-2-[2-[4-[3-(2-methyl-5-oxo1-pyrrolidinyl)propyl]-1-piperazinyl]-2-oxoethyl]-6-[2-(1,3-thiazol-2-yl)ethyl]-1,4-dihydro-3,5-pyridinedicarboxylate A. 1-[3-(4-Benzyl-1-piperazinyl)propyl]-5-methyl-2-pyrrolidinone A solution of 5-methyl-2-pyrrolidinone (0.99 g/10.0 mmol) in tetrahydrofuran (10 ml) was added to a suspension of sodium hydride(60% in oil, 0.6 g/1 5.0 mmol) in tetrahydrofuran (50 ml) at 0° C. and the resulting mixture was stirred for 1 hour at ambient temperature. To the mixture was added a solution of 1,3-dibromopropane (5.1 ml/50.0 mmol) in tetrahydrofuran (10 ml) and the mixture was stirred for 1 day. The mixture was poured into water (50 ml) and extracted with ethyl acetate (50 ml×2). The combined extracts were washed with brine (50 ml), dried over magnesium sulfate, filtered and concentrated in vacuo. The residue was purified by column chromatography (Si, 230–400 mesh/dichloromethane:methanol=30:1) to give as a mixture of 1-(3-bromoproyl)-5-methyl-2-pyrrolidinone and 1-allyl-5-methyl-2-pyrrolidinone (0.8 g). The mixture was dissolved with ethanol (5 ml). To the solution was added 1-benzylpiperazine (0.4 mV/2.19 mmol), and the mixture was stand for 7 days. The solvent was removed in vacuo. The residue was dissolved in dichloromethane (20 ml) and 2N-NaOH (20 ml). The aqueous layer was extracted with dichloromethane (20 ml). The combined extracts were washed with brine (20 ml), dried over magnesium sulfate, filtered and concentrated in vacuo. The residue was purified by column chromatography (Si, 230–400 mesh/dichloromethane:methanol=30:1–15:1) to give as the titled compound (0.59 g/19%).
$^1$H NMR (CDCl$_3$) δ 7.32–7.28 (m, 5H), 3.73–3.53 (m, 2H), 3.50 (s, 2H), 3.03–2.90 (m, 1H), 2.52–2.10 (m, 12H), 1.80–1.50 (m, 4H), 1.20 (d, J=7.2 Hz, 3H) ppm.
B. 1-[3-(1-Piperazinyl)propyl]-5-methyl-2-pyrrolidinone
This compound was prepared by a procedure similar to that described in example 1-C as a yellow oil.
$^1$H NMR (CDCl$_3$) δ 3.73–3.53 (m, 2H), 3.04–2.84 (m, 5H), 2.46–2.11 (m, 8H), 1.85–1.50 (m, 4H), 1.21 (d, J=6.3 Hz, 3H) ppm.
C. Dimethyl 4-(2,6Dichlorophenyl)-2-[2-[4-[3-(2-methyl-5-oxo-1-pyrrolidinyl)propyl]-1-piperazinyl]-2-oxoethyl]-6-[2-(1,3-thiazol-2-yl)ethyl]-1,4-dihydro-3,5-pyridinedicarboxylate
This compound was prepared by a procedure similar to that described in example 1-D as a yellow amorphous.
Free base
$^1$H NMR (CDCl$_3$) δ: 8.33 (br s, 1H), 7.72 (d, J=3.4 Hz, 1H), 7.24 (d, J=7.8 Hz, 2H), 7.20 (d, J=3.4 Hz, 1H), 7.00 (t, J=7.9 Hz, 1H), 5.99 (s, 1H), 4.10 (d, J=14.9 Hz, 1H), 3.80 (d, J=14.9 Hz, 1H), 3.75–3.55 (m, 6H), 3.55 (s, 3H), 3.54 (s, 3H), 3.40–3.23 (m, 3H), 3.07–2.92 (m, 2H), 2.50–2.10 (m, 8H), 1.80–1.50 (m, 4H), 1.21 (d, J=6.3 Hz, 3H) ppm.
HCl salt
mp: 188–193° C. (dec.)
IR (KBr)$v_{max}$: 3420, 1693, 1653, 1510, 1433, 1294, 1188, 1103, 768 cm$^{-1}$.
MS (m/z): 718 (M+H)$^+$ Example 30

Dimethyl 4-(2,6-dichlorophenyl)-2-[2-[4-[3-(3-methyl-2-oxo-1-pyrrolidinyl)propyl]-1-piperazinyl]-2-oxoethyl]-6-[2-(1,3-thiazol-2-yl)ethyl]-1,4-dihydro-3,5pyridinedicarboxylate A. 1-[3-(4-Benzyl-1-piperazinyl)propyl]-3-methyl-2-pyrrolidinone
This compound was prepared by a procedure similar to that described in example 29-A as a yellow oil.
$^1$H NMR (CDCl$_3$) δ 7.32–7.28 (m, 5H), 3.50 (s, 2H), 3.33–3.24 (m, 2H), 2.55–2.15 (m, 13H), 1.75–1.45 (m, 4H), 1.19 (d, J=7.3 Hz, 3H) ppm.
B. 1-[3-(1-Piperazinyl)propyl]-3-methyl-2-pyrrolidinone
This compound was prepared by a procedure similar to that described in example 1-C as a yellow oil.
$^1$H NMR (CDCl$_3$) δ 3.33–3.20 (m, 4H), 2.92–2.80 (m, 4H), 2.50–2.10 (m, 7H), 1.76–1.50 (m, 4H), 1.23–1.11 (m, 3H) ppm.
C. Dimethyl 4-(2,6-dichlorophenyl)-2-[2-[4-[3-(3-methyl-2-oxo-1-pyrrolidinyl)propyl]-1-piperazinyl]-2-oxoethyl]-6-[2-(1,3-thiazol-2-yl)ethyl]-1,4-dihydro-3,5-pyridinedicarboxylate
This compound was prepared by a procedure similar to that described in example 1-D as a yellow amorphous.
Free base
$^1$H NMR (CDCl$_3$) δ: 8.36 (br s, 1H), 7.72–7.70 (m, 1H), 7.23–7.19 (m, 3H), 7.00 (t, J=7.9 Hz, 1H), 6.00 (s, 1H), 4.08 (d, J=15.0 Hz, 1H), 3.79 (d, J=15.0 Hz, 1H), 3.68–3.53 (m, 4H), 3.55 (s, 3H), 3.53 (s, 3H), 3.42–3.22 (m, 5H), 3.11–2.95 (m, 1H), 2.50–2.20 (m, 7H), 1.77–1.55 (m, 4H), 1.19 (d, J=7.1 Hz, 3H) ppm.
HCl salt
IR (KBr)$v_{max}$: 1684, 1508, 1435, 1294, 1186, 1103, 768 cm$^{-1}$.
MS (m/z): 718 (M+H)$^+$
mp: 175–178° C. (dec.)

Example 31

Dimethyl 2-[2-[4-[3-[acetyl(ethyl)amino]propyl]-1-piperazinyl]-2-oxoethyl]4-(2,6dichlorophenyl)-6-[2-(1,3-thiazol-2-yl)ethyl]-1,4-dihydro-3,5-pyridinedicarboxylate A. 1-[2-(4-Benzyl-1-piperazinyl)ethyl]cyclopentylamine
CeCl$_3$ (50.0 g,/203 mmol) was dried in vacuo for 20 hours at 150° C. After cooling to room temperature, tetrahydrofuran (500 ml) was added under nitrogen and the resulting suspension was stirred for 1 d. After cooling to −78° C., to the suspension was added dropwise butanediyl dilithium in diethylether (90 mmol), which was prepared according to the literature (J. Org. Chem., 1990, 55, 5406) and the mixture was stirred for 1 hour. To the mixture was added dropwise a solution of 3-(4-benzyl-1-piperazinyl) propanenitrile (16.0 g/70.0 mmol) in tetrahydrofuran (100 ml) and stirred for 1 d at room temperature. The mixture was poured into 2 N—NaOH (200 ml) and the whole was extracted with dichloromethane (200 ml×2). The combined extracts were washed with brine, dried over magnesium sulfate, filtered and concentrated in vacuo. The residue was purified by column chromatography (NH$_2$ gel, 230–400 mesh/dichloromethane) to give a mixture of the titled compound and 1-benzylpiperazine (5.9 g).
$^1$H NMR (CDCl$_3$) δ 7.32–7.28 (m, 5H), 3.51 (s, 2H), 2.60–2.30 (m, 10H), 1.80–1.40 (m, 10H) ppm.
B. N-[1-[2-(4-Benzyl-1-piperazinyl)ethyl]cyclopentyl] acetamide This compound was prepared by a procedure similar to that described in example 4 as a yellow oil.
$^1$H NMR (CDCl$_3$) δ 7.48 (br s, 1H), 7.33–7.28 (m, 5H), 3.50 (s, 2H), 2.60–2.36 (m, 10H), 2.30–2.15 (m, 2H), 1.89 (s, 3H), 1.88–1.68 (m, 4H), 1.65–1.40 (m, 4H) ppm.

C. N-[1-[2-(4-Benzyl-1-piperazinyl)ethyl]cyclopentyl]-N-ethylamine

This compound was prepared by a procedure similar to that described in example 2-A as a yellow oil.
$^1$H NMR (CDCl$_3$) δ 7.32–7.28 (m, 5H), 3.51 (s, 2H), 2.65–2.30 (m, 12H), 1.75–1.40 (m, 10H), 1.06 (t, J=7.0 Hz, 3H) ppm.

D. N-[1-[2-(4-Benzyl-1-piperazinyl)ethyl]cyclopentyl]-N-ethylacetamide

This compound was prepared by a procedure similar to that described in example 4 as a yellow oil.
$^1$H NMR (CDCl$_3$) δ 7.32–7.28 (m, 5H), 3.50 (s, 2H), 3.29 (q, J=7.1 Hz, 2H), 2.58–2.32 (m, 8H), 2.32–2.21 (m, 2H), 2.09 (s, 3H), 2.05–1.92 (m, 4H), 1.92–1.75 (m, 2H), 1.75–1.50 (m, 4H), 1.20 (t, J=7.1 Hz, 3H) ppm.

E. N-[1-[2-(1-Piperazinyl)ethyl]cyclopentyl]-N-ethylacetamide

This compound was prepared by a procedure similar to that described in example 1-C as a yellow oil.
$^1$H NMR (CDCl$_3$) δ 3.29 (q, J=7.1 Hz, 2H), 3.11–2.99 (m, 4H), 2.66–2.50 (m, 4H), 2.36–2.27 (m, 2H), 2.19–1.97 (m, 4H), 2.11 (s, 3H), 1.92–1.77 (m, 2H), 1.74–1.51 (m, 4H), 1.21 (t, J=7.1 Hz, 3H) ppm.

F. Dimethyl 2-[2-[4-[3-[acetyl(ethyl)amino]propyl]-1-piperazinyl]-2-oxoethyl]-4-(2,6-dichlorophenyl)-6-[2-(1,3-thiazol-2-yl)ethyl]-1,4dihydro-3,5-pyridinedicarboxylate This compound was prepared by a procedure similar to that described in example 1-D as a yellow amorphous.
Free base
$^1$H NMR (CDCl$_3$) δ: 8.33 (br s, 1H), 7.71 (d, J=3.4 Hz, 1H), 7.23 (d, J=7.9 Hz, 2H), 7.20 (d, J=3.4 Hz, 1H), 6.99 (t, J=7.9 Hz, 1H), 5.99 (s, 1H), 4.07 (d, J=15.1 Hz, 1H), 3.81 (d, J=15.1 Hz, 1H), 3.70–3.50 (m, 4H), 3.55 (s, 3H), 3.54 (s, 3H), 3.42–3.23 (m, 5H), 3.11–2.95 (m, 1H), 2.50–2.23 (m, 6H), 2.20–2.10 (m, 2H), 2.10 (s, 3H), 2.05–1.95 (m, 2H), 1.95–1.80 (m, 4H), 1.78–1.50 (m, 4H), 1.21 (t, J=7.0 Hz, 3H) ppm.
HCl salt
mp: 175–178° C. (dec.)
IR(KBr)ν$_{max}$: 1697, 1508, 1435, 1292, 1186, 1103, 768cm$^{-1}$.
MS (m/z): 760 (M+H)$^+$ Example 32

Dimethyl 2-[2-[4-[[1-[(acetyl(ethyl)amino)methyl]cyclopentyl]methyl]-1-piperazinyl]-2-oxoethyl]-4-(2,6-dichlorophenyl)-1,4-dihydro-3,5-pyridinedicarboxylate A. N-[[1-[(4-Benzyl-1-piperazinyl)methyl]cyclopentyl]methyl]acetamide This compound was prepared by a procedure similar to that described in example 4 as a yellow amorphous.
$^1$H NMR (CDCl$_3$) δ 8.18 (br s, 1H), 7.32–7.28.(m, 5H), 3.51 (s, 2H), 3.18 (d, J=5.1 Hz, 2H), 2.65–2.32 (m, 10H), 1.95 (s, 3H), 1.80–1.20 (m, 8H) ppm.

B. N-[[1-[(4-Benzyl-1-piperazinyl)methyl]cyclopentyl]methyl]-N-ethylamine

This compound was prepared by a procedure similar to that described in example 2-A as a yellow amorphous.
$^1$H NMR (CDCl$_3$) δ 7.32–7.28 (m, 5H), 3.48 (s, 2H), 2.64–2.36 (m, 12H), 2.31 (s, 2H), 1.62–1.22 (m, 8H), 1.99 (t, J=7.1 Hz, 3H) ppm.

C. N-[[1-[(4-Benzyl-1-piperazinyl)methyl]cyclopentyl]methyl]-N-ethylacetamide

This compound was prepared by a procedure similar to that described in example 4 as a yellow amorphous.
$^1$H NMR (CDCl$_3$) δ 7.32–7.28 (m, 5H), 3.53–3.26 (m, 6H), 2.59–2.33 (m, 8H), 2.28–2.15 (m, 2H), 2.12 (s, 3H), 1.81–1.00 (m, 11H) ppm.

D. N-[[1-[(1-Piperazinyl)methyl]cyclopentyl]methyl]-N-ethylacetamide

This compound was prepared by a procedure similar to that described in example 1-C as a yellow amorphous.
$^1$H NMR (CDCl$_3$) δ 3.50–3.32 (m, 4H), 2.90–2.82 (m, 4H), 2.52–2.42 (m, 4H), 2.25–2.10 (m, 5H), 1.78–1.26 (m, 8H), 1.19–1.06 (m, 3H) ppm.

E. Dimethyl 2-[2-[4-[[1-[(acetyl(ethyl)amino)methyl]cyclopentyl]methyl]-1-piperazinyl]-2-oxoethyl]-4-(2,6-dichlorophenyl)-1,4-dihydro-3,5-pyridinedicarboxylate This compound was prepared by a procedure similar to that described in example 1-D as a yellow amorphous.
Free base
$^1$H NMR (CDCl$_3$) δ: 8.37–8.29 (m, 1H), 7.72 (d, J=3.4 Hz, 1H), 7.24 (d, J=8.0 Hz, 1H), 7.21 (d, J=3.4 Hz, 1H), 7.00 (t, J=7.9 Hz, 1H), 6.00 (s, 1H), 4.12–4.01 (m, 1H), 3.88–3.77 (m, 1H), 3.70–3.51 (m, 4H), 3.55 (s, 3H), 3.54 (s, 3H), 3.47–3.25 (m, 7H), 3.09–2.96 (m, 1H), 2.57–2.40 (m, 4H), 2.32–2.20 (m, 2H), 2.12 (s, 3H), 1.78–1.29 (m, 8H), 1.19–1.07 (m, 3H) ppm.
HCl salt
mp: 152–155° C. (dec.)
IR(KBr)ν$_{max}$: 1693, 1633, 1515, 1433, 1292, 1188, 1101, 768cm$^{-1}$.
MS (m/z): 760 (M+H)$^+$ Example 33

Dimethyl 4-(2,6-dichlorophenyl)-2-[2-oxo-2-[4-[2-[1-(2-oxo-1-pyrrolidinyl)cyclopentyl]ethyl]-1-piperazinyl]ethyl]-6-[2-(1,3-thiazol-2-yl)ethyl]-1,4-dihydro-3,5-pyridinedicarboxylate A. Ethyl 4-[[1-[2-(4-benzyl-1-piperazinyl)ethyl]cyclopentyl]amino]butanoate A mixture (1.00 g) of 1-[2-(4-benzyl-1-piperazinyl)ethyl]cyclopentylamine (example 31-A) and 1-benzylpiperazine was dissolved in dimethylformamide(10 ml). To the solution was added ethyl 4-bromobutylate (0.5 ml/3.48 mmol) and the mixture was stirred for 20 hours at 100° C. The solvent was removed in vacuo and the residue was purified by column chromatography (NH$_2$ gel, 230–400 mesh/150 g/dichloromethane) to give a yellow oil (390 mg).
$^1$H NMR (CDCl$_3$) δ 7.32–7.28 (m, 5H), 4.12 (q, J=7.1 Hz, 2H), 3.51 (s, 2H), 2.65–2.30 (m, 14H), 1.82–1.39 (m, 12H), 1.25 (t, J=7.1 Hz, 3H) ppm.

B. 1-[1-[2-(4-Benzyl-1-piperazinyl)ethyl]cyclopentyl]-2-pyrrolidinone

A mixture of ethyl 4-[[1-[2-(4-benzyl-1-piperazinyl)ethyl]cyclopentyl]amino]butanoate (333 mg/0.83 mmol) and 2 N—NaOH (1.3 ml/2.6 mmol) in dioxane (6 ml) was stirred for 8 hours at 80° C., and then the mixture was acidified with sat.NaH$_2$PO$_4$ (10 ml). The mixture was concentrated in vacuo. The residue was suspended in dichloromethane-methanol (5:1, 30 ml) and the mixture was refluxed for 1 hour. After filtration, the filtrate was concentrated in vacuo. The residue was dissolved in dichloromethane (20 ml). To the mixture was added WSC (431 mg/2.25 mmol) and the mixture was refluxed for 2 d. After cooling to room temperature, the mixture was washed with water (10 ml×2). The combined extracts were washed with brine (10 ml), dried over magnesium sulfate, filtered and concentrated in vacuo. The residue was purified by column chromatography (Si, 230–400 mesh/dichloromethane:methanol=30:1–15:1) to give a yellow oil (150 mg/ 51%).

$^1$H NMR (CDCl$_3$) δ 7.32–7.28 (m, 5H), 3.56 (s, 2H), 3.49 (t, J=6.9 Hz, 2H), 2.88–2.52 (m, 10H), 2.35 (t, J=8.1 Hz, 2H), 2.22–2.08 (m, 4H), 2.04–1.60 (m, 8H) ppm.

C. 1-[1-[2-(1-Piperazinyl)ethyl]cyclopentyl]-2-pyrrolidinone

This compound was prepared by a procedure similar to that described in example 1-C as a yellow oil.

MS (m/z): 265 (M)$^+$

D. Dimethyl 4-(2,6-dichlorophenyl)-2-[2-oxo-2-[4-[2-[1-(2-oxo-1-pyrrolidinyl)cyclopentyl]ethyl]-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow amorphous.

Free base $^1$H NMR (CDCl$_3$) δ: 8.31 (br s, 1H), 7.71 (d, J=3.3 Hz, 1H), 7.23 (d, J=7.8 Hz, 2H), 7.20 (d, J=3.3 Hz, 1H), 6.99 (t, J=7.8 Hz, 1H), 5.99 (s, 1H), 4.07 (d, J=15.0 Hz, 1H), 3.81 (d, J=15.0 Hz, 1H), 3.64–3.54 (m, 4H), 3.55 (s, 3H), 3.54 (s, 3H), 3.43 (t, J=6.9 Hz, 2H), 3.39–3.24 (m, 3H), 3.07–2.95 (m, 1H), 2.43–2.30 (m, 6H), 2.25–2.10 (m, 2H), 2.08–1.90 (m, 4H), 1.88–1.60 (m, 8H) ppm.

HCl salt mp: 175–180° C. (dec.)

IR (KBr)ν$_{max}$: 1692, 1510, 1433, 1294, 1188, 1103 cm$^{-1}$.

MS (m/z): 758 (M+H)$^+$

Example 34

Dimethyl 4-(2,6-dichlorophenyl)2-[2-[4-[2-[1-(diethylamino)cyclopentyl]ethyl]-1-piperazinyl]-2-oxoethyl]-6-[2-(1,3-thiazol-2-yl)ethyl]-1,4-dihydro-3,5-pyridinedicarboxylate A. N-[1-[2-1(4-Benzyl-1-piperazinyl)ethyl]cyclopentyl]-N,N-diethylamine This compound was prepared by a procedure similar to that described in example 2-A as a yellow oil.

$^1$H NMR (CDCl$_3$) δ 7.32–7.28 (m, 5H), 3.51 (s, 2H), 2.59–2.33 (m, 14H), 1.70–1.47 (m, 10H), 1.00 (t, J=6.9 Hz, 6H) ppm.

B. N-[1-[2-[(1-Piperazinyl)ethyl]cyclopentyl]-N,N-diethylamine

This compound was prepared by a procedure similar to that described in example 1-C as a yellow oil.

MS (m/z): 253 (M)$^+$

C. Dimethyl 4-(2,6-dichlorophenyl)-2-[2-[4-[2-1-(diethylamino)cyclopentyl]ethyl]-1-piperazinyl]-2-oxoethyl]-6-[2-(1,3-thiazol-2-yl)ethyl]-1,4-dihydro-3,5-pyridinedicarboxylate This compound was prepared by a procedure similar to that described in example 1-D as a yellow amorphous.

Free base $^1$H NMR (CDCl$_3$) δ: 8.35 (br s, 1H), 7.72 (d, J=3.3 Hz, 1H), 7.23 (d, J=7.9 Hz, 2H), 7.20 (d, J=3.3 Hz, 1H), 6.99 (t, J=7.9 Hz, 1H), 6.00 (s, 1H), 4.12 (d, J=15.0 Hz, 1H), 3.79 (d, J=15.0 Hz, 1H), 3.72–3.55 (m, 4H), 3.55 (s, 3H), 3.54 (s, 3H), 3.40–3.25 (m, 3H), 3.10–2.97 (m, 1H), 2.58–2.34 (m, 10H), 1.72–1.42 (m, 10H), 1.01 (t, J=7.0 Hz, 6H) ppm.

HCl salt mp: 195–200° C. (dec.)

IR (KBr)ν$_{max}$: 1693, 1510, 1433, 1296, 1188, 1103 cm$^{-1}$.

MS (m/z) : 746 (M+H)$^+$

Example 35

Dimethyl 4-(2,6-dichlorophenyl)-2-[2-oxo-[4-[4-(2-oxo-1-pyrrolidinyl)butyl]-1-piperazinyl]ethyl]-6-[2-(1,3-thiazol-2-yl)ethyl]-1,4-dihydro-3,5-pyridinedicarboxylate A. 1-(4-Bromobutyl)-2-pyrrolidinone To a suspension of sodium hydride(555 mg/13.9 mmol) in tetrahydrofuran (50 ml) was added 2-pyrrolidinone (0.7 ml/9.26 mmol) at ice-cooling temperature. The mixture was stirred for 1 h at ambient temperature, and then 1,4-dibromobutane (10 g/46.3 mmol) was added at the same temperature. The resulting mixture was stirred overnight. Water (10 ml) was added to the mixture and the mixture was extracted with ethyl acetate (50 ml×2). The combined extracts were washed with water and brine succesively, then dried over magnesium sulfate, filtered and concentrated. The residue was purified by column chromatography (80g/dichloromethane:methanol=100:0–100:5–100:10) to give a colorless oil(2.0 g/90%).

$^1$H NMR (CDCl$_3$) δ: 3.50–3.24 (m, 6H), 2.45–2.30 (m, 2H), 2.10–1.93 (m, 2H), 1.93–1.77 (m, 2H), 1.77–1.60 (m, 2H) ppm.

B. 1-[4-(4-benzyl-1-piperazinyl)butyl]-2-pyrrolidinone

A mixture of 1-(4-bromobutyl)-2-pyrrolidinone (2.0 g/9.1 mmol) and benzylpiperazine (1.58 ml/9.1 mmol) in ethanol (4.5 ml) was stirred overnight at ambient temperature. The mixture was basified with 2 N NaOH and extracted with dichloromethane (50 ml×2). The combined extracts were washed with brine, dried over magnesium sulfate, filtered and concentrated. The residue was purified by column chromatography (100 g/dichloromethane=100:5–100:10) to give a pale yellow oil (1.6 g/56%).

$^1$H NMR (CDCl$_3$) δ: 7.34–7.20 (m, 5H), 3.51 (s, 2H), 3.36 (t, J=6.9 Hz, 2H), 3.28 (t, J=6.9 Hz, 2H), 3.50–3.24 (m, 6H), 2.55–2.30 (m, 10H), 2.80–1.20 (m, 2H), 1.60–1.42 (m, 6H) ppm.

MS(EI) 315 (M$^+$)

C. 1-[4-(1-Piperazinyl)butyl-2-pyrrolidinone

This compound was prepared by a procedure similar to that described in example 1-C as a yellow solid.

$^1$H NMR (CDCl$_3$) δ: 3.45–3.22 (m, 4H), 2.94–2.82 (m, 4H), 2.45–2.75 (m, 8H), 2.08–1.92 (m, 2H), 1.70–1.40 (m, 5H) ppm.

D. Dimethyl 4-(2,6-dichlorophenyl)-2-[2-oxo-[4-[[4-(2-oxo-1-pyrrolidinyl)butyl]-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow solid.

Free base $^1$H-NMR (CDCl$_3$) δ 8.35 (br s, 1H), 7.72 (d, J=3.3 Hz, 1H), 7.23 (d, J=8.2 Hz, 2H), 7.21 (d, J=3.5 Hz, 1H), 7.00 (t, J=8.2 Hz, 1H), 6.00 (s ,1H), 4.09 (d, J=15.0 Hz, 1H), 3.81 (d, J=15.1 Hz, 1H), 3.66–3.58(m, 4H), 3.55 (s, 3H), 3.53 (s, 3H), 3.42–3.26 (m, 7H), 3.05–2.96 (m, 1H), 2.46–2.32 (m, 10H), 2.08–1.96 (m, 2H), 1.60–1.45(m, 4H) ppm.

HCl salt (Amorphous)

IR (KBr)ν$_{max}$: 3568, 3088, 2941, 1686, 1655, 1508, 1431, 1294, 1188, 1103 cm$^{-1}$.

$^1$H-NMR (DMSO-d$_6$) δ 9.17 (br s, 1H), 7.72 (d, J=3.5 Hz, 1H), 7.62 (d, J=3.3 Hz, 1H), 7.36 (d, J=8.2 Hz, 2H), 7.17 (t, J=7.4 Hz, 1H), 5.87 (s, 1H), 4.50–3.95 (m, 3H), 3.60–3.30 (m, 12H), 3.25–3.05 (m, 8H), 2.90–2.75 (m, 1H), 2.22 (t, J=7.9 Hz, 2H), 2.00–1.87 (m, 2H), 1.70–1.45 (m, 4H) ppm.

MS (m/z): 718 (M+H)$^+$, 716 (M–H)$^-$

Example 36

Dimethyl 4-(2,6-dichlorophenyl)-2-[2-[4-[4-methyl4-(2-oxo-1-pyrrolidinyl)pentyl]-1-piperazinyl]-2-oxoethyl]-6-[2-(1,3-thiazol-2-yl)ethyl-1,4-dihydro-3,5-pyridinedicarboxylate A. 4-(4-Benzyl-1-piperazinyl)-1,1-dimethylbutylamine This compound was prepared by a procedure similar to that described in example 20-A as a yellow oil.

¹H NMR (CDCl₃) δ 7.34–7.20 (m, 5H), 3.51 (s, 2H), 2.60–2.45 (m, 6H), 2.32 (t, J=7.4 Hz, 2H), 1.60–1.29 (m, 6H), 1.09 (s, 6H) ppm.

B. N-[4-(4-Benzyl-1-piperazinyl)-1,1-dimethylbutyl]-4-chlorobutanamide

This compound was prepared by a procedure similar to that described in example 20-B as a yellow oil.

¹H NMR (CDCl₃) δ 7.34–7.15 (m, 5H), 5.80 (brs, 1H), 4.35 (t, J=6.9 Hz, 1H), 3.59 (t, J=6.9 Hz, 1H), 3.52 (s, 2H), 2.56–2.45 (m, 4H), 2.40–2.20 (m, 4H), 2.16–2.05 (m, 2H), 1.69–1.45 (m, 4H), 1.32 (s, 6H) ppm.

C. N-[4-(4-Benzyl-1-piperazinyl)-1,1-dimethylbutyl]-2-pyrrolidinone

This compound was prepared by a procedure similar to that described in example 20-C as a yellow oil.

¹H NMR (CDCl₃) δ 7.33–7.23 (m, 5H), 3.51 (s, 2H), 3.47 (t, J=6.9 Hz, 2H), 2.54–2.28 (m, 12H), 1.96–1.77 (m, 4H), 1.75 (s, 3H), 1.54–1.38 (m, 4H), 1.34 (s, 3H) ppm.

D. Dimethyl 4-(2,6-dichlorophenyl)-2-[2-[4-[4-methyl-4-(2-oxo-1-pyrrolidinyl)pentyl]-1-piperazinyl]-2-oxoethyl]-6-]2-(1,3-thiazol-2-yl)ethyl]-1,4-dihydro-3,5-pyridinedicarboxylate This compound was prepared by a procedure similar to that described in example 1-C and D as a yellow oil.

Free base

¹H-NMR (CDCl₃) δ 8.34 (s, 1H), 7.72 (d, J=3.5 Hz, 1H), 7.26 (d, J=4.6 Hz, 1H), 7.24 (d, J=7.9 Hz, 2H), 7.21 (d, J=3.5 Hz, 11H), 6.99 (t, J=7.9 Hz, 11H), 5.99 (s ,1H), 4.08 (d, J=15.0 Hz, 1H), 3.82 (d, J=15.0 Hz, 1H), 3.70–3.57(m, 4H), 3.55 (s, 3H), 3.53 (s, 3H), 3.44 (t, J=6.9 Hz, 2H), 3.38–3.24 (m, 3H), 3.19 (s, 2H), 3.05–2.96 (m, 1H), 2.50–2.33 (m, 8H), 2.08–1.94 (m, 2H), 1.68–1.58 (m, 4H), 1.52–1.43 (m, 6H) ppm.

HCl salt mp 156–160° C.(dec.)

IR(KBr)ν$_{max}$: 3437, 2949, 1686, 1655, 1508, 1433, 1294, 1186, 1103 cm$^{-1}$.

¹H-NMR (DMSO-d₆) δ 9.35–9.25 (m, 1H), 7.71 (d, J=3.3 Hz, 11), 7.61 (d, J=3.3 Hz, 1H), 7.36 (d, J=8.2 Hz, 2H), 7.16 (t, J=8.2 Hz, 1H), 5.87 (s, 1H), 4.50–4.00(m, 3H), 3.60–2.80 (m, 12H) 2.26 (t, J=7.9 Hz, 2H), 1.96–1.87 (m, 2H), 1.64–1.57 (m, 6H), 1.48–1.40 (m, 4H) ppm.

MS (m/z) 746 (M+H)⁺, 744 (M-H)⁻

Example 37

Dimethyl 4-(2,6-dichlorophenyl)-2-[2-oxo-2-[4-[2-[1-[2-oxo-1-pyrrolidinyl)methyl]cyclopentyl]ethyl]-1-piperazinyl]ethyl]-6-[2-(1,3-thiazol-2-yl)ethyl]-1,4-dihydro-3,5-pyridinedicarboxylate A. 4-[(4-Benzyl-1-piperazinyl)butanenitrile A mixture of 4-bromobutyronitrile (12.5g /84.5 mmol) and benzylpiperazine (13.5 g/76.8 mmol) in dimethylformamide(85 ml) was stirred at 100° C. for 10 hours. After cooling down, the mixture was extracted with ethyl acetate-toluene (3:1, 200 mL), and washed with water (100 mL), then dried over NaSO₄. After concentrated in vacuo, the residue was purified by column chromatography (NH₂ gel, 200–350 mesh/500 g/dichloromethane) to give a pale brown oil (14.6 g/71%).

¹H NMR (CDCl₃) δ 7.35–7.20 (m, 5H), 3.51 (s, 2H), 2.58–2.42 (m, 10H), 1.86–1.70 (m, 4H) ppm.

B. 1-[2-(4-Benzyl-1-piperazinyl)ethyl]cyclopentylcarbonitrile

To a solution of 4-[(4-benzyl-1-piperazinyl)butanenitrile (5.00 g/20.5 mmol) in tetrahydrofuran (68 ml) was added dropwise 2.0 M solution of lithium diisopropylamide (51 ml/103 mmol) at −78° C., and then the resulting mixture was stirred for 30 min. 1,5-Dibromobutane (4.2 ml/35 mmol) was added to the mixture in one portion and the resulting mixture was allowed to warm to ambient temperature. The mixture was stirred for 3 hours. Then, water (150 ml) was added for quenching. The mixture was extracted with ethyl acetate (200 ml×2). The combined extracts were washed with brine (50 ml), dried over magnesium sulfate, filtered and concentrated in vacuo. The residue was purified by column chromatography (NH₂ gel, 230–400 mesh/200 g/hexane:ethyl acetate=8:0–2:1) to give a yellow oil (4.9 g/80%).

¹H NMR (CDCl₃) δ 7.34–7.20 (m, 5H), 3.50 (s, 2H), 2.60–2.45 (m, 8H), 2.20–2.10 (m, 2H), 1.90–1.45 (m, 10H) ppm.

C. [1-[2-(4-Benzyl-1-piperazinyl)ethyl]cyclopentyl]methylamine

A suspension of 1-[2-(4-benzyl-1-piperazinyl)ethyl]cyclopentylcarbonitrile (4.96 g/16.3 mmol) and LAH (1.86 g/49.0 mmol) in dioxane (65 ml) was stirred at 90° C. for 3 hours. After cooling down, the excess reagent was quenched with 10water-Na₂SO₄ and the resulting gray suspension was stirred until the suspension turned to white suspension. The resulting suspension was filtered through a pad of Celite. The filtrate was dried over magnesium sulfate, filtered and concentrated in vacuo to give a yellow oil (4.9 g/quant.).

¹H NMR (CDCl₃) δ 7.34–7.20 (m, 5H), 3.50 (s, 2H), 2.52–2.26 (m, 10H), 1.68–1.50 (m, 8H), 1.40–1.32 (m, 4H) ppm D. N-[[1-[2-(4-Benzyl-1-piperazinyl)ethyl]cyclopentyl]methyl]-4-chlorobutanamide A solution of [1-[2-(4-benzyl-1-piperazinyl)ethyl]cyclopentyl]methylamine (675 mg, 2.32 mmol) and 4-chlorobutanoylchloride (491 mg, 3.48 mmol) in tetrahydrofuran (3.48 ml) and aqueous 2 N NaOH (1.74 ml) was stirred at ambient temperature for 15 hours. The organic layers were extracted with dichloromethane (10 ml), washed with brine (4 ml) and dried over magnesium sulfate filtered and concentrated in vacuo. The residue was purified by column chromatography (NH₂ gel, 230–400 mesh/30 g/hexane:ethyl acetate=1:1) to give a yellow oil (684 mg/75%).

¹H NMR (CDCl₃) δ 7.34–7.20 (m, 5H), 3.50 (s, 2H), 2.60–2.45 (m, 8H), 2.20–2.10 (m, 2H), 1.90–1.45 (m, 10H) ppm.

E. 1-[[1-[2-(4-Benzyl-1-piperazinyl)ethyl]cyclopentyl]methyl]-2-pyrrolidinone

To a stirred solution of N-[[1-[2-(4-benzyl-1-piperazinyl)ethyl]cyclopentyl]methyl]-4-chlorobutanamide (664 mg) in dimethylformamide(5.5 ml) was added sodium hydride (60% in oil, 98 mg) at room temperature and the mixture was stirred at 70° C. for 5 hours. After cooling down, water (3 ml) was added and the organic layers were extracted with ethyl acetate (15 ml). The extract was washed with brine (4 ml), dried over magnesium sulfate filtered and concentrated in vacuo. The residue was purified by column chromatography (NH₂ gel, 230–400 mesh/20 g/hexane:ethyl acetate= 2:1–1:2) to give a yellow oil (408 mg/67%).

¹H NMR (CDCl3) δ 7.33–7.23 (m, 5H), 3.50 (s, 2H), 3.47 (t, J=6.9 Hz, 2H), 2.52–2.32 (m, 10H), 2.40–1.92 (m, 2H), 1.84–1.78 (m, 4H), 1.66–1.44 (m, 8H) ppm.

F. 1-[[1-[2-(1-Piperazinyl)ethyl]cyclopentyl]methyl]-2-pyrrolidinone

A mixture of 1-[[1-[2-(4-benzyl-1-piperazinyl)ethyl]cyclopentyl]methyl]-2-pyrrolidinone (408 mg) and palladium hydroxide (41 mg) in methanol (5.5 ml) was stirred under hydrogen (4 kg) for 7 hours. After hydrogen was replaced with nitrogen, the mixture was filtered through Celite. The filtrate was concentrated in vacuo to provide a yellow oil. (345 mg/100%)

G. Dimethyl 4-(2,6-dichlorophenyl)-2-[2-oxo-2-[4-[2-[1-(2-oxo-1-pyrrolidinyl)methyl]cyclopentyl]ethyl]-1-piperazinyl]ethyl]-6-[2-(1,3-thiazol-2-yl)ethyl]-1,4-dihydro-3,5-pyridinedicarboxylate This compound was prepared by a procedure similar to that described in example 1-D as a yellow oil.

Free base
$^1$H-NMR (CDCl$_3$) δ 8.34 (br s, 1H), 7.72 (d, J=3.3 Hz, 1H), 7.26 (d, J=8.02 Hz, 2H), 7.20 (d, J=3.3 Hz, 1H), 6.99 (t, J=8.0 Hz, 1H), 5.99 (s ,1H), 4.08 (d, J=15.0 Hz, 1H), 3.82 (d, J=15.0 Hz, 1H), 3.73–3.55(m, 4H), 3.55 (s, 3H), 3.54 (s, 3H), 3.45–3.25 (m, 5H), 3.19 (s, 2H), 3.05–2.95 (m, 1H), 2.46–2.32 (m, 8H), 2.06–1.94 (m, 2H), 1.68–1.43 (m, 10H) ppm.

HCl salt
mp 153–160° C.(dec.)
IR (KBr)ν$_{max}$: 3427, 2949, 1686, 1655, 1508, 1431, 1294, 1188, 1103 cm$^{-1}$.
$^1$H-NMR (DMSO-d6) δ 9.36–9.24 (m, 1H), 7.71 (d, J=3.4 Hz, 1H), 7.61 (d, J=3.4 Hz, 1H), 7.36 (d, J=8.0 Hz, 2H), 7.17 (t, J=8.0 Hz, 1H), 5.87 (s, 1H), 4.45–4.40 (m, 3H), 3.60–3.35 (m, 12H), 3.25–3.06 (m, 6H), 2.90–2.75 (m, 1H), 2.26 (t, J=7.9 Hz, 2H), 1.96–1.88 (m, 2H), 1.66–1.39 (m, 10H) ppm.
MS (m/z): 772 (M+H)$^+$, 720 (M–H)$^-$ Example 38

Dimethyl 4-(2,6-dichlorophenyl)-2-[2-[4-[4-(4-morpholinyl)butyl]-1-piperazinyl]-2-oxoethyl]-6-[2-(1,3-thiazol-2-yl)ethyl]-1,4-dihydro-3,5-pyridinedicarboxylate A. 1-(4-Morpholinyl)4-(1-piperazinyl)butane This compound was obtained according to a similar manner to that of example2-A as a yellow solid.
$^1$H NMR (CDCl$_3$) δ 3.74–3.68 (m, 4H), 2.89 (t, J=4.9 Hz, 2H), 2.48–2.28 (m, 14H), 1.55–1.47 (m, 4H) ppm.

B. Dimethyl 4-(2,6-dichlorophenyl)-2-[2-[4-[4-(4-morpholinyl)butyl]-1-piperazinyl]-2-oxoethyl]-6-[2-(1,3-thiazol-2-yl)ethyl]-1,4-dihydro-3,5-pyridinedicarboxylate This compound was obtained according to a similar manner to that of example 1-D as a yellow solid.

Free base
$^1$H-NMR (CDCl$_3$) δ 8.38 (s, 1H), 7.71 (d, J=3.3 Hz, 1H), 7.31–7.19 (m, 3H), 7.00 (t, J=7.6 Hz, 1H), 6.00 (s ,1H), 4.08 (d, J=15.0 Hz, 1H), 3.82 (d, J=15.0 Hz, 1H), 3.78–3.57 (m, 8H), 3.55 (s, 3H), 3.53 (s, 3H), 3.40–3.25 (m, 5H), 3.10–2.95 (m, 1H), 2.48–2.32 (m, 12H), 1.58–1.48 (m, 4H) ppm.

HCl salt
mp 169–177° C.(dec.)
IR (KBr)ν$_{max}$: 3398, 2949, 2854, 1692, 1638, 1508, 1433, 1294, 1188, 1103 cm$^{-1}$.
$^1$H-NMR (DMSO-d$_6$) δ 9.48–9.28 (m, 1H), 7.72 (d, J=3.3 Hz, 1H), 7.62(d, J=3.3 Hz, 1H), 7.35 (d, J=8.6 Hz, 2H), 7.17 (t, J=8.6 Hz, 1H), 5.87 (s, 1H), 4.01–3.74 (m, 3H), 3.42–2.50 (m, 22H), 1.84–1.75 (m, 4H) ppm.
MS (m/z) 719 (M)$^+$ Example 39

Dimethyl 4-(2,6-dichlorophenyl)-2-[2-[4-[3-ethyl-3-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate A. 3-(4-Benzyl-1-piperazinyl)-1,1-diethylpropylamine To a stirred solution of ethyl iodide (5.69 g, 0.0365 mol) in diethylether was added a solution of tert-butyllithium (1.64M, 47 ml, 0.0767 mol) at –78° C. and the mixture was stirred for 2 h at –78° C. Then, the temperature was raised to 23° C. and the mixture was stirred for 1 h to provide ethyl lithium solution. This solution was added to dry CeCl$_3$ (15.1 g , 0.0365 mol of CeCl$_3$, 7H$_2$O was used to prepare dry CeCl$_3$.) in tetrahydrofuran at –78° C. and the mixture was stirred at –78° C. for 30 minutes. To the suspnsion was added the solution of 3-(4-benzyl-1-piperazinyl)propionitrile (2.40 g, 0.0104 mol) in tetrahydrofuran (2.0 ml) and the mixture was stirred at –65° C. for 1 hour, then the temperature was raised to room temperature. After the usual workup, flash chromatography (NH$_2$ gel, 230–400 mesh/1–10% methanol in dichloromethane) afforded a yellow oil (1.2 g, 40%).
$^1$H-NMR (CDCl$_3$) δ 7.33–7.20 (m, 5H), 3.51 (s, 2H), 2.56–2.34 (m, 10H), 1.50 (t, J=8.0 Hz, 2H), 1.35 (q, J=7.6 Hz, 4H), 0.83 (t, J=7.6 Hz, 6H) ppm.

B. N-[3-(4-Benzyl-1-piperazinyl)-1,1-diethylpropyl]-4-chlorobutanamide

This compound was obtained according to a similar manner to that of example 20-B as a yellow solid.
$^1$H-NMR (CDCl3) δ 7.91 (brs, 1H), 7.34–7.26 (m, 5H), 4.35 (t, J=7.1 Hz, 0.85H), 3.61 (t, J=7.1 Hz, 1.15H), 3.52 (s, 2H), 2.51–1.57 (m, 20H), 0.80 (t, J=7.6 Hz, 6H) ppm.

C. 1-[3-(4-Benzyl-1-piperazinyl)-1,1-diethylpropyl]-2-pyrrolidinone

This compound was obtained according to a similar manner to that of example 20-C as a yellow solid.
$^1$H-NMR (CDCl$_3$) δ 7.32–7.20 (m, 5H), 3.50 (s, 2H), 3.45 (t, J=7.1 Hz, 2H), 2.53–2.24 (m, 12H), 2.07–1.75 (m, 8H), 0.80 (t, J=7.6 Hz, 6H) ppm.

D. 1-[3-(1-Piperazinyl)-1,1-diethylpropyl]-2-pyrrolidinone

This compound was obtained according to a similar manner to that of example 1-C as a yellow solid.
$^1$H-NMR (CDCl$_3$) δ 3.40 (t, J=7.1 Hz, 2H), 2.86–2.79 (m, 3H), 2.45–2.17 (m, 9H), 2.03–1.65 (m, 8H), 0.80 (t, J=7.6 Hz, 6H) ppm.

E. Dimethyl 4-(2,6-dichlorophenyl)-2-[2-[4-[3-ethyl-3-(2-oxo-1-5-pyrrolidinyl)pentyl]-1-piperazinyl]-2-oxoethyl]-6-[2-(1,3-thiazol-2-yl)ethyl]-1,4-dihydro-3,5-pyridinedicarboxylate This compound was obtained according to a similar manner to that of example 1-D as a yellow solid.

Free base
$^1$H-NMR (CDCl$_3$) δ 8.35 (br s, 1H), 7.71 (d, J=3.3 Hz, 1H), 7.23 (d, J=7.9 Hz, 2H), 7.21 (d, J=3.3 Hz), 7.00 (t, J=7.90 Hz, 1H), 6.00 (s ,1H), 4.07 (d, J=15.0 Hz, 1H), 3.82 (d, J=15.0 Hz, 1H), 3.70–3.50 (m, 4H), 3.55 (s, 3H), 3.53 (s, 3H), 3.40–3.24 (m, 3H), 3.10–2.96 (m, 1H), 2.52–1.68 (m, 16H), 0.81 (t, J=7.1 Hz, 6H) ppm.

HCl salt.
mp 151–155° C.(dec.)
IR (KBr)ν$_{max}$: 3398, 2949, 1686, 1655, 1508, 1433, 1294, 1186, 1103 cm$^{-1}$.
MS (m/z): 760 (M+H)$^+$ Example 40

Dimethyl 4-(2,6-dichlorophenyl)-2-[2-[4-[2-1-[(diethylamino)methyl]cyclopentyl]ethyl]-1-piperazinyl]-2-oxoethyl]-6-[2-(1,3-thiazol-2-yl]ethyl]-1,4-dihydro-3,5-pyridinedicarboxylate A. 1-[2-(4-Benzyl-1-piperazinyl)ethyl]-N,N-diethylcyclopentanecarboxamide This compound was obtained according to a similar manner to that of example 1-D as a yellow solid.
$^1$H-NMR (CDCl$_3$) δ 7.32–7.15 (m, 5H), 3.48 (s, 2H), 3.45–3.25 (m, 4H), 2.50–2.40 (m, 4H), 2.32–2.15 (m, 2H), 1.80–1.72 (m, 2H), 1.63–1.53 (m, 4H), 1.20–1.05 (m, 6H) ppm.

B. N,N-Diethyl-1-[2-(1-piperazinyl)ethyl]cyclopentanecarboxamide

This compound was obtained according to a similar manner to that of example 1-C as a yellow solid.
¹H-NMR (CDCl₃) δ 3.45–3.25 (m, 4H), 2.98–2.91 (m, 4H), 2.50–2.43 (m, 4H), 2.34–2.16 (m, 4H), 1.80–1.72 (m, 2H), 1.63–1.53 (m, 6H), 1.20–1.05 (m, 6H) ppm.

C. N-Ethyl-N-[[1-[2-(1-piperazinyl)ethyl]cyclopentyl]methyl]-1-ethanamine

This compound was obtained according to a similar manner to that of example 2-A as a yellow solid.
¹H-NMR (CDCl₃) δ 2.93–2.87 (m, 3H), 2.58–1.98 (m, 13H), 1.62–1.30 (m, 10H), 0.96 (t, J=7.1 Hz, 6H) ppm.

D. Dimethyl 4-(2,6-dichlorophenyl)-2-[2-[4-[2-[1-[(diethylamino)methyl]cyclopentyl]ethyl]-1-piperazinyl]-2-oxoethyl]-6-[2-(1,3-thiazol-2-yl)ethyl]-1,4-dihydro-3,5-pyridinedicarboxylate This compound was obtained according to a similar manner to that of example 1-D as a yellow solid.
Free base
¹H-NMR (CDCl₃) δ 8.37 (br s, 1H), 7.72 (d, J=3.3 Hz, 1H), 7.23 (d, J=7.9 Hz, 2H), 7.21 (d, J=3.3 Hz), 6.99 (t, J=7.90 Hz, 1H), 6.00 (s ,1H), 4.10 (d, J=15.0 Hz, 1H), 3.80 (d, J=15.0 Hz, 1H), 3.72–3.58(m, 4H), 3.55 (s, 3H), 3.53 (s, 3H), 3.40–3.24 (m, 3H), 3.10–2.96 (m, 1H), 2.58–2.32 (m, 10H), 2.24 (s, 2H), 1.62–1.30 (m, 10H), 0.96 (t, J=7.1 Hz, 6H) ppm.
HCl salt.
mp 160–167° C.(dec.)
IR (KBr)ν$_{max}$: 3395, 3082, 2949, 1686, 1655, 1508, 1433, 1294, 1188, 1103 cm⁻¹.
MS (m/z): 760 (M+H)⁺

Example 41

Dimethyl 4-(2,6-dichlorophenyl)-2-[2-oxo-2-[4-[4-(2-oxo-1-piperidinyl)butyl]-1-piperazinyl]ethyl]-6-[2-(1,3-thiazol-2-yl)ethyl-1,4-dihydro-3,5-pyridinedicarboxylate A. 1-(4-Bromobutyl)-2-piperidinone To a suspension of sodium hydride (60% oil dispersion, 1.39 g, 0.0348 mol) in tetrahydrofuran (200 ml) and dimethylformamide(42 ml) was added a solution of 6-valerolactam (2.32 g, 0.0232 mol) in tetrahydrofuran (10 ml) at 0° C. After the mixture was stirred at room temperature for 1 h, 1,4-dibromobutane (13.8 ml, 0.116 mol) was added to the mixture at 0° C. After the mixture was stirred overnight at room temperature, water was added and the organic layers were extracted with ethyl acetate, dried over Na₂SO₄, filtered and concentrated in vacuo. The residue was purified by column chromatography (SiO₂, 200–350 mesh/50 g/hexane:ethyl acetate=3:1–2:1) to provide a yellow oil(3.8 g/70%).
¹H-NMR (CDCl₃) δ 3.48–3.36 (m, 4H), 3.45–3.30 (m, 2H), 2.40–2.34 (m, 2H), 1.92–1.65 (m, 8H) ppm.

B. 1-[4-(4-Benzyl-1-piperazinyl)butyl]-2-piperidinone

This compound was obtained according to a similar manner to that of example 35-A as a yellow solid.
¹H-NMR (CDCl₃) δ 7.35–7.21 (m, 5H), 3.50 (s, 2H), 3.38–3.32 (m, 2H), 3.28–3.22 (m, 2H), 2.50–2.32 (m, 12H), 1.55–1.45 (m, 4H) ppm.

C.1-[4-(1-Piperazinyl)butyl]-2-piperidinone

This compound was obtained according to a similar manner to that of example 1-C as a yellow solid.
¹H-NMR (CDCl₃) δ 3.40–3.23 (m, 4H), 2.92–2.86 (m, 4H), 2.42–2.28 (m, 8H), 1.80–1.75 (m, 4H), 1.60–1.44 (m, 4H ) ppm.

D. Dimethyl 4-(2,6-dichlorophenyl)-2-[2-oxo-2-[4-[4-(2-oxo-1-piperidinyl)butyl]-1-piperazinyl]ethyl]-6-[2-(1,3-thiazol-2-yl)ethyl-1,4-dihydro-3,5-pyridinedicarboxylate This compound was obtained according to a similar manner to that of example 1-D as a yellow solid.
HCl salt
mp 142–146° C.(dec.)
IR (KBr)ν$_{max}$: 3398, 2947, 1691, 1618, 1508, 1433, 1294, 1186, 1103 cm⁻¹.
¹H-NMR (DMSO-d₆) δ 9.03–9.01 (m, 1H), 7.60 (d, J=3.5 Hz, 1H), 7.49 (d, J=3.5 Hz, 1H), 7.24 (d, J=8.2 Hz, 2H), 7.04 (t, J=7.4 Hz, 1H), 5.75 (s, 1H), 4.40–3.80 (m, 3H), 3.50–2.90 (m, 13H) 2.80–2.60 (m, 2H), 2.20–2.00 (m, 2H), 1.70–1.35 (m, 10H) ppm.
MS (m/z): 732 (M+H)⁺
Free base
¹H-NMR (CDCl3) δ 8.36 (br s, 1H), 7.72 (d, J=3.3 Hz, 1H), 7.30–7.19 (m, 2H), 7.00 (t, J=8.2 Hz, 1H), 6.00 (s ,1H), 4.08 (d, J=15.0 Hz, 1H), 3.81 (d, J=15.1 Hz, 1H), 3.70–3.58 (m, 4H), 3.55 (s, 3H), 3.53 (s, 3H), 3.40–3.24 (m, 7H), 3.10–2.96 (m, 1H), 2.46–2.32 (m, 8H), 1.85–1.73 (m, 4H), 1.60–1.45 (m, 4H) ppm.

Example 42

Dimethyl 4-(2,6-dichlorophenyl)-2-[2-oxo-2-[4-[4-(1-piperidinyl)butyl]-1-piperazinyl]ethyl]-6-[2-(1,3-thiazol-2-yl)ethyl]-1,4-dihydro-3,5-pyridinedicarboxylate A. 1-[4-(1-Piperidinyl)butyl]piperazine This compound was obtained according to a similar manner to that of example 1-C as a yellow solid.
¹H-NMR (CDCl₃) δ 2.91–2.86 (m, 4H), 2.42–2.26 (m, 12H), 1.64–1.40 (m, 10H) ppm.

B, Dimethyl 4-(2,6-dichlorophenyl)-2-[2-oxo-2-[4-[4-(1-piperidinyl)butyl]-1-piperazinyl]ethyl]-6-[2-(1,3-thiazol-2-yl)ethyl]-1,4-dihydro-3,5-pyridinedicarboxylate This compound was obtained according to a similar manner to that of example 1-D as a yellow solid.
Free base
¹H-NMR (CDCl₃) δ 8.38 (br s, 1H), 7.72 (d, J=3.3 Hz, 1H), 7.24 (d, J=7.9 Hz, 2H), 7.20 (d, J=3.3 Hz), 7.00 (t, J=7.90 Hz, 1H), 6.00 (s ,1H), 4.09 (d, J=15.0 Hz, 1H), 3.82 (d, J=15.0 Hz, 1H), 3.70–3.58 (m, 4H), 3.55 (s, 3H), 3.53 (s, 3H), 3.40–3.24 (m, 3H), 3.05–2.90 (m, 1H), 2.46–2.25 (m, 12H), 1.65–1.40 (m, 10H) ppm.
HCl salt
mp 163–168° C.(dec.)
IR(KBr)ν$_{max}$: 3395, 2949, 2550, 1692, 1508, 1508, 1433, 1294, 1188, 1103 cm⁻¹.
¹H-NMR (DMSO-d₆) δ 11.4–9.3 (m, 1H), 7.72 (d, J=3.3 Hz, 1H), 7.62(d, J=3.3 Hz, 1H), 7.35 (d, J=8.6 Hz, 2H), 7.17 (t, J=8.6 Hz, 1H), 5.87 (s, 1H), 4.01–3.74 (m, 3H), 3.42–2.50 (m, 22H), 1.84–1.75 (m, 4H) ppm.
MS (m/z): 718 (M+H)⁺

Example 43

Dimethyl 2-[2-[4-[2-[1-(aminocarbonyl)cyclopentyl]ethyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate A. Ethyl 2-[2-(4-benzyl-1-piperazinyl)ethyl]-6-iodohexanoate To a stirred solution of lithium diisopropylamide (2 M, 32.0 ml, 6.36 mmol) in tetrahydrofuran (420 ml) was added ethyl 4-(4-benzyl-1-piperazinyl)-butanoate (6.47 g, 21.2 mmol) (Preparation 1) at −78° C. and the mixture was stirred for 1 h at the same temperature. To this mixture was added HMPA (19.4 ml) and the resultant mixture was added to a solution of 1,4-diiodobutane (13.2 g, 4.25 mmol) in tetrahydrofuran (22 ml) at −78° C. After 1 h, the temperature was raised to −50° C. and the mixture was stirred for 1 hour. The reaction was quenched by adding AcOH (0.230 ml). After the mixture was basified with aq. saturated NaHCO$_3$, then the mixture was extracted with ethyl acetate. The extract was washed with brine, dried over Na$_2$SO$_4$, filtered and concentrated in vacuo. The residue was purified by column chromatography (SiO$_2$, 200–350 mesh/500 g/hexane:ethyl acetate=2:1) to provide a yellow oil (6.3 g/63%).
$^1$H-NMR (CDCl$_3$) δ 7.32–7.20 (m, 5H), 4.12 (q, J=7.1 Hz, 2H), 3.50 (s, 2H), 3.17 (t, J=6.9 Hz, 2H), 2.50–2.25 (m, 10H), 1.88–1.35 (m, 9H), 1.25 (t, J=7.1 Hz, 3H) ppm.

B. Ethyl 1-[2-(4-benzyl-1-piperazinyl)ethyl]cyclopentanecarboxylate

To a stirred solution of lithium diisopropylamide (2 M, 13.3 ml, 26.7 mmol) in tetrahydrofuran (113 ml) was added the solution of ethyl 2-[2-(4-benzyl-1-piperazinyl)ethyl]-6-iodohexanoate (6.3 g) in tetrahydrofuran (20 ml) at −78° C. After 30 min, the temperature was gradually raised to 0° C. during a period of 30 min. After 15 min at 0° C., the reaction was quenched by adding AcOH (0.230 ml). After the mixture was basified with aq. saturated NaHCO$_3$, then the resulting mixture was extracted with ethyl acetate. The extract was washed with brine, dried over NASO$_4$, filtered and concentrated in vacuo. The residue was purified by column chromatography (SiO$_2$, 200–350 mesh/500 g/hexane:ethyl acetate=2:1) to provide a yellow oil (4.2 g/92%).
$^1$H-NMR (CDCl3) δ 7.25–7.15 (m, 5H), 4.03 (q, J=7.1 Hz, 2H), 3.42 (s, 2H), 2.45–2.35 (m, 8H), 2.22–2.16 (m, 2H), 2.10–1.95 (m, 2H), 1.80–1.70 (m, 2H), 1.58–1.33 (m, 6H), 1.16(t, J=7.1 Hz, 3H) ppm.

C. 1-[2-(4-Benzyl-1-piperazinyl)ethyl]cyclopentanecarboxylic acid

The mixture of ethyl 1-[2-(4-benzyl-1-piperazinyl)ethyl]cyclopentanecarboxylate (300 mg, 0.871 mmol) and KOH (85%, 0.36 g, 3.49 mmol) in methanol (5.0 ml) and water (1.2 ml) was stirred at 95° C. overnight. To the mixture was added 2 N HCl until the pH became 5. After the solvent was removed in vacuo, the residue was extracted with dichloromethane (30 ml). The extract was washed with brine, dried over NASO$_4$, filtered and concentrated in vacuo to provide a yellow oil (276 mg/100%).
$^1$H-NMR (CDCl$_3$) δ 9.46 (brs, 1H), 7.35–7.25 (m, 5H), 3.66 (s, 2H), 3.00–2.65 (m, 10H), 2.20–2.10 (m, 2H), 1.95–1.90 (m, 2H), 1.75–1.60 (m, 2H), 1.55–1.40 (m, 2H) ppm.

D. 1-[2-(4-Benzyl-1-piperazinyl)ethyl]cyclopentanecarboxamide

A mixture of 1-[2-(4-benzyl-1-piperazinyl)ethyl]cyclopentanecarboxylic acid (300 mg, 0.948 mmol), NH$_4$HCO$_3$ and 2-ethoxy-N-ethoxycarbonyl-1,2-dihydroquinoline (469 mg, 3.49 mmol) in chloroform (5.0 ml) was stirred for 2 d. To the mixture was added sat NaHCO$_3$ (3 ml) and the mixture was extracted with dichloromethane After the solvent was removed in vacuo, the residue was extracted with dichloromethane (30 ml). The extract was washed with brine, dried over Na$_2$SO$_4$, filtered and concentrated in vacuo. The residue was purified by column chromatography (SiO$_2$, 200–350 mesh/21 g/dichloromethane:methanol=97:3) to provide a yellow oil (174 mg/58%).
$^1$H-NMR (CDCl$_3$) δ 7.35–7.20 (m, 5H), 6.68 (brs, 1H), 6.05 (brs, 1H), 3.49 (s, 2H), 2.60–2.30 (m, 10H), 2.15–2.00 (m, 2H), 1.80–1.40 (m, 8H) ppm.

E. 1-[2-(1-Piperazinyl)ethyl]cyclopentanecarboxamide

This compound was obtained according to a similar manner to that of example 1-C as a yellow solid.

$^1$H-NMR (CDCl$_3$) δ 6.68 (brs, 1H), 6.06 (brs,,1H), 2.90–2.75 (m, 4H), 2.50–2.28 (m, 6H), 2.12–2.00 (m, 2H), 1.80–1.45 (m, 8H) ppm.

F. Dimethyl 2-[2-[4-[2-[1-(aminocarbonyl)cyclopentyl]ethyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was obtained according to a similar manner to that of example 1-D as a yellow solid.
Free base
$^1$H-NMR (CDCl$_3$) δ 8.32 (br s, 1H), 7.72 (d, J=3.3 Hz, 1H), 7.24 (d, J=7.9 Hz, 2H), 7.21 (d, J=3.3 Hz), 7.00 (t, J=7.90 Hz, 1H), 5.99 (s ,1H), 4.09 (d, J=15.0 Hz, 1H), 3.79 (d, J=15.0 Hz, 1H), 3.66–3.58 (m, 4H), 3.55 (s, 3H), 3.53 (s, 3H), 3.40–3.24 (m, 3H), 3.05–2.95 (m, 1H), 2.48–2.32 (m, 6H), 2.14–2.02 (m, 2H), 1.82–1.46 (m, 8H) ppm.
HCl salt.
mp 158–163° C. (dec.)
IR (KBr)ν$_{max}$: 3373, 2949, 2550, 1686, 1655, 1508, 1433, 1294, 1188, 1103 cm$^{-1}$.
MS (m/z): 718 (M+H)$^+$ Example 44

Dimethyl 2-[2-[4-[1-[(acetylamino)methyl]cyclohexyl]-1-piperidinyl]-2-oxoethyl]-4-(2,6dichlorophenyl)-6-[2-(1,3-thiazol-2-yl)ethyl]-1,4dihydro-3,5-pyridinedicarboxylate A. 1-(1-Benzyl-4-piperidinyl)cyclohexanecarbonitrile This compound was prepared by a procedure similar to that described in example 1-B as a white solid.
$^1$H NMR (CDCl3) δ 7.35–7.20 (m, 5H), 3.49 (s, 2H), 3.04–2.90 (m, 2H), 2.05–1.00 (m, 17H) ppm.

B. [1-(1-Benzyl-4-piperidinyl)cyclohexyl]methylamine

This compound was prepared by a procedure similar to that described in example 2-A as a colorless oil.
$^1$H NMR (CDCl$_3$) δ 7.38–7.20 (m, 5H), 3.49 (s, 2H), 3.03–2.90 (m, 2H), 2.66 (s, 2H), 2.00–1.20 (m, 19H) ppm.

C. N-[[1-(1-Benzyl-4-piperidinyl)cyclohexyl]methyl]acetamide

This compound was prepared by a procedure similar to that described in example 4 as a white solid
$^1$H NMR (CDCl$_3$) δ 7.35–7.20 (m, 5H), 5.43 (br s, 1H ), 3.49 (s, 2H), 3.32–3.21 (m, 2H), 3.03–2.90 (m, 2H), 2.05–1.78 (m, 8H), 1.68–1.15(m, 12H) ppm.

D. N-[[1-(4-piperidinyl)cyclohexyl]methyl]acetamide

This compound was prepared by a procedure similar to that described in example 1-C as a white amorphous.
MS (m/z): 239 (M)$^+$
$^1$H NMR (CDCl$_3$) δ 5.79 and 5.47 (br s, total 1H ), 3.75–2.55 (m, 6H), 2.02 and 2.00 (s, total 3H), 1.97–1.15 (m, 16H) ppm E. Dimethyl 2-[2-[4-[1-[(acetylamino)methyl]cyclohexyl]-1-piperidinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a pale yellow amorphous.
$^1$H NMR (CDCl$_3$) δ 8.42 and 8.32 (br s, total 1H), 7.75–7.67 (m, 1H), 7.30–7.15 (m, 3H), 6.99 ( t, J=8.0 Hz, 1H), 6.00 (s, 1H), 5.40–5.25 (m, 1H), 4.75–4.62 (m, 1H), 4.30–4.00 (m, 2H), 3.79 ( d, J=15.0 Hz, 1H), 3.55 (s, 3H), 3.54 (s, 3H), 3.40–3.20 (m, 5H), 3.10–2.80 (m, 2H), 2.55–2.40 (m, 1H), 1.99 (s, 3H), 1.85–1.10 (m, 15H) ppm.
mp: 114–116° C. (dec.)
MS (m/z): 731 (M+H)$^+$.
IR (KBr)ν$_{max}$: 3300, 3101, 2932, 2860, 1697, 1636, 1508, 1433, 1290, 1225, 1186, 1103, 1053, 1016, 955, 766, 723cm$^1$.

Example 45

Dimethyl 4-(2,6-dichlorophenyl)-2-[2-[4-[1-[(ethylamino)methyl]cyclohexyl]-1-piperidinyl]-2-oxoethyl]-6-[2-(1,3-thiazol-2-yl)ethyl]-1,4-dihydro-3,5-pyridinedicarboxylate A. tert-Butyl [1-(1-benzyl-4-piperidinyl)cyclohexyl]methylcarbamate This compound was prepared by a procedure similar to that described in example 2-B as a yellow oil.
$^1$H NMR (CDCl$_3$) δ 7.35–7.20 (m, 5H), 4.42 (br s, 1H), 3.49 (s, 2H), 3.20–3.10 (m, 2H), 3.03–2.90 (m, 2H), 1.98–1.15 (m, 26H) ppm.

B. tert-Butyl [1-(1-benzyl-4-piperidinyl)cyclohexyl]methyl (ethyl)carbamate

This compound was prepared by a procedure similar to that described in example 3-A as a pale yellow solid.
$^1$H NMR (CDCl$_3$) δ 7.35–7.20 (m, 5H), 3.50 (s, 2H), 3.30–2.90 (m, 6H), 1.98–1.12 (m, 26H), 1.06 (t, J=6.9 Hz, 3H) ppm C. tert-Butyl ethyl[1-(4-piperidinyl)cyclohexyl]methyl carbamate This compound was prepared by a procedure similar to that described in example 1-C as a pale yellow oil.
$^1$H NMR (CDCl$_3$) δ 3.30–3.00 (m, 6H), 2.64–2.48 (m, 2H), 1.98–1.12 (m, 25H), 1.07 (t, J=6.9 Hz, 3H) ppm.

D. Dimethyl 2-[2-[4-[1-[[(tert-butoxycarbonyl)(ethyl)amino]methyl]cyclohexyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a pale yellow amorphous.
$^1$H NMR (CDCl$_3$) δ 8.49 and 8.34 (br s, total 1H), 7.77–7.68 (m, 1H), 7.30–7.15 (m, 3H), 7.05–6.91 ( m, 1H), 6.00 (s, 1H), 4.78–4.62 (m, 1H), 4.35–4.10 (m, 2H), 3.85–3.68 (m, 1H), 3.55 (s, 3H), 3.54 (s, 3H), 3.42–2.80 (m, 9H), 2.58–2.40 (m, 1H), 2.00–1.00 (m, 27H) ppm.

E) Dimethyl 4-(2,6-dichlorophenyl)-2-[2-[4-[1-[(ethylamino)methyl]cyclohexyl]-1-piperidinyl]-2-oxoethyl]-6-[2-(1,3-thiazol-2-yl)ethyl]-1,4- dihydro-3,5-pyridinedicarboxylate This compound was prepared by a procedure similar to that described in example 2-E as a yellow amorphous.
free base
$^1$H NMR (CDCl$_3$) δ 8.51 and 8.36 (br s, total 1H), 7.75–7.68 (m, 1H), 7.30–7.17 (m, 3H), 7.05–6.95 ( m, 1H), 6.00 (s, 1H), 4.74–4.61 (m, 1H), 4.28–3.73 (m, 3H), 3.55 (s, 3H), 3.54 (s, 3H), 3.42–3.22 (m, 3H), 3.10–2.83 (m, 2H), 2.70–2.40 (m, 5H), 1.75–1.18 (m, 16H), 1.17–1.05 (m, 3H) ppm.
HCl salt
mp: 162–163° C. (dec.)
MS (m/z): 717 (M+H)$^+$.
IR(KBr)ν$_{max}$: 3377, 2945, 1697, 1624, 1512, 1433, 1292, 1229, 1188, 1103, 1053, 1015, 768 cm$^{-1}$

Example 46

Dimethyl 2-[2-[4-[[1-(aminomethyl)cyclobutyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate A. 1-[(4-Benzyl-1-piperazinyl)methyl]cyclobutanecarbonitrile This compound was prepared by a procedure similar to that described in example 1-B as a yellow amorphous solid.
$^1$H NMR (CDCl$_3$) δ 7.27(m, 5H), 3.50 (s, 2H), 2.64 (s, 2H), 2.58 (br, 4H), 2.48 (br, 4H), 2.27 (m, 4 H), 2.00 (m, 2H) ppm.

B. [1-[(4-Benzyl-1-piperazinyl)methyl]cyclobutyl]methylamine

This compound was prepared by a procedure similar to that described in example 2-A as a yellow amorphous solid.
$^1$H NMR (CDCl$_3$) δ 7.30 (m, 5H), 3.48 (s, 2H), 2.82 (s, 2H), 2.38 (m, 8H), 1.91–1.70 (m, 8H) ppm C. tert-Butyl [1-[(4-benzyl-1-piperazinyl)methyl]cyclobutyl]methylcarbamate This compound was prepared by a procedure similar to that described in example 2-B as a yellow amorphous solid.
$^1$H NMR (CDCl$_3$) δ 7.30 (m, 5H), 3.48 (s, 2H), 3.33 (br, 2H), 2.42–2.37 (m, 8H), 2.00–1.71 (m, 6H), 1.64 (s, 2H), 1.44 (s, 9H) ppm.

D. tert-Butyl[1-(1-piperazinylmethyl)cyclobutyl]methylcarbamate

This compound was prepared by a procedure similar to that described in example 1-C as a yellow amorphous solid.
$^1$H NMR (CDCl$_3$) δ 3.35 (m, 2H), 2.86 (m, 3H), 2.36 (br, 4H), 2.00–1.72 (br, 9H), 1.44 (s, 9H) ppm.

E. Dimethyl 2-[2-[4-[[1-(aminomethyl)cyclobutyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate This compound was prepared by a procedure similar to that described in example 1-D as a yellow amorphous solid.
$^1$H NMR (CDCl$_3$) δ 8.37 (s, 1H), 7.71 (d, J=3.45 Hz, 1H), 7.28–7.20 (m, 3H), 7.00 (t, J=7.42 Hz, 1H), 5.99 (s, 1H), 4.10–4.04 (d, J=15.0 Hz, 1H), 3.84–3.78 (d, J=15.0 Hz, 1H), 3.55 (s, 3H), 3.53 (s, 3H), 3.37–3.25 (m, 3H), 3.03–2.96 (m, 1H), 2.84 (s, 2H), 2.46–2.35 (br, 8H), 1.97–1.77 (br, 8H) ppm

Example 47

Dimethyl 4-(2,6-dichlorophenyl)-2-[2-[4-[[1-[(ethylamino)methyl]cyclobutyl]methyl]-1-piperazinyl]-2-oxoethyl]-6-[2-(1,3-thiazol-2-yl)ethyl]-1,4-dihydro-3,5-pyridinedicarboxylate A. tert-butyl [1-[(4-benzyl-1-piperazinyl)methyl]cyclobutyl]methyl(ethyl)carbamate This compound was prepared by a procedure similar to that described in example 3-A as a yellow amorphous solid.
$^1$H NMR (CDCl$_3$) δ 7.30 (m, 5H), 3.48 (s, 2H), 3.40 (br, 4H), 2.38–2.31 (br, 10H), 1.90–1.62 (m, 6H) 1.08 (t, J=6.9 Hz, 3H) ppm.

B. tert-butyl ethyl[[1-(1-piperazinylmethyl)cyclobutyl]methyl]carbamate

This compound was prepared by a procedure similar to that described in example 1-C as a yellow amorphous solid.
$^1$H NMR (CDCl$_3$) δ 3.42–3.36 (br, 4H), 2.81 (br, 4H), 2.28 (br, 6H), 1.91–1.57 (m, 6H), 1.47 (s, 9H) 1.08 (t, J=6.91 Hz, 3H) ppm C. Dimethyl 4-(2,6-dichlorophenyl)-2-[2-[4-[[1-[(ethylamino)methyl]cyclobutyl]methyl]-1-piperazinyl]-2-oxoethyl]-6-[2-(1,3-thiazol-2-yl)ethyl]-1,4-dihydro-3,5-pyridinecarboxylate This compound was prepared by a procedure similar to that described in example 1-D as a pale yellow amorphous.
$^1$H NMR (CDCl$_3$) δ 8.37 (s, 1H), 7.72 (m, 1H), 7.28–7.19 (m, 3H), 7.00 (t, J=8.4 Hz, 1H), 5.99 (s, 1H), 4.08–4.02 (d, J=15.0 Hz, 1H), 3.85–3.79 (d, J=15.0 Hz, 1H), 3.55 (s, 3H), 3.53 (s, 3H), 3.42–3.25 (m, 3H), 3.03–2.95 (m, 1H), 2.75–2.62 (m, 6H), 2.40–2.37 (m, 8H), 1.95–1.80 (m, 6H), 1.11 (t, J=7.0 Hz, 3H) ppm.

Example 48

Dimethyl 4-(2,6-dichlorophenyl)-2-[2-oxo-2-[4-[8-(2-oxo-1-pyrrolidinyl)bicyclo[3.2.1]oct-3-yl]-1-piperazinyl]carbonyl]-6-[2-(1,3-thiazol-2-yl)ethyl]-1,4-dihydro-3,5-pyridinedicarboxylate A. 3-(4-Benzyl-1-piperazinyl)bicyclo[3.2.1]octan-8-one oxime To a solution of 3-(4-Benzyl-1-piperazinyl)bicyclo[3.2.1] octan-8-one (525 mg/1.76 mmol) in ethanol (5 ml) was added hydroxyamine hydrochloride (122 mg/1.76 mmol) and the mixture was stirred for 15 hours. The reaction mixture was quenched with sat.NaHCO$_3$ and the whole was extracted dichloromethane (30 ml×2). The combined extracts were washed with brine, dried over magnesium sulfate, and concentrated in vacuo to give the titled compound as white solid. (550 mg/100%)
$^1$H NMR (CDCl$_3$) δ 7.38–7.24 (m, 5H), 3.49 (s, 2H), 2.75–2.42 (m, 11H), 2.11–1.60 (m, 8H) ppm.

B. 3-(4-Benzyl-1-piperazinyl)bicyclo[3.2.1]octan-8-amine

This compound was prepared by a procedure similar to that described in example 2-A as a yellow amorphous solid.
$^1$H NMR (CDCl$_3$) δ 7.30–7.15 (m, 5H), 3.50 (s, 2H), 2.94 (t, J=4.4 Hz, 1H), 2.70–2.30 (m, 9H), 2.06–1.40 (m, 10H) ppm.

C. N-[3-(4-Benzyl-1-piperazinyl)bicyclo[3.2.1]oct-8-yl]-4-chlorobutanamide

This compound was prepared by a procedure similar to that described in example 20-B as a pale yellow amorphous.
$^1$H-NMR (CDCl$_3$) δ 7.32–7.25 (m, 5H), 6.03 (br s, 1H), 3.62 (t, J=6.3 Hz, 2H), 3.52 (s, 2H), 2.62–1.35 (m, 24H) ppm.

D. 1-[3-(4-Benzyl-1-piperazinyl)bicyclo[3.2.1]oct-8-yl]-2-pyrrolidinone

This compound was prepared by a procedure similar to that described in example 20-C as a pale yellow amorphous.
$^1$H-NMR (CDCl$_3$) δ 7.35–7.18 (m, 5H), 3.50 (s, 2H), 3.44–3.35 (m, 2H), 3.09–3.02 (m, 2H), 2.84–2.76 (m, 2H), 2.60–2.30 (m, 11H), 2.07–1.95 (m, 2H), 1.76–1.44 (m, 8H) ppm.

E. 1-[3-(1-Piperazinyl)bicyclo[3.2.1]oct-8-yl]-2-pyrrolidinone

This compound was prepared by a procedure similar to that described in example 1-C as a pale yellow amorphous.
$^1$H-NMR (CDCl$_3$) δ 3.46–3.33 (m, 2H), 3.10–2.99 (m, 3H), 2.85–2.73 (m, 2H), 2.70–2.30 (m, 9H), 2.12–1.95 (m, 2H), 1.80–1.40 (m, 8H) ppm.

F. Dimethyl 4-(2,6dichlorophenyl)-2-[2-oxo-2-14-[8-(2-oxo-1-pyrrolidinyl)bicyclo[3.2.1]oct-3-yl]-1-piperazinyl]carbonyl]-6-[2-(1,3-thiazol-2-yl)ethyl]-1,4-dihydro-3,5-pyridinedicarboxylate This compound was prepared by a procedure similar to that described in example 1-D as a pale yellow amorphous. Free base
$^1$H NMR (CDCl$_3$) δ: 8.38 (br s, 1H), 7.71 (d, J=3.3 Hz, 1H), 7.24 (d, J=7.9 Hz, 2H), 7.20 (d, J=3.3 Hz, 1H), 7.00 (t, J=7.9 Hz, 1H), 5.99 (s, 1H), 4.09 (d, J=15.0 Hz, 1H), 3.79 (d, J=15.0 Hz, 1H), 3.61 (br s, 4H), 3.55 (s, 3H), 3.53 (s, 3H), 3.43–3.22 (m, 5H), 3.10–2.94 (m, 3H), 2.85–2.74 (m, 2H), 2.55–2.34 (m, 6H), 2.09–1.97 (m, 2H), 1.60–1.44 (m, 6H) ppm.
HCl salt
mp: 195–200° C. (dec.)
IR (KBr)ν$_{max}$: 1680, 1508, 1433, 1294, 1188, 1103, 768 cm$^{-1}$.
MS (m/z): 770 (M+H)$^+$ Preparation 1

Ethyl 4-(4-benzyl-1-piperazinyl) butanoate

This compound was obtained according to a similar manner to that of example 1-A as a yellow solid.
$^1$H NMR (CDCl$_3$) δ 7.34–7.22 (m, 5H), 4.12 (q, J=7.1 Hz, 2H), 3.51 (s, 2H), 2.54–2.28 (m, 10H), 1.87–1.72 (m, 4H), 1.25 (t, J=7.1 Hz, 3H) ppm.

The chemical structures of the compounds prepared in the Examples 1 to 48 are summarized in the following tables.

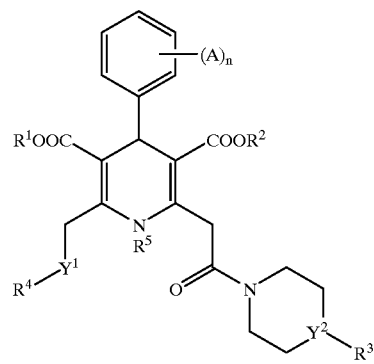

(wherein (A)$_n$ is 2,6-dichloro; R$^1$ and R$^2$ are methyl; R$^4$ is 1,3-thiazoly-2-yl; R$^5$ is hydrogen; Y is —CH$_2$—; and n is 2.)

TABLE

| Ex. # | R$^3$ |
|---|---|
| 1 | 1-cyanocyclohexylmethyl |
| 2 | aminomethylcyclohexylmethyl |
| 3 | 1-(ethylaminomethyl)cyclohexylmethyl |
| 4 | 1-(acetylaminomethyl)cyclohexylmethyl |
| 5 | 4-[[1-[(methylsulfonyl)amino]methyl]cyclohexyl]methyl |
| 6 | 1-aminocyclohexylmethyl |
| 7 | ethylaminomethylcyclopentylmethyl |
| 8 | 1-(dimethylaminomethyl)cyclopentylmethyl |
| 9 | 1-(diethylaminomethyl)cyclopentylmethyl |
| 10 | 1-(1-pyrrolidinylmethyl)cyclopentylmethyl |
| 11 | 1-(cyclopentylaminomethyl)cyclopentylmethyl |
| 12 | 8-(diethylamino)bicyclo[3.2.1]oct-3-yl |
| 13 | [2,2-dimethyl-3-(methylsulfonylamino)]propyl |
| 14 | 1-cyanocyclopentylmethyl |
| 15 | 2-cyano2-methylpropyl |
| 16 | 3-acetylamino-2,2-dimethylpropyl |
| 17 | 1-(aminomethyl)cyclopentylmethyl |
| 18 | 3-amino-2,2-dimethylpropyl |
| 19 | 3-ethylamino-2,2-dimethylpropyl |
| 20 | 3-(2-oxopyrrolidin-1-yl)-3,3-dimethylpropyl |
| 21 | 3-(2-oxopyrrolidin-1-yl)-2,2-dimethylpropyl |
| 22 | 3-(2-oxopyrrolidin-1-yl)propyl |
| 23 | 4-(2-oxopyrrolidin-1-yl)cyclohexyl |
| 24 | 3-(1,1-dioxoisothiazolin-2-yl)propyl |
| 25 | 3-(2-oxo-1,3-oxazolidin-3-yl)propyl |
| 26 | 1-(2-oxopyrrolidin-1-ylmethyl)cyclohexylmethyl |
| 27 | 1-(2-oxopyrrolidin-1-ylmethyl)cyclohexylmethyl |
| 28 | 2-(1-hydroxycyclohexyl)ethyl |
| 29 | 3-(2-methyl-5-oxo-pyrrolidin-1-yl)propyl |
| 30 | 3-(3-methyl-5-oxo-pyrrolidin-1-yl)propyl |
| 31 | 1-(acetyl(ethyl)amino)cyclopentylethyl |
| 32 | 1-(acetyl(ethyl)aminomethyl)cyclopentylmethyl |
| 33 | 1-(2-oxo-pyrrolidin-1-yl)cyclopentylethyl |
| 34 | 1-(diethylamino)cyclopentylethyl |
| 35 | 4-(2-oxo-1-pyrrolidynyl)butyl |
| 36 | 4-methyl-4-(2-oxo-1-pyrrolidinyl)pentyl |
| 37 | 1-(2-oxo-1-pyrrolidinylmethyl)cyclopentylethyl |
| 38 | 4-morpholinobutyl |
| 39 | 3-methyl-3-(2-oxo-pyrrolidin-1-yl)pentyl |
| 40 | diethylaminomethylcyclopentylethyl |
| 41 | 2-oxo-piperidin-1-ylbutyl |
| 42 | 4-(1-piperidinyl)butyl |
| 43 | 1-(carbomoyl)cyclopentylethyl |
| 44 | 1-(acetylaminomethyl)cyclohexyl |
| 45 | 1-(ethylaminomethyl)cyclohexyl |
| 46 | [1-(aminomethyl)cyclobutyl]methyl |
| 47 | 4-[[1-[(ethylamino)methyl]cyclobutyl]methyl |
| 48 | 2-oxo-2-[4-[8-(2-oxo-1-pyrrolidinyl)bicyclo[3.2.1]oct-3-yl |

What is claimed is:

1. A compound of the formula (I):

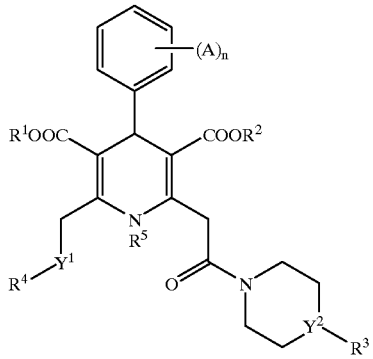

(I)

or the pharmaceutically acceptable salts thereof wherein

A is independently halo;
$Y^1$ is —(CH$_2$)$_m$—, C(O) or S(O);
$Y^2$ is N or CH;
$R^1$ and $R^2$ are independently $C_{1-4}$ alkyl;
$R^3$ is selected from the following:
(a) —(CH$_2$)$_p$—C$_{3-7}$ cycloalkyl, the cycloalkyl moiety being optionally substituted with one, two or three substituents selected from cyano, amino-C$_{1-4}$ alkyl-, C$_{1-4}$ alkylamino-C$_{1-4}$ alkyl-, C$_{1-3}$ alkylcarbonylamino-C$_{1-4}$ alkyl-, C$_{1-4}$ alkylsulfonylamino-C$_{1-4}$ alkyl, amino, 2-oxopyrrolidinyl, C$_{4-7}$ cycloalkylamino-C$_{1-4}$ alkyl, di-C$_{1-4}$ alkylamino-C$_{1-4}$ alkyl-, hydroxyl, carbamoyl, C$_{1-3}$ alkylcarbonyl(C$_{1-4}$ alkyl)amino, C$_{1-4}$ alkylcarbonyl(C$_{1-4}$ alkyl)amino-C$_{1-4}$ alkyl, di-C$_{1-4}$ alkylamino, pyrrolidinyl-C$_{1-4}$ alkyl, 2-oxopyrrolidinyl-C$_{1-4}$ alkyl and di-C$_{1-4}$ alkylamino-C$_{1-4}$ alkyl;
(b) —C$_{5-7}$ alkyl optionally substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, amino, C$_{1-4}$ alkylamino, morpholinylcarbonyl, morpholino, C$_{1-3}$alkyl-2-oxopyrrolidinyl, piperidinyl and 2-oxo-piperidinyl;
(c) —C$_{1-4}$ alkyl substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, morpholino, C$_{1-3}$alkyl-2-oxopyrrolidinyl, piperidinyl and 2-oxo-piperidinyl; and
(d) C$_{7-9}$ bicycloalkyl optionally substitued with di-C$_{1-4}$ alkylamino and oxopyrrolidinyl;

$R^4$ is thiazolyl, imidazolyl or oxazolyl, the thiazolyl, imidazolyl or oxazolyl being optionally substituted with one or two substituents independently selected from C$_{1-4}$ alkyl and halo;
X is S, —NH, —N—C$_{1-4}$ alkyl or 0;
$R^5$ is hydrogen or C$_{1-4}$ alkyl;
$R^6$ is C$_{1-4}$ alkyl or halo;
m is 0, 1 or 2;
n is 0, 1, 2, 3, 4 or 5; and
p is 0, 1, 2, 3, 4, 5 or 6.

2. A compound according to claim 1, wherein
(A)$_n$ is 2,6-dichloro;
$Y^1$ is —CH$_2$—;
$Y^2$ is N or CH;
$R^1$ and $R^2$ are independently methyl, ethyl or propyl;
$R^3$ is selected from the following:
(a) —(CH$_2$)$_p$—C$_{3-7}$ cycloalkyl, the cycloalkyl moiety being optionally substituted with one, two or three substituents selected from cyano, amino-C$_{1-4}$ alkyl-, C$_{1-4}$ alkylamino-C$_{1-4}$ alkyl-, C$_{1-3}$ alkylcarbonylamino-C$_{1-4}$ alkyl-, C$_{1-4}$ alkylsulfonylamino-C$_{1-4}$ alkyl, amino, 2-oxopyrrolidinyl, C$_{4-7}$ cycloalkylamino-C$_{1-4}$ alkyl, di-C$_{1-4}$ alkylamino-C$_{1-4}$ alkyl-, hydroxyl, carbamoyl, C$_{1-3}$ alkylcarbonyl(C$_{1-4}$ alkyl)amino, C$_{1-4}$ alkylcarbonyl(C$_{1-4}$ alkyl)amino-C$_{1-4}$ alkyl, di-C$_{1-4}$ alkylamino, pyrrolidinyl-C$_{1-4}$ alkyl, 2-oxopyrrolidinyl-C$_{1-4}$ alkyl and di-C,4 alkylamino-C$_{1-4}$ alkyl;
(b) —C$_{5-7}$ alkyl optionally substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, amino, C$_{1-4}$ alkylamino, morpholinylcarbonyl, molipholino, C$_{1-3}$alkyl-2-oxopyrrolidinyl, piperidinyl and 2-oxo-piperidinyl; and
(c) —C$_{1-4}$ alkyl substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, morpholino, C$_{1-3}$alkyl-2-oxopyrrolidinyl, piperidinyl and 2-oxo-piperidinyl; and
(d) C$_{7-9}$ bicycloalkyl optionally substitued with di-C$_{1-4}$ alkylamino or oxopyrrolidinyl;

$R^4$ is 1,3-thiazol-2-yl, 1H-imidazol-2-yl, 1-methyl-1H-imidazol-2-yl, 1-ethyl-1H-imidazol-2-yl or 1,3-oxazol-2-yl;
X is S, —NH or —N-methyl;
$R^5$ is hydrogen;
n is 2; and
p is 0, 1, 2, 3, 4, 5 or 6.

3. A compound according to claim 2, wherein
$R^1$ and $R^2$ are methyl;
$R^3$ is selected from the following:
(a) —(CH$_2$)$_p$—C$_{4-6}$ cycloalkyl, the cycloalkyl moiety being optionally substituted with one or two substituents selected from cyano, amino-C$_{1-4}$ alkyl-, C$_{1-4}$ alkylamino-C$_{1-4}$ alkyl-, C$_{1-3}$ alkylcarbonylamino-C$_{1-4}$ alkyl-, C$_{1-4}$ alkylsulfonylamino-C$_{1-4}$ alkyl, amino, 2-oxopyrrolidinyl, C$_{4-7}$ cycloalkylamino-C$_{1-4}$ alkyl, di-C$_{1-4}$ alkylamino-C$_{1-4}$ alkyl-, hydroxyl, carbamoyl, C$_{1-3}$ alkylcarbonyl(C$_{1-4}$ alkyl)amino, C$_{1-4}$ alkylcarbonyl(C$_{1-4}$ alkyl)amino-C$_{1-4}$ alkyl, di-C$_{1-4}$ alkylamino, pyrrolidinyl-C$_{1-4}$ alkyl, 2-oxopyrrolidinyl-C$_{1-4}$ alkyl and di-C$_{1-4}$ alkylamino-C$_{1-4}$ alkyl;
(b) —C$_{2-4}$ alkyl optionally substituted with one or two substituents selected from 2-oxopyrrolidinyl, C$_{1-3}$ alkylsuflonylamino, cyano, C$_{1-3}$ alkylcarbonylamino, 1,1-dioxoisothiazolinyl, 2-oxo-1,3-oxazolidinyl, amino, C$_{1-4}$ alkylamino, morpholinylcarbonyl, morpholino, C$_{1-3}$alkyl-2-oxopyrrolidinyl, piperidinyl and 2-oxo-piperidinyl;
(b) —C$_{2-4}$ alkyl substituted with one or two substituents selected from 2-oxopyrrolidinyl, C$_{1-3}$ alkylsulfonylamino, cyano, $C_{1-3}$ alkylcarbonylamino, 1,1-dioxoisothiazolinyl, 2-oxo-1,3-oxazolidinyl, morpholino, $C_{1-3}$alkyl-2-oxopyrrolidinyl, piperidinyl and 2-oxo-piperidinyl; and (d) bicyclo[3.2.1]octyl optionally substitued with $C_{1-3}$ alkyl-amino or oxopyrrolidinyl;

$R^4$ is 1,3-thiazol-2-yl, 1-methyl-1H-imidazol-2-yl or 1,3-oxazol-2-yl; and p is 0, 1, 2 or 3.

4. A compound according to claim 3, wherein $R^3$ is selected from the following:

(a) $(CH_2)_p$—$C_{4-6}$ cycloalkyl, the cycloalkyl moiety being optionally substituted with a substituent selected from cyano, aminomethyl, aminoethyl, ethylaminomethyl, methylaminoethyl, acetylaminomethyl, acetylaminoethyl, ethylcarbonylaminomethyl, methylsulfonylaminomethyl, methylsulfonylaminoethyl, amino, dimethylaminomethyl, dimethylaminoethyl, diethylaminomethyl, diethylaminoethyl, pyrrolidinylmethyl, pyrrolidinylethyl, cyclopentylaminomethyl, cyclopentylaminoethyl, oxopyrrolidinyl, hydroxy, (ethyl)(acetyl)amino, (methyl)(acetyl)amino, (ethyl)(acetyl)aminomethyl, (methyl)(acetyl)aminomethyl, diethylamino, dimethylamino, aminocarbonyl, acetylaminomethyl, 2-oxopyrrolidinylmethyl and diethylaminomethyl;

(b) —$C_{5-6}$ alkyl optionally substituted with a substituent selected from methylsulfonylamino, ethylsulfonylamino, cyano, acetylamino, ethylcarbonylamino, amino, etylamino, methylamino, oxopyrrolidinyl, 1,1-dioxoisothiazolidinyl, 2-oxo-1,3-oxazolidinyl, methyloxopyrrolidinyl, morpholinocarbonyl, morpholino, oxopiperidinyl and piperidinyl;

(c) —$C_{2-4}$ alkyl substituted with a substituent selected from methylsulfonylamino, ethylsulfonylamino, cyano, acetylamino, ethylcarbonylamino, oxopyrrolidinyl, 1,1-dioxoisothiazolidinyl, 2-oxo-1,3-oxazolidinyl, methyloxopyrrolidinyl, morpholinocarbonyl, morpholino, oxopiperidinyl and piperidinyl; and (d) bicyclo[3.2.1]octyl optionally substitued with methylamino, ethylamino or oxopyrrolidinyl.

5. A compound according to claim 1 selected from dimethyl 2-[2-[4-[(1-cyanocyclohexyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-[[1-(aminomethyl)cyclohexyl]methyl]-1-piperazinyl]-2-oxoethyl]4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(ethylamino)methyl]cyclohexyl]methyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[[1-[(acetylamino)methyl]cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[[(methylsulfonyl)amino]methyl]cyclohexyl]methyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[((1-aminocyclohexyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(ethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(dimethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(diethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-(1-pyrrolidinylmethyl)cyclopentyl]methyl]-1-piperazinyl]ethyl]-6-[2-(1,3-thiazol-2-yl)ethyl]-1,4-dihydro-3,5-pyridinedicarboxylate;

dimethyl 2-[2-[4-[[1-[(cyclopentylamino)methyl]cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-(8-(diethylamino)bicyclo [3.2.1]oct-3-yl)-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2,2-dimethyl-3-[(methylsulfonyl)amino]propyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[(1-cyanocyclopentyl)methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-(2-cyano-2-methylpropyl)-1-piperazinyl]-2-oxoethyl]-4-(2,6-dichlorophenyl)-6-[2-(1,3 -thiazol-2-yl)ethyl]-1,4-dihydro-3,5-pyridinedicarboxylate;

dimethyl 2-[2-[4-[3-(acetylamino)-2,2-dimethylpropyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-[[1-(aminomethyl)cyclopentyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-(3-amino-2,2-dimethylpropyl)-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[3-(ethylamino)-2,2-dimethylpropyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-methyl-3-(2-oxo-1-pyrrolidinyl)butyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2,2-dimethyl-3-(2-oxo-1-pyrrolidinyl)-propyl]-piperazinyl]-2-oxoethyl]-6-[2-(1,3-thiazol-2-yl)ethyl]-1 ,4-dihydro-3,5-pyridinedicarboxylate;

dimethyl 4-(2,6-dichlorophenyl)-2-[2-oxo-2-[4-[3-(2-oxo-1-pyrrolidinyl)propyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[4-(2-oxo-1-pyrrolidinyl)cyclohexyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-(1,1-dioxoisothiazolinyl)propyl]-1-piperadinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[3-(2-oxo-1,3-oxazolidin-3-yl)propyl]-1-piperadinyl]ethyl]-6-[2-(1,3-thiazol-2-yl)ethyl]- 1,4-dihydro-3,5-pyridinedicarboxylate;

dimethyl 4-(2,6-dichlorophenyl)-2-[2-oxo-2-[4-[[1-[(2-oxo-1-pyrrolidinyl)methyl]cyclohexyl]methyl-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-[(2-oxo-1-pyrrolidinyl)methyl]cyclopentyl]methyl-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2-(1-hydroxycyclohexyl)ethyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-(2-methyl-5-oxo-1-pyrrolidinyl)propyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-(3-methyl-2-oxo-1-pyrrolidinyl)propyl]-1-piperazinyl]-2-oxoethyl]-6-[2-(1,3-thiazol-2-yl)ethyl]-1,4-dihydro-3,5-pyridinedicarboxylate;

dimethyl 2-[2-[4-[3-[acetyl(ethyl)amino]propyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[-4-[[1-[(acetyl(ethyl)amino)methyl]cyclopentyl]methyl]-1-piperazinyl]-2-oxoethyl]-4-(2,6-dichlorophenyl)-1,4-dihydro-3,5-pyridinedicarboxylate;

dimethyl 4-(2,6-dichlorophenyl)-2-[2-oxo-2-[4-[2-[1-(2-oxo-1-pyrrolidinyl)cyclopentyl]ethyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2-[1-(diethylamino)cyclopentyl]ethyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-[4-[4-(2-oxo-1-pyrrolidinyl)butyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[4-methyl-4-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[2-[1-[2-oxo-1-pyrrolidinyl)methyl]cyclopentyl]ethyl]-1-piperazinyl]ethyl]-6-[2-(1,3-thiazol-2-yl)ethyl]-1,4-dihydro-3,5-pyridinedicarboxylate;

dimethyl 4-(2,6-Dichlorophenyl)-2-[2-[4-[4-(4-morpholinyl)-4-oxobutyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[4-(4-morpholinyl)butyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-ethyl-3-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[2-[1-[(diethylamino)methyl]cyclopentyl]ethyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[4-(2-oxo-1-piperidinyl)butyl]-1-piperazinyl]ethyl]-6-[2-(1,3-thiazol-2-yl)ethyl-1,4-dihydro-3,5-pyridinedicarboxylate;

dimethyl 4-(2,6-dichlorophenyl)-2-[2-oxo-2-[4-[4-(1-piperidinyl)butyl]-1-piperazinyl]ethyl]-6-[2-(1,3-thiazol-2-yl)ethyl]-1,4-dihydro-3,5-pyridinedicarboxylate;

dimethyl 2-[2-[4-[2-[1-(aminocarbonyl)cyclopentyl]ethyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 2-[2-[4-[1-[(acetylamino)methyl]cyclohexyl]-1-piperidinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[1-[(ethylamino)methyl]cyclohexyl]-1-piperidinyl]-2-oxoethyl]-6-[2-(1,3-thiazol-2-yl)ethyl]-1,4-dihydro-3,5-pyridinedicarboxylate;

dimethyl 2-[2-[4-[[1-(aminomethyl)cyclobutyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(ethylamino)methyl]cyclobutyl]methyl]-1-piperazinyl]-2-oxoethyl]-6-[2-(1,3-thiazol-2-yl)ethyl]-1,4-dihydro-3,5-pyridinedicarboxylate; and dimethyl 4-(2,6-dichlorophenyl)-2-[2-oxo-2-[4-[8-(2-oxo-1-pyrrolidinyl)bicyclo[3.2.1]oct-3-yl]-1-piperazinyl]carbonyl]-6-[2-(1,3-thiazol-2-yl)ethyl}-1,4-dihydro-3,5-pyridinedicarboxylate.

6. A compound according to claim 5 selected from dimethyl 2-[2-[4-[[1-(aminomethyl)cyclohexyl]methyl]-1-piperazinyl]-2-oxoethyl]-4-(2,6-dichlorophenyl)-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(dimethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[[1-[(diethylamino)methyl]cyclopentyl]methyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-(1-pyrrolidinylmethyl)cyclopentyl]methyl]-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[3-methyl-3-(2-oxo-1-pyrrolidinyl)butyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-oxo-2-[4-[[1-[(2-oxo-1-pyrrolidinyl)methyl]cyclopentyl]methyl-1-piperazinyl]ethyl]-6-[2-(1,3-thiazol-2-yl)ethyl]-1,4-dihydro-3,5-pyridinedicarboxylate;

dimethyl 4-(2,6-dichlorophenyl)-2-[2-[4-[4-methyl-4-(2-oxo-1-pyrrolidinyl)pentyl]-1-piperazinyl]-2-oxoethyl]-6-[2-(1,3-thiazol-2-yl)ethyl]-1,4-dihydro-3,5-pyridinedicarboxylate;

dimethyl 4-(2,6-dichlorophenyl)-2-[2-[4-[1-[(ethylamino)methyl]cyclohexyl]-1-piperidinyl]-2-oxoethyl]-6-[2-(1,3-thiazol-2-yl)ethyl]-1,4-dihydro-3,5-pyridinedicarboxylate; and dimethyl 4-(2,6-dichlorophenyl)-2-[2-oxo-2-[4-[8-(2-oxo-1-pyrrolidinyl)bicyclo[3.2.1]oct-3-yl]-1-piperazinyl]carbonyl]-6-[2-(1,3-thiazol-2-yl)ethyl]-1,4-dihydro-3,5-pyridinedicarboxylate.

7. A pharmaceutical composition for the treatment of pain, in a mammalian subject, which comprises a therapeutically effective amount of a compound of claim 1 or its pharmaceutically acceptable carrier.

8. A method for the treatment of pain, in a mammalian subject, which comprises administering to said subject a therapeutically effective amount of a compound according to claim 1.

9. A pharmaceutical formulation comprising a compound of claim 1, a pharmaceutically acceptable carrier and, optionally, one or more other therapeutic ingredients selected from antibiotic, anti-fungal, or anti-viral agent, an anti-histamine, a non-steroidal anti-inflammatory drug or disease modifying anti-rheumatic drug.

* * * * *